US010208348B2

(12) United States Patent
Lo et al.

(10) Patent No.: US 10,208,348 B2
(45) Date of Patent: Feb. 19, 2019

(54) DETERMINING PERCENTAGE OF FETAL DNA IN MATERNAL SAMPLE

(71) Applicant: The Chinese University of Hong Kong, Shatin, N.T. (CN)

(72) Inventors: Yuk-Ming Dennis Lo, Kowloon (CN); Rossa Wai Kwun Chiu, Shatin (CN); Kwan Chee Chan, Kowloon (CN); Benny Chung-Ying Zee, Ma on Shan (CN); Ka Chun Chong, Tai Po (CN)

(73) Assignee: The Chinese University of Hong Kong, New Territories (HK)

( * ) Notice: Subject to any disclaimer, the term of this patent is extended or adjusted under 35 U.S.C. 154(b) by 800 days.

(21) Appl. No.: 14/030,904

(22) Filed: Sep. 18, 2013

(65) Prior Publication Data

US 2014/0045181 A1 Feb. 13, 2014

Related U.S. Application Data

(62) Division of application No. 12/178,116, filed on Jul. 23, 2008, now Pat. No. 8,706,422.

(60) Provisional application No. 60/951,438, filed on Jul. 23, 2007.

(51) Int. Cl.
*C12Q 1/6883* (2018.01)
*G06F 19/18* (2011.01)
*C12Q 1/6827* (2018.01)
*C12Q 1/6888* (2018.01)
*G06F 19/22* (2011.01)

(52) U.S. Cl.
CPC ......... *C12Q 1/6883* (2013.01); *C12Q 1/6827* (2013.01); *C12Q 1/6888* (2013.01); *G06F 19/18* (2013.01); *C12Q 2600/112* (2013.01); *C12Q 2600/154* (2013.01); *C12Q 2600/156* (2013.01); *G01N 2800/387* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 6,440,706 | B1 | 8/2002 | Vogelstein et al. |
| 6,753,147 | B2 | 6/2004 | Vogelstein et al. |
| 7,727,720 | B2 | 6/2010 | Dhallan |
| 2003/0180765 | A1 | 9/2003 | Traverso et al. |
| 2004/0137470 | A1* | 7/2004 | Dhallan ............... C12Q 1/6806 435/6.16 |
| 2004/0209299 | A1 | 10/2004 | Pinter et al. |
| 2005/0130176 | A1 | 6/2005 | Vogelstein et al. |
| 2005/0221341 | A1 | 10/2005 | Shimkets et al. |
| 2005/0282213 | A1 | 12/2005 | Halle |
| 2007/0202525 | A1 | 8/2007 | Quake et al. |
| 2007/0207466 | A1 | 9/2007 | Cantor |

FOREIGN PATENT DOCUMENTS

| | | |
|---|---|---|
| CN | 1779688 A | 5/2006 |
| CN | 1997757 A | 7/2007 |
| EP | 1229135 A2 | 8/2002 |
| EP | 2007/075836 A2 | 7/2007 |
| JP | 2007515947 A | 6/2007 |
| JP | 2010534068 A | 11/2010 |
| KR | 10-1998-0086701 | 12/1998 |
| KR | 10-2002-0064298 | 8/2002 |
| KR | 20040102024 A | 12/2004 |
| WO | 2003/020974 A2 | 3/2003 |
| WO | 03074723 A2 | 9/2003 |
| WO | 2004/079011 A1 | 9/2004 |
| WO | 2004083816 A2 | 9/2004 |
| WO | 2005/035725 A1 | 4/2005 |
| WO | 2007/092473 A2 | 8/2007 |
| WO | 2007/132167 A2 | 11/2007 |
| WO | 2009013492 A1 | 1/2009 |

OTHER PUBLICATIONS

Chang, Hsueh-Wei et al.; "Assessment of Plasma DNA Levels, Allelic Imbalance, and CA 125 as Diagnostic Tests for Cancer"; 2002, Journal of the National Cancer Institute, vol. 94, No. 22, pp. 1697-1703.
Dhallan, R., et al., "A Non-Invasive Test for Prenatal Diagnosis Based on Fetal DNA Present in Maternal Blood: A Preliminary Study," www.thelancet.com, Feb. 2, 2007, 8 pages.
Diehl, Frank et al.; "Detection and quantification of mutations in the plasma of patients with colorectal tumors"; 2005, PNAS, vol. 102, No. 45, pp. 16368-16373.
El Karoui, Noureddine et al.; "Getting more from digital SNP data"; 2006, Statistics in Medicine, vol. 25, pp. 3124-3133.
Fan, H. C., et al., "Detection of Aneuploidy with Digital PCR," May 8, 2007, 14 pages, Department of Bioengineering, Stanford University and Howard Hughes Medical Institute, Stanford, CA.
Ottesen, Elizabeth A. et al.; "Microfluidic Digital PCR Enables Multigene Analysis of Individual Environmental Bacteria"; 2006, Science, vol. 314, pp. 1464-1467.

(Continued)

*Primary Examiner* — G Steven Vanni
(74) *Attorney, Agent, or Firm* — Kilpatrick Townsend & Stockton LLP

(57) ABSTRACT

Methods, systems, and apparatus are provided for determining whether a nucleic acid sequence imbalance exists within a biological sample. One or more cutoff values for determining an imbalance of, for example, the ratio of the two sequences (or sets of sequences) are chosen. The cutoff value may be determined based at least in part on the percentage of fetal DNA in a sample, such as maternal plasma, containing a background of maternal nucleic acid sequences. The percentage of fetal DNA can be calculated from the same or different data used to determine the cutoff value, and can use a locus where the mother is homozygous and the fetus is heterozygous. The cutoff value may be determined using many different types of methods, such as sequential probability ratio testing (SPRT).

29 Claims, 30 Drawing Sheets

Specification includes a Sequence Listing.

(56) References Cited

OTHER PUBLICATIONS

Panhard, Xaviere et al.; "Constructions of a global score quantifying allelic imbalance among biallelic SIDP markers in bladder cancer"; 2003, Statistics in Medicine, vol. 22, pp. 3771-3779.
Pohl, Gudrun et al.; "Principle and applications of digital PCR"; 2004, Expert Rev. Mol. Diagn., vol. 4, No. 1, pp. 41-47.
Vogelstein, Bert et al.; "Digital PCR"; 1999, PNAS, vol. 96, pp. 9236-9241.
Warren, Luigi et al.; "Transcription factor profiling in individual hematopoietic progenitors by digital RT-PCR"; 2006, PNAS, vol. 103, No. 47, pp. 17807-17812.
Zhou, Wei et al.; "Counting alleles to predict recurrence of early-stage colorectal cancers"; 2002, The Lancet, vol. 359, pp. 219-225.
Zhou, Wei et al.; "Counting alleles reveals a connection between chromosome 18q loss and vascular invasion"; 2001, Nature Biology, vol. 19, pp. 78-81.
Chiu, R., et al., "Application of fetal DNA in maternal plasma for noninvasive prenatal diagnosis," Expert Review of Molecular Diagnostics, vol. 2(1), pp. 32-40 (Jan. 2002).
Exam Report dated Aug. 3, 2010, for European Application No. 08 776 038.5, 7 pgs.
Exam Report dated Nov. 12, 2012, for European Application No. 08 776 038.5, 9 pgs.
Exam Report dated Nov. 22, 2011, for European Application No. 08 776 038.5, 7 pgs.
Examiner's first report on AU Patent Application No. 2008278839, dated May 10, 2012, 3 pgs.
International Search Report and Written Opinion for PCT/GB2008/002524, dated Oct. 30, 2008, 28 pgs.
International Search Report of PCT/IB2012/000015, dated Apr. 27, 2012, 4 pgs.
Lo, Y, et al., "Plasma placental RNA allelic ratio permits noninvasive prenatal chromosomal aneuploidy detection," Nature Medicine, vol. 13(2), Feb. 2007, pp. 218-223.
Lo, Y., et al., "Digital PCR for the molecular detection of fetal chromosomal aneuploidy," PNAS, vol. 104(32), pp. 13116-13121 (Aug. 7, 2007).
Lo, Y., et al., "Prenatal diagnosis: progress through plasma nucliec acids," Nature Reviews Genetics, vol. 8, Jan. 2007, pp. 71-77.
Lun, F., et al., "Noninvasive prenatal diagnosis of monogenic diseases by digital size selection and relative mutation dosage on DNA in maternal plasma," Proceedings of the National Academy of Sciences of the USA, vol. 105(50), pp. 19920-19925 (Dec. 16, 2008).
Notice of Reasons for Rejection, Translation, for Japanese Patent Application No. 2010-517480, dated Jun. 25, 2013, 7 pgs.
Office Action dated Aug. 27, 2012, and associate translation, for Chinese Patent Application No. 200880108126.3, 4 pgs.
Office Action dated Dec. 31, 2011, and associate translation, for Chinese Patent Application No. 200880108126.3, 4 pgs.
Office Action translation dated May 28, 2013, for Chinese Patent Application No. 200880108126.3, 3 pgs.
Rubben, A., et al., "Somatic deletion of the NFI gene in a neurofibromatosis type I-associated malignant melanoma demonstrated by digital PCR," Molecular Cancer, vol. 5, p. 36(1-9) (2006).
Shih, I-M., et al., "Evidence that genetic instability occurs at an early stage of colorectal tumorigenesis," Cancer Research, 2001, vol. 61, pp. 818-822.
Tong, Y.T., "Noninvasive prenatal detection of fetal trisomy 18 by epigenetic allelic ratio analysis in maternal plasma: Theoretical and empirical considerations," Clinical Chemistry, 2006, vol. 52, pp. 2194-2202.
Tsui, N., et al. "Noninvasive prenatal diagnosis of hemophilia by microfluidics digital PCR analysis of maternal plasma DNA," Blood, vol. 117(13), pp. 3684-3691 (Mar. 31, 2011).
Written Opinion of International Searching Authority of PCT/IB2012/000015, dated Apr. 27, 2012, 6 pgs.
Partial European Search Report dated Dec. 10, 2014 in EP 12180138, 12 pages.

Examination Report dated Jun. 5, 2014 in Australian Patent Application No. 2013202141, 12 pages.
Examination Report dated Jun. 5, 2014 in Australian Patent Application No. 2013202132, 4 pages.
Examination Report dated Jun. 5, 2014 in Australian Patent Application No. 2013202160, 13 pages.
Examination Report dated Jun. 5, 2014 in Australian Patent Application No. 2013202157, 12 pages.
Lo, Y.M.D., et al., "Quantitative Analysis of Fetal DNA in Maternal Plasma and Serum: Implications for Noninvasive Prenatal Diagnosis," American Journal of Human Genetics, 1998, vol. 62, pp. 768-775.
Reed, W., et al., "Non-invasive determination of the paternal HLA haplotype of a fetus using kinetic PCR to detect fetal microchimerism in maternal plasma," Bone Marrow Transplantation, 2002, vol. 29, pp. 527-529.
Ding, Chunming, "Other applications of single nucleotide polymorphisms," Trends in Biotechnology, Jun. 14, 2007, vol. 25, No. 7, pp. 279-283.
Extended European Search Report dated Jun. 25, 2014 in EP Patent Application No. 12180133, 10 pages.
Old, Robert, W., et al., "Candidate epigenetic biomarkers for non-invasive prenatal diagnosis of Down syndrome," Reproductive Biomedicine Online, Jan. 1, 2007, vol. 15, No. 2, pp. 227-235.
Chan, K.C., Allen, et al., "Hypermethylated RASSF1A in maternal plasma: A universal fetal DNA marker that improves the reliability of noninvasive prenatal diagnosis," Clinical Chemistry, Dec. 1, 2006, vol. 52, No. 12, pp. 2211-2218.
Chim, Stephen, S.C., et al., "Detection of the placental epigenetic signature of the maspin gene in maternal plasma," Proceedings of the National Academy of Sciences, Oct. 11, 2005, vol. 102, No. 41, pp. 14753-14758.
Tong, Yu K., et al., "Noninvasive Prenatal Detection of Trisomy 21 by an Epigenetic-Genetic Chromosome-Dosage Approach," Clinical Chemistry, Jan. 1, 2010, vol. 56, No. 1, pp. 90-98.
Tong, Yu K., et al., "Epigenetic-Genetic Chromosome Dosage Approach for Fetal Trisomy 21 Detection Using an Autosomal Genetic Reference Marker," PLOS One, Dec. 20, 2010, vol. 5, No. 12, 9 pages.
Della Ragione, Floriana, et al., "Differential DNA Methylation as a Tool for Noninvasive Prenatal Diagnosis (NIPD) of X Chromosome Aneuploidies," The Journal of Molecular Diagnostics, Nov. 1, 2010, vol. 12, No. 6, pp. 797-807.
Poon, Leo, L.M., et al., "Differential DNA methylation between fetus and mother as a strategy for detecting fetal DNA in maternal plasma," Clinical Chemistry, Jan. 1, 2001, vol. 48, No. 1, pp. 35-41.
European Search Report dated Sep. 9, 2014 in Application No. EP 12180129, 16 pages.
Examination Report dated Dec. 14, 2016 in AU Patent Application No. 2015271883. 4 pages.
English translation and Office Action dated Nov. 21, 2016 in KR Patent Application No. 10-2016-7021214. 12 pages.
Office Action dated Apr. 10, 2017 in CA Patent Application No. 2,694,007. 5 pages.
English translation of Office Action dated Jun. 13, 2017 in JP Patent Application No. 2013-267526. 4 pages.
Campbell, Peter J. et al.; "Identification of somatically acquired rearrangements in cancer using genome-wide massively parallel paired-end sequencing"; Nature Genetics; Jun. 2008; vol. 40, No. 6; p. 722-729.
English translation of Office Action dated Jun. 27, 2017 in JP Patent Application No. 2016-131552. 8 pages.
English translation of Office Action dated Feb. 18, 2018 in KR Patent Application No. 10-2016-7021211. 6 pages.
English translation of Trial Decision mailed Apr. 24, 2018 in JP Patent Application No. 2013-267526. 12 pages.
Communication pursuant to Article 94(3) EPC dated May 3, 2018 in EP Patent Application No. 12180122.9. 10 pages.
Communication pursuant to Article 94(3) EPC dated Nov. 2, 2018 in EP Patent Application No. 12180138.5. 6 pages.

(56) References Cited

OTHER PUBLICATIONS

Examination Report No. 1 dated Nov. 28, 2018 in AU Patent Application No. 2017236002. 4 pages.

* cited by examiner

| Cancer | Common chromosomal aberrations | |
|---|---|---|
| | Gain | Loss |
| Bladder cancer | 7 | 9p; 11q; 17p |
| Breast cancer | 1q; 8q; 17q; 20q | 8p; 13q; 16q; 18q |
| Colorectal cancer | 7; 8q; 13q; 20q | 1p; 5q; 8p; 15q; 17p; 18q |
| Hepatocellular carcinoma | 1q; 8q; 20q | 4q; 8p; 13q; 16q; 17p |
| Non – small cell lung carcinoma | 1q; 3q; 5p; 8q | 3p; 8p; 9p; 13q; 17p |
| Small cell lung cancinoma | 3q; 5p; 8q; 19q | 3p; 4q; 5q; 10q; 13q; 16q |
| Nasopharyngeal carcinoma | 1q; 3q; 8; 12; 19 | 1p; 3p; 9; 11q; 13q; 14q; 16q |
| Prostate cancer | 7; 8q; Xq | 8p; 13q; 16q |

FIG. 2B

| $m_r$ | Proportion of wells positive for the reference allele | Proportion of wells positive for the overrepresented allele | Proportion of wells positive for both alleles | Proportion of wells positive for the reference allele ONLY | Proportion of wells positive for the overrepresented allele ONLY | Digital RNA-SNP allelic ratio | Proportion of informative wells | $P_r$ |
|---|---|---|---|---|---|---|---|---|
| 0.1 | 0.0952 | 0.1813 | 0.0173 | 0.0779 | 0.164 | 2.11 | 0.2419 | 0.68 |
| 0.2 | 0.1813 | 0.3297 | 0.0598 | 0.1215 | 0.2699 | 2.22 | 0.3914 | 0.69 |
| 0.3 | 0.2592 | 0.4512 | 0.1169 | 0.1422 | 0.3342 | 2.35 | 0.4765 | 0.7 |
| 0.4 | 0.3297 | 0.5507 | 0.1815 | 0.1481 | 0.3691 | 2.49 | 0.5173 | 0.71 |
| 0.5 | 0.3935 | 0.6321 | 0.2487 | 0.1448 | 0.3834 | 2.65 | 0.5282 | 0.73 |
| 0.6 | 0.4512 | 0.6988 | 0.3153 | 0.1359 | 0.3835 | 2.82 | 0.5194 | 0.74 |
| 0.7 | 0.5034 | 0.7534 | 0.3793 | 0.1241 | 0.3741 | 3.01 | 0.4983 | 0.75 |
| 0.8 | 0.5507 | 0.7981 | 0.4395 | 0.1112 | 0.3586 | 3.23 | 0.4698 | 0.76 |
| 0.9 | 0.5934 | 0.8347 | 0.4953 | 0.0981 | 0.3394 | 3.46 | 0.4375 | 0.78 |
| 1 | 0.6321 | 0.8647 | 0.5466 | 0.0855 | 0.3181 | 3.72 | 0.4036 | 0.79 |
| 1.1 | 0.6671 | 0.8892 | 0.5932 | 0.0739 | 0.296 | 4 | 0.3699 | 0.8 |
| 1.2 | 0.6988 | 0.9093 | 0.6354 | 0.0634 | 0.2739 | 4.32 | 0.3373 | 0.81 |
| 1.3 | 0.7275 | 0.9257 | 0.6734 | 0.054 | 0.2523 | 4.67 | 0.3063 | 0.82 |
| 1.4 | 0.7534 | 0.9392 | 0.7076 | 0.0458 | 0.2316 | 5.06 | 0.2774 | 0.83 |
| 1.5 | 0.7769 | 0.9502 | 0.7382 | 0.0387 | 0.212 | 5.48 | 0.2507 | 0.85 |
| 1.6 | 0.7981 | 0.9592 | 0.7656 | 0.0325 | 0.1937 | 5.95 | 0.2262 | 0.86 |
| 1.7 | 0.8173 | 0.9666 | 0.79 | 0.0273 | 0.1766 | 6.47 | 0.2039 | 0.87 |
| 1.8 | 0.8347 | 0.9727 | 0.8119 | 0.0228 | 0.1608 | 7.05 | 0.1836 | 0.88 |
| 1.9 | 0.8504 | 0.9776 | 0.8314 | 0.019 | 0.1462 | 7.69 | 0.1652 | 0.88 |
| 2 | 0.8647 | 0.9817 | 0.8488 | 0.0158 | 0.1329 | 8.39 | 0.1487 | 0.89 |

FIG. 6

| $m_r$ | Percentage of fetal DNA in the sample | | | | | | | |
|---|---|---|---|---|---|---|---|---|
| | 10% | | 25% | | 50% | | 100% | |
| | Percentage of informative wells | $P_r$ | Percentage of informative wells | $P_r$ | Percentage of informative wells | $P_r$ | Percentage of informative wells | $P_r$ |
| 0.1 | 18% | 0.51 | 18% | 0.53 | 19% | 0.56 | 21% | 0.61 |
| 0.2 | 30% | 0.51 | 31% | 0.53 | 32% | 0.56 | 35% | 0.61 |
| 0.3 | 39% | 0.51 | 40% | 0.53 | 41% | 0.57 | 43% | 0.62 |
| 0.4 | 45% | 0.51 | 45% | 0.54 | 46% | 0.57 | 48% | 0.63 |
| 0.5 | 48% | 0.52 | 49% | 0.54 | 49% | 0.57 | 51% | 0.63 |
| 0.6 | 50% | 0.52 | 50% | 0.54 | 50% | 0.58 | 51% | 0.64 |
| 0.7 | 50% | 0.52 | 50% | 0.54 | 50% | 0.58 | 50% | 0.65 |
| 0.8 | 49% | 0.52 | 49% | 0.55 | 49% | 0.58 | 48% | 0.65 |
| 0.9 | 48% | 0.52 | 47% | 0.55 | 47% | 0.59 | 46% | 0.66 |
| 1 | 46% | 0.52 | 45% | 0.55 | 44% | 0.59 | 43% | 0.67 |
| 1.1 | 44% | 0.52 | 43% | 0.55 | 42% | 0.6 | 40% | 0.68 |
| 1.2 | 41% | 0.52 | 40% | 0.55 | 39% | 0.6 | 37% | 0.69 |
| 1.3 | 39% | 0.52 | 38% | 0.55 | 36% | 0.6 | 34% | 0.69 |
| 1.4 | 36% | 0.52 | 35% | 0.56 | 33% | 0.61 | 31% | 0.7 |
| 1.5 | 34% | 0.52 | 33% | 0.56 | 31% | 0.61 | 28% | 0.71 |
| 1.6 | 31% | 0.52 | 30% | 0.56 | 28% | 0.62 | 26% | 0.72 |
| 1.7 | 29% | 0.53 | 28% | 0.56 | 26% | 0.62 | 23% | 0.73 |
| 1.8 | 27% | 0.53 | 25% | 0.57 | 24% | 0.63 | 21% | 0.73 |
| 1.9 | 24% | 0.53 | 23% | 0.57 | 21% | 0.63 | 19% | 0.74 |
| 2 | 22% | 0.53 | 21% | 0.57 | 20% | 0.64 | 17% | 0.75 |

700

| nr | | New algorithm | | Old algorithm | | nr | Classification | New algorithm | | Old algorithm | |
|---|---|---|---|---|---|---|---|---|---|---|---|
| | Classification | Euploid | Trisomy 21 | Euploid | Trisomy 21 | | | Euploid | Trisomy 21 | Euploid | Trisomy 21 |
| 0.1 | Correct | 0% | 37% | 0% | 35% | 1.1 | correct | 89% | 92% | 14% | 35% |
| | Incorrect | 3% | 2% | 3% | 1% | | Incorrect | 1% | 0% | 4% | 0% |
| | Unclassified | 97% | 61% | 97% | 63% | | Unclassified | 10% | 7% | 81% | 65% |
| 0.2 | Correct | 6% | 64% | 0% | 40% | 1.2 | correct | 90% | 92% | 11% | 35% |
| | Incorrect | 4% | 2% | 4% | 0% | | Incorrect | 1% | 0% | 4% | 0% |
| | Unclassified | 90% | 34% | 96% | 60% | | Unclassified | 9% | 8% | 84% | 65% |
| | Correct | 34% | 75% | 6% | 39% | 1.3 | correct | 91% | 92% | 7% | 34% |
| | Incorrect | 4% | 2% | 4% | 0% | | Incorrect | 1% | 1% | 4% | 0% |
| | Unclassified | 62% | 24% | 90% | 61% | | Unclassified | 8% | 7% | 89% | 66% |
| 0.3 | Correct | 54% | 81% | 14% | 39% | 1.4 | correct | 92% | 91% | 5% | 34% |
| | Incorrect | 3% | 1% | 4% | 0% | | Incorrect | 1% | 1% | 4% | 0% |
| | Unclassified | 43% | 19% | 82% | 61% | | Unclassified | 8% | 9% | 91% | 66% |
| 0.4 | Correct | 64% | 85% | 20% | 38% | 1.5 | correct | 92% | 90% | 2% | 32% |
| | Incorrect | 3% | 1% | 4% | 0% | | Incorrect | 1% | 1% | 4% | 0% |
| | Unclassified | 33% | 14% | 76% | 62% | | Unclassified | 8% | 9% | 93% | 68% |
| 0.5 | Correct | 74% | 88% | 23% | 38% | 1.6 | correct | 92% | 89% | 1% | 31% |
| | Incorrect | 2% | 1% | 4% | 0% | | Incorrect | 1% | 1% | 4% | 0% |
| | Unclassified | 24% | 11% | 72% | 62% | | Unclassified | 8% | 10% | 94% | 69% |
| 0.6 | Correct | 80% | 89% | 25% | 37% | 1.7 | correct | 92% | 89% | 1% | 30% |
| | Incorrect | 2% | 1% | 4% | 0% | | Incorrect | 1% | 1% | 4% | 0% |
| | Unclassified | 18% | 10% | 71% | 63% | | Unclassified | 7% | 10% | 96% | 70% |
| 0.7 | Correct | 83% | 91% | 23% | 37% | 1.8 | correct | 92% | 88% | 0% | 28% |
| | Incorrect | 2% | 1% | 4% | 0% | | Incorrect | 1% | 1% | 4% | 0% |
| | Unclassified | 15% | 9% | 73% | 63% | | Unclassified | 7% | 11% | 96% | 72% |
| 0.8 | Correct | 86% | 91% | 21% | 36% | 1.9 | correct | 92% | 87% | 0% | 26% |
| | Incorrect | 1% | 1% | 4% | 0% | | Incorrect | 1% | 1% | 3% | 0% |
| | Unclassified | 12% | 8% | 75% | 64% | | Unclassified | 8% | 12% | 97% | 74% |
| 0.9 | Correct | 88% | 92% | 19% | 36% | 2 | correct | 91% | 86% | 0% | 24% |
| | Incorrect | 1% | 0% | 4% | 0% | | Incorrect | 1% | 1% | 4% | 0% |
| | Unclassified | 11% | 8% | 77% | 64% | | Unclassified | 9% | 13% | 96% | 76% |

FIG. 9A

| | | New algorithm | | Old algorithm | | | $m_r$ | Classification | New algorithm | | Old algorithm | |
|---|---|---|---|---|---|---|---|---|---|---|---|---|
| $m_r$ | Classification | Euploid | Trisomy 21 | Euploid | Trisomy 21 | | | | Euploid | Trisomy 21 | Euploid | Trisomy 21 |
| 0.1 | correct | 57% | 88% | 48% | 89% | | 1.1 | correct | 100% | 100% | 92% | 90% |
| | Incorrect | 3% | 1% | 3% | 1% | | | Incorrect | 0% | 0% | 1% | 0% |
| | Unclassified | 40% | 11% | 49% | 10% | | | Unclassified | 0% | 0% | 7% | 10% |
| 0.2 | correct | 89% | 98% | 79% | 90% | | 1.2 | correct | 100% | 100% | 90% | 90% |
| | Incorrect | 1% | 0% | 2% | 0% | | | Incorrect | 0% | 0% | 1% | 0% |
| | Unclassified | 10% | 2% | 19% | 10% | | | Unclassified | 0% | 0% | 9% | 10% |
| 0.3 | correct | 96% | 99% | 88% | 90% | | 1.3 | correct | 100% | 100% | 89% | 90% |
| | Incorrect | 0% | 0% | 1% | 0% | | | Incorrect | 0% | 0% | 1% | 0% |
| | Unclassified | 4% | 1% | 11% | 10% | | | Unclassified | 0% | 0% | 10% | 10% |
| 0.4 | correct | 99% | 100% | 92% | 90% | | 1.4 | correct | 100% | 100% | 87% | 90% |
| | Incorrect | 0% | 0% | 1% | 0% | | | Incorrect | 0% | 0% | 1% | 0% |
| | Unclassified | 1% | 0% | 7% | 10% | | | Unclassified | 0% | 0% | 12% | 10% |
| 0.5 | correct | 100% | 100% | 94% | 90% | | 1.5 | correct | 100% | 100% | 85% | 90% |
| | Incorrect | 0% | 0% | 1% | 0% | | | Incorrect | 0% | 0% | 1% | 0% |
| | Unclassified | 0% | 0% | 6% | 10% | | | Unclassified | 0% | 0% | 13% | 10% |
| 0.6 | correct | 100% | 100% | 94% | 90% | | 1.6 | correct | 100% | 100% | 82% | 90% |
| | Incorrect | 0% | 0% | 1% | 0% | | | Incorrect | 0% | 0% | 1% | 0% |
| | Unclassified | 0% | 0% | 5% | 10% | | | Unclassified | 0% | 0% | 17% | 10% |
| 0.7 | correct | 100% | 100% | 95% | 90% | | 1.7 | correct | 100% | 100% | 79% | 90% |
| | Incorrect | 0% | 0% | 1% | 0% | | | Incorrect | 0% | 0% | 2% | 0% |
| | Unclassified | 0% | 0% | 5% | 10% | | | Unclassified | 0% | 0% | 19% | 10% |
| 0.8 | correct | 100% | 100% | 95% | 90% | | 1.8 | correct | 100% | 100% | 74% | 90% |
| | Incorrect | 0% | 0% | 1% | 0% | | | Incorrect | 0% | 0% | 2% | 0% |
| | Unclassified | 0% | 0% | 5% | 10% | | | Unclassified | 0% | 0% | 24% | 10% |
| 0.9 | correct | 100% | 100% | 94% | 90% | | 1.9 | correct | 100% | 100% | 70% | 90% |
| | Incorrect | 0% | 0% | 1% | 0% | | | Incorrect | 0% | 0% | 2% | 0% |
| | Unclassified | 0% | 0% | 6% | 10% | | | Unclassified | 0% | 0% | 28% | 10% |
| 1 | correct | 100% | 100% | 94% | 90% | | 2 | correct | 100% | 100% | 67% | 90% |
| | Incorrect | 0% | 0% | 1% | 0% | | | Incorrect | 0% | 0% | 3% | 0% |
| | Unclassified | 0% | 0% | 6% | 10% | | | Unclassified | 0% | 0% | 30% | 10% |

FIG. 9B

| $m_r$ | Classification result | Euploid | T21 | $m_r$ | Classification result | Euploid | T21 |
|---|---|---|---|---|---|---|---|
| 0.1 | Correct | 57% | 88% | 0.9 | Correct | 100% | 100% |
| | Incorrect | 3% | 1% | | Incorrect | 0% | 0% |
| | Unclassified | 40% | 11% | | Unclassified | 0% | 0% |
| 0.2 | Correct | 89% | 98% | 1 | Correct | 100% | 100% |
| | Incorrect | 1% | 0% | | Incorrect | 0% | 0% |
| | Unclassified | 10% | 2% | | Unclassified | 0% | 0% |
| 0.3 | Correct | 96% | 99% | 1.1 | Correct | 100% | 100% |
| | Incorrect | 0% | 0% | | Incorrect | 0% | 0% |
| | Unclassified | 4% | 1% | | Unclassified | 0% | 0% |
| 0.4 | Correct | 99% | 100% | 1.2 | Correct | 100% | 100% |
| | Incorrect | 0% | 0% | | Incorrect | 0% | 0% |
| | Unclassified | 1% | 0% | | Unclassified | 0% | 0% |
| 0.5 | Correct | 100% | 100% | 1.3 | Correct | 100% | 100% |
| | Incorrect | 0% | 0% | | Incorrect | 0% | 0% |
| | Unclassified | 0% | 0% | | Unclassified | 0% | 0% |
| 0.6 | Correct | 100% | 100% | 1.4 | Correct | 100% | 100% |
| | Incorrect | 0% | 0% | | Incorrect | 0% | 0% |
| | Unclassified | 0% | 0% | | Unclassified | 0% | 0% |
| 0.7 | Correct | 100% | 100% | 1.5 | Correct | 100% | 100% |
| | Incorrect | 0% | 0% | | Incorrect | 0% | 0% |
| | Unclassified | 0% | 0% | | Unclassified | 0% | 0% |
| 0.8 | Correct | 100% | 100% | 2 | Correct | 100% | 100% |
| | Incorrect | 0% | 0% | | Incorrect | 0% | 0% |
| | Unclassified | 0% | 0% | | Unclassified | 0% | 0% |

FIG. 10

| $m_r$ | Classification result | Euploid | Trisomy 21 | $m_r$ | Classification result | Euploid | Trisomy 21 |
|---|---|---|---|---|---|---|---|
| 0.1 | Correct | 38% | 44% | 0.7 | Correct | 95% | 94% |
| | Incorrect | 2% | 2% | | Incorrect | 0% | 1% |
| | Unclassified | 60% | 54% | | Unclassified | 5% | 5% |
| 0.2 | Correct | 64% | 69% | 0.8 | Correct | 95% | 95% |
| | Incorrect | 2% | 2% | | Incorrect | 1% | 0% |
| | Unclassified | 34% | 29% | | Unclassified | 4% | 5% |
| 0.3 | Correct | 78% | 82% | 0.9 | Correct | 96% | 96% |
| | Incorrect | 2% | 1% | | Incorrect | 0% | 0% |
| | Unclassified | 20% | 17% | | Unclassified | 4% | 4% |
| 0.4 | Correct | 85% | 87% | 1 | Correct | 97% | 96% |
| | Incorrect | 1% | 1% | | Incorrect | 0% | 0% |
| | Unclassified | 14% | 12% | | Unclassified | 3% | 4% |
| 0.5 | Correct | 89% | 90% | 1.5 | Correct | 97% | 96% |
| | Incorrect | 1% | 1% | | Incorrect | 0% | 0% |
| | Unclassified | 10% | 9% | | Unclassified | 3% | 4% |
| 0.6 | Correct | 92% | 93% | 2 | Correct | 96% | 95% |
| | Incorrect | 1% | 1% | | Incorrect | 0% | 0% |
| | Unclassified | 7% | 7% | | Unclassified | 4% | 5% |

FIG. 11

| Number of wells | Classification results | Fetal DNA percentage in the sample | | | | | | | |
|---|---|---|---|---|---|---|---|---|---|
| | | 10% | | 25% | | 50% | | 100% | |
| | | Euploid | Trisomy 21 | Euploid | Trisomy 21 | Euploid | Trisomy 21 | Euploid | Trisomy 21 |
| 384 | Correct | 0% | 0% | 6% | 7% | 47% | 49% | 89% | 90% |
| | Incorrect | 0% | 0% | 0% | 1% | 2% | 2% | 1% | 1% |
| | Unclassified | 100% | 100% | 93% | 92% | 51% | 49% | 10% | 9% |
| 768 | Correct | 0% | 0% | 23% | 24% | 73% | 76% | 98% | 99% |
| | Incorrect | 0% | 0% | 2% | 2% | 2% | 1% | 0% | 0% |
| | Unclassified | 100% | 100% | 75% | 74% | 25% | 23% | 2% | 1% |
| 1152 | Correct | 1% | 1% | 39% | 40% | 86% | 87% | 100% | 100% |
| | Incorrect | 0% | 0% | 2% | 2% | 1% | 1% | 0% | 0% |
| | Unclassified | 99% | 99% | 59% | 58% | 13% | 12% | 0% | 0% |
| 1536 | Correct | 2% | 2% | 50% | 51% | 93% | 93% | 100% | 100% |
| | Incorrect | 0% | 0% | 2% | 2% | 1% | 1% | 0% | 0% |
| | Unclassified | 98% | 97% | 48% | 47% | 7% | 6% | 0% | 0% |
| 1920 | Correct | 4% | 4% | 60% | 60% | 96% | 96% | 100% | 100% |
| | Incorrect | 0% | 1% | 2% | 2% | 0% | 0% | 0% | 0% |
| | Unclassified | 96% | 95% | 38% | 37% | 4% | 3% | 0% | 0% |
| 3840 | Correct | 18% | 19% | 84% | 83% | 100% | 100% | 100% | 100% |
| | Incorrect | 1% | 1% | 1% | 1% | 0% | 0% | 0% | 0% |
| | Unclassified | 81% | 80% | 15% | 15% | 18% | 22% | 0% | 0% |
| 7680 | Correct | 43% | 45% | 97% | 97% | 100% | 100% | 100% | 100% |
| | Incorrect | 2% | 2% | 0% | 0% | 0% | 0% | 0% | 0% |
| | Unclassified | 55% | 53% | 3% | 3% | 0% | 0% | 0% | 0% |

| sample | geno-type[a] | no. of wells | no. of wells positive for individual alleles | | | | $m_r$[b] | $P_r$[c] | SPRT result | |
|---|---|---|---|---|---|---|---|---|---|---|
| | | | A only | G only | AG | all negative | | | unclassifiable region[d] | classification[e] |
| *Placental DNA* | | | | | | | | | | |
| N677 | AG | 384 | 85 | 83 | 126 | 90 | 0.79 | 0.51 | 0.63 - 0.65 | euploid |
| N710 | AG | 384 | 102 | 83 | 73 | 126 | 0.52 | 0.55 | 0.61 - 0.63 | euploid |
| N435 | AGG | 384 | 49 | 157 | 130 | 48 | 0.63 | 0.76 | 0.62 - 0.64 | T21 |
| N981 | AAG | 384 | 135 | 69 | 82 | 98 | 0.5 | 0.66 | 0.61 - 0.63 | T21 |
| *Placental RNA* | | | | | | | | | | |
| V533 | AG | 384 | 103 | 93 | 71 | 117 | 0.56 | 0.53 | 0.61 - 0.63 | euploid |
| V943 | AG | 384 | 89 | 100 | 74 | 121 | 0.55 | 0.53 | 0.61 - 0.63 | euploid |
| N435 | AGG | 384 | 52 | 138 | 95 | 99 | 0.48 | 0.73 | 0.61 - 0.63 | T21 |
| T215 | AAG | 384 | 146 | 58 | 138 | 42 | 0.71 | 0.72 | 0.62 - 0.64 | T21 |

| sample | geno-type | no. of wells | no. of wells positive for individual alleles | | | | m | ratio | SPRT result | |
|---|---|---|---|---|---|---|---|---|---|---|
| | | | A only | G only | AG | all negative | | | unclassifiable region | classification |
| M2390P | AG | 384 | 90 | 100 | 97 | 97 | 0.67 | 0.526 | 0.62 - 0.64 | euploid |
| M2391P | AG | 384 | 97 | 105 | 65 | 117 | 0.55 | 0.52 | 0.61 - 0.63 | euploid |
| M2473P | AG | 384 | 66 | 92 | 34 | 192 | 0.3 | 0.582 | 0.59 - 0.62 | euploid |
| M2524P | AG | 384 | 29 | 28 | 3 | 324 | 0.08 | 0.509 | 0.54 - 0.64 | euploid |
| M2528P | AG | 384 | 112 | 85 | 44 | 143 | 0.41 | 0.569 | 0.60 - 0.62 | euploid |
| M2601P | AG | 384 | 90 | 101 | 72 | 121 | 0.55 | 0.529 | 0.61 - 0.63 | euploid |
| M2607P | AG | 384 | 73 | 91 | 57 | 163 | 0.41 | 0.555 | 0.60 - 0.63 | euploid |
| M2638P | AG | 384 | 66 | 90 | 52 | 176 | 0.37 | 0.577 | 0.59 - 0.62 | euploid |
| M2639P | AG | 384 | 71 | 56 | 17 | 240 | 0.21 | 0.559 | 0.58 - 0.62 | euploid |
| M2525P | AAG | 384 | 110 | 53 | 21 | 200 | 0.21 | 0.675 | 0.58 - 0.61 | T21 |
| M2272P | AAG | 768 | 246 | 127 | 112 | 283 | 0.37 | 0.66 | 0.60 - 0.61 | T21 |
| M2718P | AGG | 384 | 66 | 114 | 66 | 138 | 0.42 | 0.633 | 0.60 - 0.62 | T21 |
| M1519P | AGG | 384 | 58 | 130 | 54 | 142 | 0.34 | 0.691 | 0.59 - 0.62 | T21 |

1350

| sample | genotype | no. of wells | no. of wells positive for individual alleles | | | | $m_r^a$ | $P_r^b$ | SPRT result | |
|---|---|---|---|---|---|---|---|---|---|---|
| | | | A only | G only | GA | all negative | | | unclassifiable region | classification[c] |
| V943 | AG | 765 | 168 | 209 | 117 | 271 | 0.47 | 0.554 | 0.609- 0.621 | euploid |
| N435 | AGG | 765 | 92 | 281 | 105 | 287 | 0.30 | 0.753 | 0.597- 0.610 | T21 |
| T21-5 | AAG | 765 | 267 | 126 | 141 | 231 | 0.43 | 0.679 | 0.607- 0.618 | T21 |

[a] no. of reference molecules per well

[b] $P_r$ values were calculated by the equation:

$$P_r = \frac{\text{no. of wells positive for the overrepresented allele}}{\text{no. of wells positive for A only + no of wells positive for G only}}$$

[c] "Euploid" was assigned when the Pr was below the unclassifiable region; "T21" was assigned when the Pr was above the unclassifiable region. T21, trisomy 21

FIG. 15A

| panel # | no. of wells | no. wells positive for individual alleles | | | |
|---|---|---|---|---|---|
| | | A only | G only | GA | all negative |
| S1 | 765 | 14 | 15 | 0 | 736 |
| S2 | 765 | 7 | 10 | 0 | 748 |
| S3 | 765 | 13 | 9 | 1 | 744 |
| S4 | 765 | 7 | 8 | 0 | 750 |
| S5 | 765 | 12 | 8 | 0 | 745 |
| S6 | 765 | 8 | 14 | 0 | 743 |
| S7 | 765 | 13 | 9 | 0 | 743 |
| S8 | 765 | 9 | 8 | 0 | 748 |
| S9 | 765 | 14 | 15 | 0 | 736 |
| S10 | 765 | 9 | 12 | 0 | 744 |
| S11 | 765 | 8 | 17 | 0 | 740 |
| S12 | 765 | 11 | 9 | 0 | 745 |

FIG. 15B

| sample | geno-type | panels[a] | no. of wells positive for individual alleles | | | | $P_r$ | SPRT result | |
|---|---|---|---|---|---|---|---|---|---|
| | | | no of wells | A only | G only | GA | all negative | | unclassifiable region | classification |
| M2879P | AG | 5 | 3825 | 82 | 103 | 5 | 3635 | 0.557 | 0.570- 0.602 | Euploid |
| M2875P | AG | 3 | 2295 | 35 | 40 | 0 | 2220 | 0.533 | 0.546- 0.625 | Euploid |
| M3078P | AG | 3 | 2295 | 33 | 33 | 1 | 2228 | 0.500 | 0.541- 0.631 | Euploid |
| M2976P | AG | 12 | 9180 | 56 | 46 | 0 | 9078 | 0.549 | 0.556- 0.615 | Euploid |
| M2831P | AAG | 2 | 1530 | 42 | 13 | 0 | 1475 | 0.764 | 0.531- 0.640 | T21 |

[a] no. of panels needed for classification

FIG. 15C

| Sample | Genotype[a] | No. of wells positive for A or G allele | | | $m_r$[b] | SPRT analysis | | Classification[e] |
|---|---|---|---|---|---|---|---|---|
| | | A only | G only | Both | | $P_r$[c] | Unclassifiable region[d] | |
| N3505 | AG | 157 | 131 | 48 | 0.27 | 0.545 | 0.59-0.61 | Euploid |
| N3530 | AG | 174 | 132 | 52 | 0.28 | 0.569 | 0.59-0.61 | Euploid |
| N3531 | AG | 146 | 129 | 28 | 0.23 | 0.531 | 0.58-0.60 | Euploid |
| N3533 | AG | 149 | 135 | 46 | 0.27 | 0.525 | 0.59-0.61 | Euploid |
| N2772 | AG | 159 | 149 | 79 | 0.35 | 0.516 | 0.60-0.61 | Euploid |
| N3506 | AG | 154 | 145 | 66 | 0.32 | 0.515 | 0.60-0.61 | Euploid |
| N3555 | AG | 94 | 73 | 7 | 0.11 | 0.563 | 0.58-0.61 | Euploid |
| N3560 | AG | 101 | 109 | 28 | 0.18 | 0.519 | 0.58-0.61 | Euploid |
| N3561 | AG | 91 | 70 | 17 | 0.12 | 0.565 | 0.58-0.61 | Euploid |
| N828 | AAG | 153 | 89 | 22 | 0.16 | 0.632 | 0.58-0.60 | T18 |
| CA2 | AGG | 12 | 28 | 0 | 0.016 | 0.700 | 0.51-0.66 | T18 |
| CA7 | AGG | 97 | 171 | 56 | 0.22 | 0.638 | 0.59-0.61 | T18 |

[a] Genotypes were determined by mass spectrometry.
[b] The $m_r$ value indicates the average number of reference template molecules per well.
[c] The $P_r$ value indicates the proportion of informative wells positive for the overrepresented allele.
[d] The unclassifiable region varies with the $m_r$ value.
[e] "Euploid" was assigned when $P_r$ was below the unclassifiable region; "T18" was assigned when $P_r$ was above the unclassifiable region.

FIG. 16A

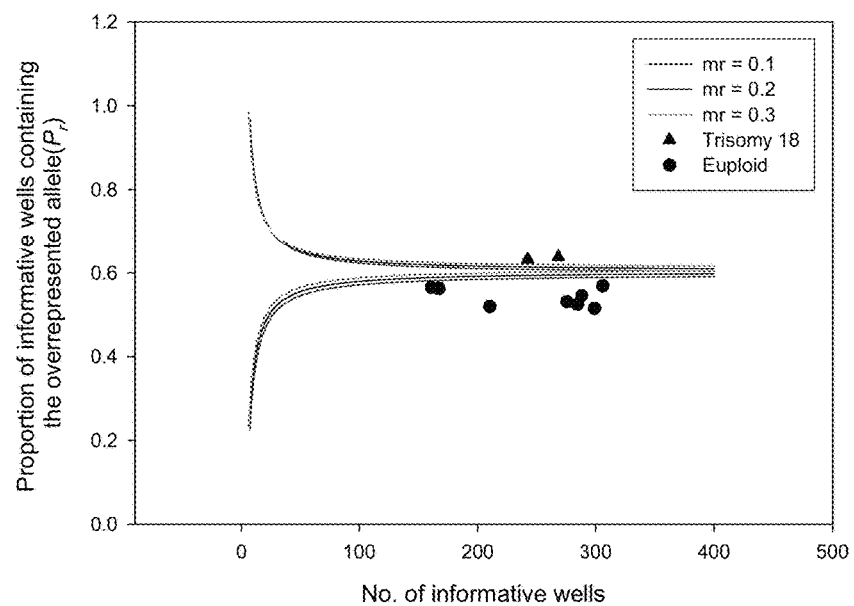

FIG. 16B

| Type | Cases | Total No. of panels used | Total No. of informative wells | No. of well count | | | $m_r^a$ | $P_r^b$ | SPRT analysis | | Classification[c] |
|---|---|---|---|---|---|---|---|---|---|---|---|
| | | | | Both positive | Chr21 only | Chr1 only | | | Unclassifiable region | | |
| T21 | N0234 | 1 | 303 | 68 | 172 | 131 | 0.30 | 0.568 | 0.507 - 0.559 | | T21 |
| | N0274 | 2 | 558 | 118 | 307 | 251 | 0.28 | 0.550 | 0.518 - 0.547 | | T21 |
| | N0332 | 1 | 293 | 73 | 188 | 125 | 0.30 | 0.573 | 0.506 - 0.560 | | T21 |
| | N0349 | 2 | 574 | 107 | 322 | 252 | 0.27 | 0.561 | 0.518 - 0.546 | | T21 |
| | N0435 | 1 | 299 | 67 | 176 | 123 | 0.29 | 0.599 | 0.506 - 0.559 | | T21 |
| | N0456 | 1 | 318 | 68 | 189 | 129 | 0.30 | 0.594 | 0.506 - 0.558 | | T21 |
| | N0667 | 2 | 602 | 134 | 345 | 257 | 0.30 | 0.573 | 0.519 - 0.546 | | T21 |
| | N0764 | 1 | 288 | 62 | 167 | 122 | 0.28 | 0.578 | 0.505 - 0.560 | | T21 |
| | N0890 | 4 | 1208 | 272 | 657 | 549 | 0.31 | 0.545 | 0.526 - 0.539 | | T21 |
| | N0891 | 1 | 317 | 103 | 180 | 137 | 0.30 | 0.568 | 0.518 - 0.559 | | T21 |
| Normal | N0196 | 1 | 262 | 68 | 111 | 151 | 0.34 | 0.424 | 0.504 - 0.563 | | Euploid |
| | N0198 | 1 | 285 | 68 | 132 | 153 | 0.34 | 0.463 | 0.506 - 0.561 | | Euploid |
| | N0230 | 2 | 527 | 109 | 272 | 256 | 0.27 | 0.516 | 0.517 - 0.548 | | Euploid |
| | N0231 | 2 | 542 | 99 | 275 | 267 | 0.27 | 0.507 | 0.517 - 0.547 | | Euploid |
| | N0262 | 1 | 295 | 57 | 144 | 151 | 0.32 | 0.488 | 0.506 - 0.560 | | Euploid |
| | N0463 | 1 | 263 | 70 | 120 | 143 | 0.33 | 0.456 | 0.504 - 0.563 | | Euploid |
| | N0527 | 1 | 292 | 56 | 137 | 155 | 0.32 | 0.469 | 0.506 - 0.560 | | Euploid |
| | N0619 | 1 | 281 | 60 | 138 | 143 | 0.31 | 0.491 | 0.505 - 0.561 | | Euploid |
| | N0625 | 1 | 291 | 60 | 134 | 157 | 0.33 | 0.460 | 0.507 - 0.560 | | Euploid |
| | N0651 | 2 | 566 | 118 | 287 | 279 | 0.30 | 0.507 | 0.519 - 0.547 | | Euploid |

[a] no. of reference molecules per well
[b] $P_r$ values were calculated by the equation:

no. of wells positive for the overrepresented allele (chr21)
―――――――――――――――――――――――――――――――――
no. of wells positive for chr21 only + no. of wells positive for chr1 only

[c] "Euploid" was assigned when the $P_r$ was below the unclassifiable region; "T21" was assigned when the $P_r$ was above the unclassifiable region.

FIG. 17

| Type | Cases | No. of parents used | No. of informative wells | No. of well counts | | | $m_r^a$ | $P_r^b$ | SPRT analysis | |
|---|---|---|---|---|---|---|---|---|---|---|
| | | | | Both positive | Chr21 only | Chr1 only | | | Unclassifiable region | Classification[c] |
| T21 | A0274 | 1 | 380 | 269 | 249 | 131 | 0.74 | 0.655 | 0.567 - 0.585 | T21 |
| | A2006 | 1 | 348 | 373 | 233 | 115 | 1.02 | 0.870 | 0.579 - 0.596 | T21 |
| | A2178 | 1 | 384 | 298 | 239 | 145 | 0.83 | 0.822 | 0.571 - 0.588 | T21 |
| | AS863A | 1 | 364 | 109 | 244 | 120 | 0.38 | 0.670 | 0.561 - 0.573 | T21 |
| | AS879A | 1 | 256 | 492 | 188 | 68 | 1.32 | 0.734 | 0.590 - 0.610 | T21 |
| | AS9457A | 1 | 376 | 83 | 256 | 120 | 0.31 | 0.681 | 0.548 - 0.572 | T21 |
| Normal | A0236 | 1 | 387 | 275 | 195 | 192 | 0.94 | 0.504 | 0.576 - 0.592 | Euploid |
| | A0237 | 1 | 392 | 228 | 184 | 208 | 0.84 | 0.469 | 0.572 - 0.588 | Euploid |
| | A0253 | 1 | 378 | 222 | 195 | 183 | 0.75 | 0.516 | 0.568 - 0.585 | Euploid |
| | AS365A | 1 | 254 | 43 | 127 | 127 | 0.25 | 0.500 | 0.541 - 0.576 | Euploid |
| | AS395A | 1 | 370 | 135 | 192 | 178 | 0.53 | 0.519 | 0.558 - 0.578 | Euploid |
| | AS463A | 1 | 354 | 84 | 186 | 168 | 0.38 | 0.525 | 0.550 - 0.574 | Euploid |
| | AS484A | 1 | 372 | 271 | 194 | 178 | 0.88 | 0.522 | 0.573 - 0.590 | Euploid |
| | AS780A | 1 | 413 | 188 | 200 | 213 | 0.74 | 0.484 | 0.568 - 0.584 | Euploid |
| | AS790A | 1 | 316 | 67 | 159 | 157 | 0.35 | 0.503 | 0.548 - 0.575 | Euploid |
| | AS897A | 1 | 198 | 8 | 87 | 111 | 0.17 | 0.439 | 0.532 - 0.579 | Euploid |
| | AS821A | 1 | 152 | 8 | 69 | 83 | 0.13 | 0.454 | 0.523 - 0.588 | Euploid |
| | AS980A | 1 | 394 | 137 | 191 | 203 | 0.59 | 0.485 | 0.561 - 0.580 | Euploid |
| | AS2262A | 1 | 334 | 342 | 177 | 157 | 1.06 | 0.530 | 0.550 - 0.597 | Euploid |
| | AS2425A | 1 | 128 | 8 | 64 | 64 | 0.10 | 0.500 | 0.518 - 0.591 | Euploid |
| | AS2434A | 1 | 379 | 97 | 203 | 176 | 0.44 | 0.500 | 0.555 - 0.575 | Euploid |
| | A1119 | 1 | 354 | 123 | 165 | 189 | 0.46 | 0.523 | 0.555 - 0.577 | Euploid |
| | A1122 | 1 | 369 | 100 | 195 | 174 | 0.44 | 0.528 | 0.554 - 0.576 | Euploid |
| | A1152 | 1 | 256 | 48 | 128 | 128 | 0.26 | 0.500 | 0.542 - 0.578 | Euploid |
| | A1180 | 1 | 246 | 499 | 133 | 113 | 1.61 | 0.541 | 0.604 - 0.622 | Euploid |
| | A1275 | 1 | 373 | 95 | 201 | 172 | 0.43 | 0.539 | 0.554 - 0.575 | Euploid |
| | A1375 | 1 | 359 | 55 | 190 | 169 | 0.35 | 0.529 | 0.550 - 0.573 | Euploid |
| | A1398 | 1 | 357 | 87 | 165 | 192 | 0.47 | 0.462 | 0.555 - 0.577 | Euploid |
| | A1399 | 1 | 371 | 114 | 197 | 174 | 0.47 | 0.531 | 0.556 - 0.577 | Euploid |

[a] no. of reference molecules per well
[b] $P_r$ values were calculated by the equation: $\dfrac{\text{no. of wells positive for the overrepresented allele (chr21)}}{\text{no. of wells positive for chr21 only + no. of wells positive for chr1 only}}$
[c] "Euploid" was assigned when the $P_r$ was below the unclassifiable region; "T21" was assigned when the $P_r$ was above the unclassifiable region.

FIG. 19

| Type | Cases | Total No. of panels used | Total No. of informative wells | No. of well count | | | $m_r^a$ | $P_r^b$ | SPRT analysis | |
|---|---|---|---|---|---|---|---|---|---|---|
| | | | | Both positive | Chr18 only | Chr21 only | | | Unclassifiable region | Classification[c] |
| Euploid | N0230 | 1 | 380 | 243 | 181 | 199 | 0.86 | 0.476 | 0.573 - 0.589 | E |
| | N0625 | 1 | 370 | 225 | 179 | 191 | 0.78 | 0.484 | 0.569 - 0.586 | E |
| | N0651 | 1 | 358 | 206 | 192 | 166 | 0.67 | 0.536 | 0.564 - 0.583 | E |
| T18 | N0828 | 1 | 543 | 256 | 329 | 214 | 0.95 | 0.606 | 0.579 - 0.590 | T18 |
| | N0830 | 1 | 346 | 353 | 240 | 106 | 0.92 | 0.694 | 0.574 - 0.592 | T18 |
| | N0936 | 1 | 372 | 285 | 209 | 163 | 0.88 | 0.562 | 0.573 - 0.590 | E |
| | N1678 | 1 | 343 | 115 | 221 | 122 | 0.37 | 0.644 | 0.551 - 0.574 | T18 |
| | N1701 | 1 | 303 | 94 | 191 | 112 | 0.31 | 0.630 | 0.546 - 0.575 | T18 |

[a] no. of reference molecules per well

[b] $P_r$ values were calcualated by the equation:

$$P_r = \frac{\text{no. of wells positive for the overrepresented allele (chr18)}}{\text{no. of wells positive for chr21 only} + \text{no. of wells positive for chr18 only}}$$

no. of wells positive for chr21 only + no of wells positive for chr18 only

[c] "Euploid" was assigned when the Pr was below the unclassifiable region; "T18" was assigned when the Pr was above the unclassifiable region.

FIG. 20

| Type | Cases | Plate No. | Assay | Total No. of informative wells | No. of well count | | | $m_r{}^a$ | $P_r{}^b$ | SPRT analysis | Classification$^c$ |
|---|---|---|---|---|---|---|---|---|---|---|---|
| | | | | | Both positive | Chr 21 only | Ref only | | | Unclassifiable region | |
| Normal | N0196 | 1 | chr21/chr1 | 148 | 78 | 71 | 77 | 0.52 | 0.480 | 0.489 - 0.584 | E |
| | | 1 | chr21/chr18 | 152 | 63 | 79 | 73 | 0.44 | 0.520 | 0.487 - 0.584 | U |
| | | | SUM | 300 | 141 | 150 | 150 | 0.48 | 0.500 | 0.512 - 0.560 | E |
| | N0198 | 1 | chr21/chr1 | 162 | 73 | 70 | 92 | 0.56 | 0.432 | 0.490 - 0.581 | E |
| | | 1 | chr21/chr18 | 183 | 68 | 93 | 90 | 0.53 | 0.508 | 0.498 - 0.575 | U |
| | | | SUM | 345 | 141 | 163 | 182 | 0.55 | 0.472 | 0.517 - 0.557 | E |
| | N0230 | 1 | chr21/chr1 | 162 | 58 | 81 | 81 | 0.45 | 0.500 | 0.490 - 0.581 | U |
| | | 1 | chr21/chr18 | 165 | 45 | 81 | 84 | 0.41 | 0.491 | 0.489 - 0.580 | U |
| | | | SUM | 327 | 103 | 162 | 165 | 0.43 | 0.495 | 0.512 - 0.558 | E |
| | N0231 | 1 | chr21/chr1 | 173 | 53 | 81 | 92 | 0.47 | 0.468 | 0.494 - 0.578 | E |
| | | 1 | chr21/chr18 | 166 | 51 | 85 | 81 | 0.42 | 0.512 | 0.490 - 0.580 | U |
| | | | SUM | 339 | 104 | 166 | 173 | 0.45 | 0.490 | 0.514 - 0.557 | E |
| | N0262 | 1 | chr21/chr1 | 186 | 97 | 101 | 85 | 0.64 | 0.543 | 0.503 - 0.575 | U |
| | | 1 | chr21/chr18 | 176 | 111 | 91 | 85 | 0.71 | 0.517 | 0.504 - 0.557 | U |
| | | | SUM | 362 | 208 | 192 | 170 | 0.68 | 0.530 | 0.522 - 0.557 | U |
| | | 2 | chr21/chr1 | 174 | 103 | 85 | 89 | 0.69 | 0.489 | 0.503 - 0.577 | E |
| | | | SUM | 536 | 311 | 277 | 259 | 0.68 | 0.517 | 0.523 - 0.552 | E |
| T21 | N0234 | 1 | chr21/chr1 | 193 | 68 | 108 | 85 | 0.51 | 0.560 | 0.500 - 0.573 | U |
| | | 1 | chr21/chr18 | 178 | 65 | 92 | 86 | 0.50 | 0.517 | 0.498 - 0.576 | U |
| | | | SUM | 371 | 133 | 200 | 171 | 0.50 | 0.539 | 0.517 - 0.556 | U |
| | | 2 | chr21/chr1 | 178 | 73 | 92 | 86 | 0.53 | 0.517 | 0.498 - 0.576 | U |
| | | | SUM | 549 | 206 | 292 | 257 | 0.51 | 0.532 | 0.524 - 0.549 | U |
| | | 2 | chr21/chr18 | 178 | 62 | 95 | 83 | 0.47 | 0.534 | 0.495 - 0.576 | U |
| | | | SUM | 727 | 268 | 387 | 340 | 0.50 | 0.532 | 0.527 - 0.546 | U |
| | | 3 | chr21/chr1 | 184 | 105 | 103 | 81 | 0.68 | 0.560 | 0.504 - 0.575 | U |
| | | | SUM | 911 | 376 | 490 | 421 | 0.54 | 0.538 | 0.529 - 0.545 | U |
| | | 3 | chr21/chr18 | 198 | 102 | 120 | 78 | 0.63 | 0.606 | 0.505 - 0.572 | T21 |
| | | | SUM | 1109 | 478 | 610 | 499 | 0.55 | 0.550 | 0.531 - 0.544 | T21 |
| | N0332 | 1 | chr21/chr1 | 173 | 109 | 103 | 70 | 0.63 | 0.595 | 0.500 - 0.577 | T21 |
| | | 1 | chr21/chr18 | 191 | 82 | 110 | 81 | 0.55 | 0.576 | 0.501 - 0.574 | T21 |
| | | | SUM | 364 | 191 | 213 | 151 | 0.59 | 0.585 | 0.519 - 0.557 | T21 |
| | N0349 | 1 | chr21/chr1 | 158 | 62 | 83 | 75 | 0.44 | 0.525 | 0.489 - 0.582 | U |
| | | 1 | chr21/chr18 | 166 | 46 | 87 | 79 | 0.39 | 0.524 | 0.489 - 0.580 | U |
| | | | SUM | 324 | 108 | 170 | 154 | 0.42 | 0.525 | 0.512 - 0.558 | U |
| | | 2 | chr21/chr1 | 149 | 66 | 86 | 63 | 0.41 | 0.577 | 0.485 - 0.585 | U |
| | | | SUM | 473 | 174 | 256 | 217 | 0.41 | 0.541 | 0.519 - 0.551 | U |
| | | 2 | chr21/chr18 | 168 | 43 | 100 | 68 | 0.34 | 0.595 | 0.487 - 0.580 | T21 |
| | | | SUM | 641 | 217 | 356 | 285 | 0.40 | 0.555 | 0.523 - 0.546 | T21 |
| | N0764 | 1 | chr21/chr1 | 182 | 82 | 106 | 76 | 0.53 | 0.582 | 0.498 - 0.575 | T21 |
| | | 1 | chr21/chr18 | 178 | 83 | 97 | 81 | 0.56 | 0.545 | 0.498 - 0.576 | U |
| | | | SUM | 360 | 165 | 203 | 157 | 0.54 | 0.564 | 0.518 - 0.556 | T21 |
| | N0890 | 1 | chr21/chr1 | 180 | 103 | 108 | 72 | 0.61 | 0.600 | 0.501 - 0.576 | T21 |
| | | 1 | chr21/chr18 | 188 | 68 | 104 | 84 | 0.50 | 0.553 | 0.489 - 0.574 | U |
| | | | SUM | 368 | 171 | 212 | 156 | 0.55 | 0.576 | 0.518 - 0.556 | T21 |

$^a$ no. of reference molecules per well
$^b$ $P_r$ values were calculated by the equation:

$$\frac{\text{no. of wells positive for the overrepresented allele (chr21)}}{\text{no. of wells positive for chr21 only + no. of wells positive for Ref only}}$$

$^c$ "Euploid" was assigned when the $P_r$ was below the unclassifiable region; "T21" was assigned when the $P_r$ was above the unclassifiable region.

FIG. 21

|  |  |  | Poisson corrected total no. |  | $P_r$ | Classification |
|---|---|---|---|---|---|---|
|  |  |  | Chromosome 21 | Reference chr |  |  |
| Euploid | Case 1 | Assay 1 | 37 | 33 | 0.52345751 | Unclass |
|  |  | Assay 2 | 31 | 42 | 0.42506276 | Unclass |
|  |  | Assay 3 | 29 | 37 | 0.44198785 | Unclass |
|  |  | Assay 4 | 39 | 26 | 0.6008691 | Unclass |
|  |  | Plate 1 subtotal | 136 | 138 | 0.495821 | Unclass |
|  |  | Assay 1 | 32 | 25 | 0.56605316 | Unclass |
|  |  | Assay 2 | 27 | 24 | 0.53165424 | Unclass |
|  |  | Assay 3 | 10 | 17 | 0.3681535 | Unclass |
|  |  | Assay 4 | 24 | 18 | 0.5626764 | Unclass |
|  |  | Plate 2 subtotal | 93 | 84 | 0.52474 | Unclass |
|  |  | Total | 229 | 223 | 0.507182 | Euploid |
|  | Case 2 | Assay 1 | 45 | 35 | 0.56321585 | Unclass |
|  |  | Assay 2 | 31 | 45 | 0.41245525 | Unclass |
|  |  | Assay 3 | 32 | 22 | 0.59954763 | Unclass |
|  |  | Assay 4 | 38 | 35 | 0.5228175 | Unclass |
|  |  | Plate 1 subtotal | 146 | 135 | 0.519153 | Unclass |
|  |  | Assay 1 | 28 | 23 | 0.55272135 | Unclass |
|  |  | Assay 2 | 23 | 22 | 0.51196923 | Unclass |
|  |  | Assay 3 | 23 | 15 | 0.59688187 | Unclass |
|  |  | Assay 4 | 29 | 26 | 0.5293349 | Unclass |
|  |  | Plate 2 subtotal | 102 | 85 | 0.545204 | Unclass |
|  |  | Plate 1+2 subtotal | 248 | 221 | 0.529583 | Unclass |
|  |  | Assay 1 | 17 | 25 | 0.4122149 | Unclass |
|  |  | Assay 2 | 25 | 16 | 0.6027299 | Unclass |
|  |  | Assay 3 | 13 | 26 | 0.3382802 | Unclass |
|  |  | Assay 4 | 27 | 24 | 0.5316872 | Unclass |
|  |  | Plate 3 subtotal | 82 | 91 | 0.475775 | Unclass |
|  |  | Plate 1- 3 subtotal | 331 | 311 | 0.515069 | Unclass |
|  |  | Assay 1 | 15 | 9 | 0.6269193 | Unclass |
|  |  | Assay 2 | 14 | 15 | 0.4824155 | Unclass |
|  |  | Assay 3 | 18 | 17 | 0.5146313 | Unclass |
|  |  | Assay 4 | 21 | 18 | 0.5270080 | Unclass |
|  |  | Plate 4 subtotal | 69 | 60 | 0.532264 | Unclass |
|  |  | Plate 1- 4 subtotal | 399 | 372 | 0.517942 | Unclass |

FIG. 22A

|  |  |  |  |  |  |
|---|---|---|---|---|---|
|  | Assay 1 | 10 | 13 | 0.4337957 | Unclass |
|  | Assay 2 | 11 | 14 | 0.4390082 | Unclass |
|  | Assay 3 | 7 | 16 | 0.3018022 | Unclass |
|  | Assay 4 | 19 | 10 | 0.6579085 | Unclass |
|  | Plate 5 subtotal | 48 | 54 | 0.469951 | Unclass |
|  | Total | 447 | 426 | 0.5123444 | Euploid |
| T21 |  |  |  |  |  |
| Case 3 | Assay 1 | 50 | 33 | 0.60012253 | Unclass |
|  | Assay 2 | 56 | 47 | 0.54458055 | Unclass |
|  | Assay 3 | 46 | 28 | 0.6196626 | Unclass |
|  | Assay 4 | 56 | 36 | 0.6108731 | Unclass |
|  | Total | 208 | 144 | 0.59079 | T21 |
| Case 4 | Assay 1 | 56 | 36 | 0.61085513 | Unclass |
|  | Assay 2 | 38 | 32 | 0.53906912 | Unclass |
|  | Assay 3 | 40 | 24 | 0.62788068 | Unclass |
|  | Assay 4 | 47 | 27 | 0.634511 | Unclass |
|  | Total | 180 | 119 | 0.603476 | T21 |

FIG. 22B

| Cases | Samples | Expected % | No of panels | ZFY | ZFX | ALL POS | NET ZFY | NET ZFX | Ref allele | $m_r$ | SPRT[a] |
|---|---|---|---|---|---|---|---|---|---|---|---|
| 1 | XY + XX | 50% | 1 | 239 | 465 | 155 | 84 | 310 | Y | 0.37 | XX |
|  | (XX %) | 25% | 1 | 328 | 447 | 205 | 123 | 242 | Y | 0.56 | XX |
| 2 | XY$_1$ + XY$_2$ | 50% | 1 | 414 | 405 | 220 | 194 | 185 | X | 0.85 | XY |
|  | (XY$_2$ %) | 25% | 1 | 432 | 426 | 245 | 187 | 181 | X | 0.81 | XY |

FIG. 24A

| Cases | No of panels | ZFY | ZFX | ALL POS | NET ZFY | NET ZFX | Ref allele | $m_r$ | SPRT |
|---|---|---|---|---|---|---|---|---|---|
| 1 | 1 | 81 | 171 | 18 | 63 | 153 | Y | 0.11 | XX |
| 2 | 1 | 103 | 175 | 23 | 80 | 152 | Y | 0.14 | XX |
| 3 | 1 | 110 | 175 | 28 | 82 | 147 | Y | 0.16 | XX |
| 4 | 1 | 111 | 156 | 24 | 87 | 132 | Y | 0.16 | XX |
| 5 | 2 | 236 | 322 | 50 | 186 | 272 | Y | 0.17 | XX |
| 6 | 1 | 116 | 184 | 29 | 87 | 155 | Y | 0.16 | XX |
| 7 | 1 | 94 | 169 | 19 | 75 | 150 | Y | 0.13 | XX |
| 8 | 1 | 91 | 155 | 24 | 67 | 131 | Y | 0.13 | XX |
| 9 | 3 | 333 | 447 | 74 | 259 | 373 | Y | 0.16 | XX |
| 10 | 1 | 110 | 154 | 24 | 86 | 130 | Y | 0.16 | XX |
| 11 | 1 | 83 | 170 | 26 | 57 | 144 | Y | 0.11 | XX |
| 12 | 1 | 85 | 159 | 16 | 69 | 143 | Y | 0.12 | XX |

FIG. 24B

| Cases | No of panels | Maternal genotype[a] | Fetal genotype[a] | Expected fetal % | A | G | ALL POS | NET A | NET G | Actual fetal %[b] | Ref allele | $m_r$ | SPRT[d] |
|---|---|---|---|---|---|---|---|---|---|---|---|---|---|
| 1 | 1 | AG | GG | 15% | 264 | 318 | 116 | 148 | 202 | 9.6 | A | 0.42 | GG |
| 2 | 1 | AG | GG | 15% | 208 | 276 | 81 | 127 | 195 | 14.3 | A | 0.32 | GG |
| 3 | 1 | AG | AG | 15% | 248 | 251 | 87 | 161 | 164 | 15.4 | A | 0.39 | AG |
| 4 | 1 | AG | GG | 15% | 158 | 240 | 51 | 107 | 189 | 13.7 | A | 0.23 | GG |
| 5 | 1 | AG | AG | 15% | 226 | 245 | 70 | 156 | 175 | 16.8 | A | 0.35 | AG |
| 6 | 1 | AG | AG | 15% | 319 | 319 | 130 | 189 | 189 | 18.1 | A | 0.54 | AG |
| 7 | 1 | AG | AG | 15% | 254 | 279 | 94 | 160 | 185 | 19.8 | A | 0.40 | AG |
| 8 | 1 | AG | GG | 15% | 296 | 363 | 144 | 152 | 219 | 15.7 | A | 0.49 | GG |
| 9 | 1 | AG | AG | 15% | 279 | 285 | 100 | 179 | 185 | 13.0 | A | 0.45 | AG |
| 10 | 1 | AG | AA | 15% | 337 | 278 | 120 | 217 | 158 | NA[c] | G | 0.45 | AA |
| 1 | 1 | AG | GG | 20% | 248 | 295 | 96 | 152 | 199 | 13.0 | A | 0.39 | GG |
| 2 | 1 | AG | GG | 20% | 191 | 289 | 79 | 112 | 210 | 19.5 | A | 0.29 | GG |
| 3 | 1 | AG | AG | 20% | 248 | 218 | 75 | 173 | 143 | 18.2 | G | 0.34 | U |
| 4 | 1 | AG | GG | 20% | 158 | 257 | 59 | 99 | 198 | 25.9 | A | 0.23 | GG |
| 5 | 1 | AG | AG | 20% | 231 | 215 | 71 | 160 | 144 | 20.3 | G | 0.33 | AG |
| 6 | 1 | AG | AG | 20% | 281 | 283 | 98 | 183 | 185 | 26.3 | A | 0.46 | AG |
| 7 | 1 | AG | AG | 20% | 256 | 231 | 88 | 168 | 143 | 22.7 | G | 0.36 | AG |
| 8 | 1 | AG | GG | 20% | 246 | 311 | 104 | 142 | 207 | 23.0 | A | 0.39 | GG |
| 9 | 1 | AG | AG | 20% | 267 | 249 | 83 | 184 | 166 | 21.9 | G | 0.39 | AG |
| 10 | 1 | AG | AA | 20% | 303 | 203 | 77 | 226 | 126 | NA[c] | G | 0.31 | AA |
| 1 | 1 | AG | GG | 25% | 244 | 304 | 99 | 145 | 205 | 15.7 | A | 0.38 | GG |
| 2 | 1 | AG | GG | 25% | 209 | 314 | 88 | 121 | 226 | 24.9 | A | 0.32 | GG |
| 3 | 1 | AG | AG | 25% | 204 | 212 | 55 | 149 | 157 | 28.0 | A | 0.31 | AG |
| 4 | 1 | AG | GG | 25% | 185 | 290 | 76 | 109 | 214 | 25.9 | A | 0.28 | GG |
| 5 | 1 | AG | AG | 25% | 233 | 243 | 77 | 156 | 166 | 24.5 | A | 0.36 | AG |
| 6 | 1 | AG | AG | 25% | 292 | 305 | 110 | 182 | 195 | 27.3 | A | 0.48 | AG |
| 7 | 1 | AG | AG | 25% | 261 | 275 | 95 | 166 | 180 | 22.5 | A | 0.42 | AG |
| 8 | 1 | AG | GG | 25% | 236 | 327 | 96 | 140 | 231 | 26.7 | A | 0.37 | GG |
| 9 | 1 | AG | AG | 25% | 271 | 280 | 104 | 167 | 176 | 25.2 | A | 0.44 | AG |
| 10 | 1 | AG | AA | 25% | 243 | 154 | 46 | 197 | 108 | NA[c] | G | 0.22 | AA |
| 1 | 1 | AG | GG | 50% | 136 | 293 | 57 | 79 | 236 | 33.6 | A | 0.20 | GG |
| 2 | 1 | AG | GG | 50% | 163 | 358 | 78 | 85 | 280 | 45.8 | A | 0.24 | GG |
| 3 | 1 | AG | AG | 50% | 200 | 208 | 53 | 147 | 155 | 55.7 | A | 0.30 | AG |
| 4 | 1 | AG | GG | 50% | 137 | 356 | 66 | 71 | 290 | 53.0 | A | 0.18 | GG |
| 5 | 1 | AG | AG | 50% | 247 | 246 | 91 | 156 | 155 | 57.7 | G | 0.39 | AG |
| 6 | 1 | AG | AG | 50% | 218 | 245 | 68 | 150 | 177 | 53.8 | A | 0.34 | AG |
| 7 | 1 | AG | AG | 50% | 255 | 282 | 103 | 152 | 179 | 51.3 | A | 0.41 | AG |
| 8 | 1 | AG | GG | 50% | 158 | 398 | 83 | 75 | 315 | 57.6 | A | 0.23 | GG |
| 9 | 1 | AG | AG | 50% | 235 | 225 | 74 | 161 | 151 | 55.7 | G | 0.35 | AG |
| 10 | 1 | AG | AA | 50% | 317 | 106 | 35 | 282 | 71 | NA[c] | G | 0.15 | AA |

[a] A = Mutated allele, G = Wildtype allele.
[b] The actual fetal DNA % is determined by the digital ZFY/X assay.
[c] The fetus is female and digital ZFY/X assay cannot be applied.
[d] SPRT was done with the fetal % determined by the digital ZFY/X assay except case 10; U, unclassified.

| Case | Maternal genotype[a] | Fetal genotype[a] | No of panels | M | N | ALL POS | NET M | NET N | Expected fetal % | SPRT | Fetal % by digital ZFY/X | SPRT | Ref Allele | $m_r$ |
|---|---|---|---|---|---|---|---|---|---|---|---|---|---|---|
| 1 | MN | MM | 3 | 846 | 763 | 273 | 573 | 490 | 5% | MM | 7.8% | MM | N | 0.40 |
|  | MN | MM | 3 | 863 | 748 | 289 | 574 | 459 | 10% | MM | 9.6% | MM | N | 0.39 |
|  | MN | MM | 1 | 323 | 219 | 79 | 244 | 140 | 25% | MM | 24.1% | MM | N | 0.34 |
|  | MN | MM | 1 | 418 | 160 | 92 | 326 | 68 | 50% | MM | 57.2% | MM | N | 0.23 |
| 2 | MN | MN | 9 | 2559 | 2476 | 887 | 1672 | 1589 | 5% | U | 3.4% | U | N | 0.45 |
|  | MN | MN | 3 | 895 | 907 | 360 | 535 | 547 | 10% | MN | 9.7% | MN | M | 0.49 |
|  | MN | MN | 1 | 277 | 263 | 97 | 180 | 166 | 25% | MN | 24.2% | MN | N | 0.42 |
|  | MN | MN | 1 | 273 | 295 | 101 | 172 | 194 | 50% | MN | 58.0% | MN | M | 0.44 |

[a] M = with CTTT deletion, N = without CTTT deletion.
[b] SPRT was done with the expected %.
[c] SPRT was done with the fetal % determined by the digital ZFY/X assay; U, unclassified.

| Cases | Maternal genotype[a] | Fetal genotype[a] | No of panels | M | N | ALL POS | NET M | NET N | Actual fetal %[b] | SPRT | Ref allele | $m_r$ | SPRT[c] |
|---|---|---|---|---|---|---|---|---|---|---|---|---|---|
| 1 | MN | MN | 1 | 203 | 200 | 58 | 145 | 142 | 29.0 | MN | N | 0.30 | MN |
| 2 | MN | MN | 1 | 149 | 204 | 39 | 110 | 165 | 29.7 | MN | M | 0.22 | NN |
| 3 | MN | NN | 1 | 128 | 212 | 31 | 97 | 181 | 30.7 | NN | M | 0.18 | NN |
| 4 | MN | MN | 1 | 173 | 196 | 45 | 128 | 151 | 27.0 | MN | M | 0.26 | MN |
| 5 | MN | MN | 1 | 147 | 230 | 47 | 100 | 183 | 24.3 | MN | M | 0.21 | NN |
| 6 | MN | NN | 1 | 199 | 206 | 45 | 154 | 161 | 19.2 | NN | M | 0.30 | MN |
| 7 | MN | MN | 1 | 165 | 237 | 58 | 107 | 179 | 18.7 | MN | N | 0.24 | NN |
| 8 | MN | MN | 1 | 203 | 180 | 43 | 160 | 137 | 23.4 | MN | M | 0.27 | MN |
| 9 | MN | MN | 1 | 173 | 241 | 61 | 112 | 180 | 16.9 | MN | M | 0.26 | NN |
| 10 | MN | MN | 1 | 174 | 190 | 52 | 122 | 138 | 16.8 | MN | M | 0.26 | U |
| 11 | MN | NN | 1 | 167 | 242 | 49 | 118 | 193 | 17.7 | NN | M | 0.25 | NN |
| 12 | MN | MN | 1 | 213 | 199 | 47 | 166 | 152 | 21.6 | MN | N | 0.30 | MN |

[a] M = with CTTT deletion, N = without CTTT deletion.
[b] The actual fetal DNA % is determined by the digital ZFY/X assay.
[c] SPRT was done with the fetal % determined by the digital ZFY/X assay; U, unclassified.

FIG. 26B

SEQUENCE LISTING

<160> NUMBER OF SEQ ID NOS: 58

<210> SEQ ID NO 1
<211> LENGTH: 27
<212> TYPE: DNA

<213> ORGANISM: Artificial Sequence
<220> FEATURE:
<223> OTHER INFORMATION: synthetic real-time PCR and digital RNA-SNP
    analysis PLAC4 gene-specific reverse transcription primer

<400> SEQUENCE: 1
agtatataga accatgttta ggccaga                                         27

<210> SEQ ID NO 2
<211> LENGTH: 21
<212> TYPE: DNA
<213> ORGANISM: Artificial Sequence
<220> FEATURE:
<223> OTHER INFORMATION: synthetic real-time PCR PLAC4 primer

<400> SEQUENCE: 2
ccgctagggt gtcttttaag c                                               21

<210> SEQ ID NO 3
<211> LENGTH: 25
<212> TYPE: DNA
<213> ORGANISM: Artificial Sequence
<220> FEATURE:
<223> OTHER INFORMATION: synthetic real-time PCR PLAC4 primer

<400> SEQUENCE: 3
gtgttgcaat acaaaatgag tttct                                           25

<210> SEQ ID NO 4
<211> LENGTH: 14
<212> TYPE: DNA
<213> ORGANISM: Artificial Sequence
<220> FEATURE:
<223> OTHER INFORMATION: synthetic real-time PCR PLAC4 fluorescent probe
<220> FEATURE:
<221> NAME/KEY: modified_base
<222> LOCATION: (1)...(1)
<223> OTHER INFORMATION: a modified by 6-carboxyfluorescein (FAM)
<220> FEATURE:
<221> NAME/KEY: modified_base
<222> LOCATION: (14)...(14)
<223> OTHER INFORMATION: c modified by minor groove binding
    non-fluorescent quencher (MGBNFQ)

<400> SEQUENCE: 4
attggagcaa attc                                                       14

<210> SEQ ID NO 5
<211> LENGTH: 104
<212> TYPE: DNA
<213> ORGANISM: Artificial Sequence
<220> FEATURE:
<223> OTHER INFORMATION: single-stranded synthetic DNA oligonucleotide
    amplicon

<400> SEQUENCE: 5
cgccgctagg gtgtctttta agctattgga gcaaattcaa atttggctta aagaaaaaga    60
aactcatttt gtattgcaac accaggagta tcccaaggga ctcg                    104

<210> SEQ ID NO 6
<211> LENGTH: 22
<212> TYPE: DNA
<213> ORGANISM: Artificial Sequence
<220> FEATURE:
<223> OTHER INFORMATION: synthetic digital RNA-SNP analysis non-intron
    spanning forward primer

<400> SEQUENCE: 6
tttgtattgc aacaccattt gg                                                22

<210> SEQ ID NO 7
<211> LENGTH: 15
<212> TYPE: DNA
<213> ORGANISM: Artificial Sequence
<220> FEATURE:
<223> OTHER INFORMATION: synthetic allele-G-specific TaqMan probe
      targeting rs8130833 SNP of PLAC4
<220> FEATURE:
<221> NAME/KEY: modified_base
<222> LOCATION: (1)...(1)
<223> OTHER INFORMATION: t modified by 6-carboxyfluorescein (FAM)
<220> FEATURE:
<221> NAME/KEY: modified_base
<222> LOCATION: (15)...(15)
<223> OTHER INFORMATION: g modified by minor groove binding
      non-fluorescent quencher (MGBNFQ)

<400> SEQUENCE: 7
tcgtcgtcta acttg                                                        15

<210> SEQ ID NO 8
<211> LENGTH: 17
<212> TYPE: DNA
<213> ORGANISM: Artificial Sequence
<220> FEATURE:
<223> OTHER INFORMATION: synthetic allele-A-specific TaqMan probe
      targeting rs8130833 SNP of PLAC4
<220> FEATURE:
<221> NAME/KEY: modified_base
<222> LOCATION: (1)...(1)
<223> OTHER INFORMATION: a modified by fluorescent reporter VIC
<220> FEATURE:
<221> NAME/KEY: modified_base
<222> LOCATION: (17)...(17)
<223> OTHER INFORMATION: g modified by minor groove binding
      non-fluorescent quencher (MGBNFQ)

<400> SEQUENCE: 8
attcgtcatc taacttg                                                      17

<210> SEQ ID NO 9
<211> LENGTH: 23
<212> TYPE: DNA
<213> ORGANISM: Artificial Sequence
<220> FEATURE:
<223> OTHER INFORMATION: synthetic digital RCD analysis co-amplification
      forward primer for paralogous loci on chromosome
      21 and 1

<400> SEQUENCE: 9
gttgttctgc aaaaaacctt cga                                               23

<210> SEQ ID NO 10
<211> LENGTH: 28
<212> TYPE: DNA
<213> ORGANISM: Artificial Sequence
<220> FEATURE:
<223> OTHER INFORMATION: synthetic digital RCD analysis co-amplification
      reverse primer for paralogous loci on chromosome
      21 and 1

<400> SEQUENCE: 10
cttggccaga aatacttcat taccatat                                          28

<210> SEQ ID NO 11
<211> LENGTH: 19
<212> TYPE: DNA

<213> ORGANISM: Artificial Sequence
<220> FEATURE:
<223> OTHER INFORMATION: synthetic chromosome-specific TaqMan probe designed to target chromosome 21 paralog
<220> FEATURE:
<221> NAME/KEY: modified_base
<222> LOCATION: (1)...(1)
<223> OTHER INFORMATION: t modified by 6-carboxyfluorescein (FAM)
<220> FEATURE:
<221> NAME/KEY: modified_base
<222> LOCATION: (19)...(19)
<223> OTHER INFORMATION: a modified by minor groove binding non-fluorescent quencher (MGBNFQ)

<400> SEQUENCE: 11
tacctccata atgagtaaa                                              19

<210> SEQ ID NO 12
<211> LENGTH: 20
<212> TYPE: DNA
<213> ORGANISM: Artificial Sequence
<220> FEATURE:
<223> OTHER INFORMATION: synthetic chromosome-specific TaqMan probe designed to target chromosome 1 paralog
<220> FEATURE:
<221> NAME/KEY: modified_base
<222> LOCATION: (1)...(1)
<223> OTHER INFORMATION: c modified by fluorescent reporter VIC
<220> FEATURE:
<221> NAME/KEY: modified_base
<222> LOCATION: (20)...(20)
<223> OTHER INFORMATION: a modified by minor groove binding non-fluorescent quencher (MGBNFQ)

<400> SEQUENCE: 12
cgtacctctg taatgtgtaa                                             20

<210> SEQ ID NO 13
<211> LENGTH: 27
<212> TYPE: DNA
<213> ORGANISM: Artificial Sequence
<220> FEATURE:
<223> OTHER INFORMATION: synthetic digital PCR PLAC4 gene-specific reverse transcription primer

<400> SEQUENCE: 13
agtatataga accatgttta ggccaga                                     27

<210> SEQ ID NO 14
<211> LENGTH: 22
<212> TYPE: DNA
<213> ORGANISM: Artificial Sequence
<220> FEATURE:
<223> OTHER INFORMATION: synthetic digital PCR amplification forward primer for rs8130833 SNP region of PLAC4 gene

<400> SEQUENCE: 14
tttgtattgc aacaccattt gg                                          22

<210> SEQ ID NO 15
<211> LENGTH: 15
<212> TYPE: DNA
<213> ORGANISM: Artificial Sequence
<220> FEATURE:
<223> OTHER INFORMATION: synthetic allele-G-specific TaqMan probe targeting PLAC4 rs8130833 SNP
<220> FEATURE:
<221> NAME/KEY: modified_base
<222> LOCATION: (1)...(1)
<223> OTHER INFORMATION: t modified by 6-carboxyfluorescein (FAM)
<220> FEATURE:

<221> NAME/KEY: modified_base
<222> LOCATION: (15)...(15)
<223> OTHER INFORMATION: g modified by minor groove binding
      non-fluorescent quencher (MGBNFQ)

<400> SEQUENCE: 15
tcgtcgtcta acttg                                                    15

<210> SEQ ID NO 16
<211> LENGTH: 17
<212> TYPE: DNA
<213> ORGANISM: Artificial Sequence
<220> FEATURE:
<223> OTHER INFORMATION: synthetic allele-A-specific TaqMan probe
      targeting PLAC4 rs8130833 SNP
<220> FEATURE:
<221> NAME/KEY: modified_base
<222> LOCATION: (1)...(1)
<223> OTHER INFORMATION: a modified by fluorescent reporter VIC
<220> FEATURE:
<221> NAME/KEY: modified_base
<222> LOCATION: (17)...(17)
<223> OTHER INFORMATION: g modified by minor groove binding
      non-fluorescent quencher (MGBNFQ)

<400> SEQUENCE: 16
attcgtcatc taacttg                                                  17

<210> SEQ ID NO 17
<211> LENGTH: 20
<212> TYPE: DNA
<213> ORGANISM: Artificial Sequence
<220> FEATURE:
<223> OTHER INFORMATION: synthetic digital PCR amplification serpin
      peptidase inhibitor clade B (ovalbumin) member 2
      (SERPINB2) gene-specific reverse transcription
      primer

<400> SEQUENCE: 17
cgcagacttc tcaccaaaca                                               20

<210> SEQ ID NO 18
<211> LENGTH: 20
<212> TYPE: DNA
<213> ORGANISM: Artificial Sequence
<220> FEATURE:
<223> OTHER INFORMATION: synthetic digital PCR amplification serpin
      peptidase inhibitor clade B (ovalbumin) member 2
      (SERPINB2) forward primer

<400> SEQUENCE: 18
ctcagctctg caatcaatgc                                               20

<210> SEQ ID NO 19
<211> LENGTH: 16
<212> TYPE: DNA
<213> ORGANISM: Artificial Sequence
<220> FEATURE:
<223> OTHER INFORMATION: synthetic allele-A-specific TaqMan probe
      targeting serpin peptidase inhibitor clade B (ovalbumin)
      member 2 (SERPINB2) rs6098 SNP
<220> FEATURE:
<221> NAME/KEY: modified_base
<222> LOCATION: (1)...(1)
<223> OTHER INFORMATION: c modified by 6-carboxyfluorescein (FAM)
<220> FEATURE:
<221> NAME/KEY: modified_base
<222> LOCATION: (16)...(16)
<223> OTHER INFORMATION: t modified by minor groove binding
      non-fluorescent quencher (MGBNFQ)

```
<400> SEQUENCE: 19
ccacagggaa ttattt                                                      16

<210> SEQ ID NO 20
<211> LENGTH: 16
<212> TYPE: DNA
<213> ORGANISM: Artificial Sequence
<220> FEATURE:
<223> OTHER INFORMATION: synthetic allele-G-specific TaqMan probe
      targeting serpin peptidase inhibitor clade B (ovalbumin)
      member 2 (SERPINB2) rs6098 SNP
<220> FEATURE:
<221> NAME/KEY: modified_base
<222> LOCATION: (1)...(1)
<223> OTHER INFORMATION: c modified by fluorescent reporter VIC
<220> FEATURE:
<221> NAME/KEY: modified_base
<222> LOCATION: (16)...(16)
<223> OTHER INFORMATION: t modified by minor groove binding
      non-fluorescent quencher (MGBNFQ)

<400> SEQUENCE: 20 ccacaggga ttattt                                                       16

<210> SEQ ID NO 21
<211> LENGTH: 23
<212> TYPE: DNA
<213> ORGANISM: Artificial Sequence
<220> FEATURE:
<223> OTHER INFORMATION: synthetic digital PCR analysis co-amplification
      forward primer for 101-bp amplicon for paralogous
      loci on chromosome 21 and 1

<400> SEQUENCE: 21
gttgttctgc aaaaaacctt cga                                              23

<210> SEQ ID NO 22
<211> LENGTH: 28
<212> TYPE: DNA
<213> ORGANISM: Artificial Sequence
<220> FEATURE:
<223> OTHER INFORMATION: synthetic digital PCR analysis co-amplification
      reverse primer for 101-bp amplicon for paralogous
      loci on chromosome 21 and 1

<400> SEQUENCE: 22
cttggccaga aatacttcat taccatat                                         28

<210> SEQ ID NO 23
<211> LENGTH: 19
<212> TYPE: DNA
<213> ORGANISM: Artificial Sequence
<220> FEATURE:
<223> OTHER INFORMATION: synthetic chromosome-specific TaqMan probe
      designed to target chromosome 21 paralog
<220> FEATURE:
<221> NAME/KEY: modified_base
<222> LOCATION: (1)...(1)
<223> OTHER INFORMATION: t modified by 6-carboxyfluorescein (FAM)
<220> FEATURE:
<221> NAME/KEY: modified_base
<222> LOCATION: (19)...(19)
<223> OTHER INFORMATION: a modified by minor groove binding
      non-fluorescent quencher (MGBNFQ)

<400> SEQUENCE: 23
tacctccata atgagtaaa                                                   19

<210> SEQ ID NO 24
```

```
<211> LENGTH: 20
<212> TYPE: DNA
<213> ORGANISM: Artificial Sequence
<220> FEATURE:
<223> OTHER INFORMATION: synthetic chromosome-specific TaqMan probe
      designed to target chromosome 1 paralog
<220> FEATURE:
<221> NAME/KEY: modified_base
<222> LOCATION: (1)...(1)
<223> OTHER INFORMATION: c modified by fluorescent reporter VIC
<220> FEATURE:
<221> NAME/KEY: modified_base
<222> LOCATION: (20)...(20)
<223> OTHER INFORMATION: a modified by minor groove binding
      non-fluorescent quencher (MGBNFQ)

<400> SEQUENCE: 24
cgtacctctg taatgtgtaa                                            20

<210> SEQ ID NO 25
<211> LENGTH: 24
<212> TYPE: DNA
<213> ORGANISM: Artificial Sequence
<220> FEATURE:
<223> OTHER INFORMATION: synthetic digital RCD analysis co-amplification
      forward primer for 128-bp amplicon for paralogous
      loci on chromosome 21 and 18

<400> SEQUENCE: 25
gtacagaaac cacaaactga tcgg                                       24

<210> SEQ ID NO 26
<211> LENGTH: 17
<212> TYPE: DNA
<213> ORGANISM: Artificial Sequence
<220> FEATURE:
<223> OTHER INFORMATION: synthetic digital RCD analysis co-amplification
      reverse primer for 128-bp amplicon for paralogous
      loci on chromosome 21 and 18

<400> SEQUENCE: 26
gtccaggctg tgggcct                                               17

<210> SEQ ID NO 27
<211> LENGTH: 14
<212> TYPE: DNA
<213> ORGANISM: Artificial Sequence
<220> FEATURE:
<223> OTHER INFORMATION: synthetic chromosome-specific TaqMan probe
      designed to target chromosome 21 paralog
<220> FEATURE:
<221> NAME/KEY: modified_base
<222> LOCATION: (1)...(1)
<223> OTHER INFORMATION: a modified by 6-carboxyfluorescein (FAM)
<220> FEATURE:
<221> NAME/KEY: modified_base
<222> LOCATION: (14)...(14)
<223> OTHER INFORMATION: a modified by minor groove binding
      non-fluorescent quencher (MGBNFQ)

<400> SEQUENCE: 27
aagaggcgag gcaa                                                  14

<210> SEQ ID NO 28
<211> LENGTH: 15
<212> TYPE: DNA
<213> ORGANISM: Artificial Sequence
<220> FEATURE:
<223> OTHER INFORMATION: synthetic chromosome-specific TaqMan probe
      designed to target chromosome 18 paralog
<220> FEATURE:
```

```
<221> NAME/KEY: modified_base
<222> LOCATION: (1)...(1)
<223> OTHER INFORMATION: a modified by fluorescent reporter VIC
<220> FEATURE:
<221> NAME/KEY: modified_base
<222> LOCATION: (15)...(15)
<223> OTHER INFORMATION: c modified by minor groove binding
      non-fluorescent quencher (MGBNFQ)

<400> SEQUENCE: 28
aagaggacag gcaac                                                          15

<210> SEQ ID NO 29
<211> LENGTH: 33
<212> TYPE: DNA
<213> ORGANISM: Artificial Sequence
<220> FEATURE:
<223> OTHER INFORMATION: synthetic digital PCR analysis co-amplification
      forward primer for 121-bp amplicon for paralogous
      loci on chromosome 21 and 1

<400> SEQUENCE: 29
acgttggatg gttgttctgc aaaaaaacctt cga                                     33

<210> SEQ ID NO 30
<211> LENGTH: 38
<212> TYPE: DNA
<213> ORGANISM: Artificial Sequence
<220> FEATURE:
<223> OTHER INFORMATION: synthetic digital PCR analysis co-amplification
      reverse primer for 121-bp amplicon for paralogous
      loci on chromosome 21 and 1

<400> SEQUENCE: 30
acgttggatg cttggccaga aatacttcat taccatat                                 38

<210> SEQ ID NO 31
<211> LENGTH: 21
<212> TYPE: DNA
<213> ORGANISM: Artificial Sequence
<220> FEATURE:
<223> OTHER INFORMATION: synthetic digital PCR analysis co-amplification
      extension primer for 121-bp amplicon for
      paralogous loci on chromosome 21 and 1

<400> SEQUENCE: 31
ctcatcctca cttcgtacct c                                                   21

<210> SEQ ID NO 32
<211> LENGTH: 34
<212> TYPE: DNA
<213> ORGANISM: Artificial Sequence
<220> FEATURE:
<223> OTHER INFORMATION: synthetic digital RCD analysis co-amplification
      forward primer for 148-bp amplicon for paralogous
      loci on chromosome 21 and 18

<400> SEQUENCE: 32
acgttggatg gtacagaaac cacaaactga tcgg                                     34

<210> SEQ ID NO 33
<211> LENGTH: 27
<212> TYPE: DNA
<213> ORGANISM: Artificial Sequence
<220> FEATURE:
<223> OTHER INFORMATION: synthetic digital RCD analysis co-amplification
      reverse primer for 148-bp amplicon for paralogous
      loci on chromosome 21 and 18
```

```
<400> SEQUENCE: 33
acgttggatg gtccaggctg tgggcct                                          27

<210> SEQ ID NO 34
<211> LENGTH: 17
<212> TYPE: DNA
<213> ORGANISM: Artificial Sequence
<220> FEATURE:
<223> OTHER INFORMATION: synthetic digital RCD analysis co-amplification
      extension primer for 148-bp amplicon for
      paralogous loci on chromosome 21 and 18

<400> SEQUENCE: 34
acaaaagggg gaagagg                                                     17

<210> SEQ ID NO 35
<211> LENGTH: 35
<212> TYPE: DNA
<213> ORGANISM: Artificial Sequence
<220> FEATURE:
<223> OTHER INFORMATION: synthetic digital RCD analysis co-amplification
      forward primer for 81 bp amplicon for paralogous
      loci on chromosome 21 and 1

<400> SEQUENCE: 35
acgttggatg ttgatgaagt ctcatctcta cttcg                                 35

<210> SEQ ID NO 36
<211> LENGTH: 33
<212> TYPE: DNA
<213> ORGANISM: Artificial Sequence
<220> FEATURE:
<223> OTHER INFORMATION: synthetic digital RCD analysis co-amplification
      reverse primer for 81 bp amplicon for paralogous
      loci on chromosome 21 and 1

<400> SEQUENCE: 36
acgttggatg caataagctt ggccagaaat act                                   33

<210> SEQ ID NO 37
<211> LENGTH: 37
<212> TYPE: DNA
<213> ORGANISM: Artificial Sequence
<220> FEATURE:
<223> OTHER INFORMATION: synthetic digital RCD analysis co-amplification
      forward primer for 82 bp amplicon for paralogous
      loci on chromosome 21 and 7

<400> SEQUENCE: 37
acgttggatg gaatttaagc taaatcagcc tgaactg                               37

<210> SEQ ID NO 38
<211> LENGTH: 37
<212> TYPE: DNA
<213> ORGANISM: Artificial Sequence
<220> FEATURE:
<223> OTHER INFORMATION: synthetic digital RCD analysis co-amplification
      reverse primer for 82 bp amplicon for paralogous
      loci on chromosome 21 and 7

<400> SEQUENCE: 38
acgttggatg gtttctcata gttcatcgta ggcttat                               37

<210> SEQ ID NO 39
<211> LENGTH: 30
<212> TYPE: DNA
<213> ORGANISM: Artificial Sequence
```

```
<220> FEATURE:
<223> OTHER INFORMATION: synthetic digital RCD analysis co-amplification
      forward primer for 101 bp amplicon for paralogous
      loci on chromosome 21 and 2

<400> SEQUENCE: 39
acgttggatg tcaggcaggg ttctatgcag                                    30

<210> SEQ ID NO 40
<211> LENGTH: 30
<212> TYPE: DNA
<213> ORGANISM: Artificial Sequence
<220> FEATURE:
<223> OTHER INFORMATION: synthetic digital RCD analysis co-amplification
      reverse primer for 101 bp amplicon for paralogous
      loci on chromosome 21 and 2

<400> SEQUENCE: 40
acgttggatg aggcggcttc ctggctcttg                                    30

<210> SEQ ID NO 41
<211> LENGTH: 31
<212> TYPE: DNA
<213> ORGANISM: Artificial Sequence
<220> FEATURE:
<223> OTHER INFORMATION: synthetic digital RCD analysis co-amplification
      forward primer for 102 bp amplicon for paralogous
      loci on chromosome 21 and 6

<400> SEQUENCE: 41
acgttggatg gctcgtctca ggctcgtagt t                                  31

<210> SEQ ID NO 42
<211> LENGTH: 30
<212> TYPE: DNA
<213> ORGANISM: Artificial Sequence
<220> FEATURE:
<223> OTHER INFORMATION: synthetic digital RCD analysis co-amplification
      reverse primer for 102 bp amplicon for paralogous
      loci on chromosome 21 and 6

<400> SEQUENCE: 42
acgttggatg tttcttcgag cccttcttgg                                    30

<210> SEQ ID NO 43
<211> LENGTH: 23
<212> TYPE: DNA
<213> ORGANISM: Artificial Sequence
<220> FEATURE:
<223> OTHER INFORMATION: synthetic extension primer for paralogous
      sequence mismatches (PSM) on paralogous loci on chromosomes
      21 and 1

<400> SEQUENCE: 43
gtctcatctc tacttcgtac ctc                                           23

<210> SEQ ID NO 44
<211> LENGTH: 19
<212> TYPE: DNA
<213> ORGANISM: Artificial Sequence
<220> FEATURE:
<223> OTHER INFORMATION: synthetic extension primer for paralogous
      sequence mismatches (PSM) on paralogous loci on chromosomes
      21 and 7

<400> SEQUENCE: 44
ttttacgctg tccccattt                                                19
```

<210> SEQ ID NO 45
<211> LENGTH: 19
<212> TYPE: DNA
<213> ORGANISM: Artificial Sequence
<220> FEATURE:
<223> OTHER INFORMATION: synthetic extension primer for paralogous
      sequence mismatches (PSM) on paralogous loci on chromosomes
      21 and 2

<400> SEQUENCE: 45
ggtctatgca ggagccgac                                              19

<210> SEQ ID NO 46
<211> LENGTH: 25
<212> TYPE: DNA
<213> ORGANISM: Artificial Sequence
<220> FEATURE:
<223> OTHER INFORMATION: synthetic extension primer for paralogous
      sequence mismatches (PSM) on paralogous loci on chromosomes
      21 and 6

<400> SEQUENCE: 46
tgggcgcggg agcggacttc gctgg                                       25

<210> SEQ ID NO 47
<211> LENGTH: 25
<212> TYPE: DNA
<213> ORGANISM: Artificial Sequence
<220> FEATURE:
<223> OTHER INFORMATION: synthetic digital PCR analysis co-amplification
      forward primer for 87-bp amplicon for zinc finger
      protein sequences on chromosome X (ZFX) and Y
      (ZFY)

<400> SEQUENCE: 47
caagtgctgg actcagatgt aactg                                       25

<210> SEQ ID NO 48
<211> LENGTH: 28
<212> TYPE: DNA
<213> ORGANISM: Artificial Sequence
<220> FEATURE:
<223> OTHER INFORMATION: synthetic digital PCR analysis co-amplification
      reverse primer for 87-bp amplicon for zinc finger
      protein sequences on chromosome X (ZFX) and Y
      (ZFY)

<400> SEQUENCE: 48
tgaagtaatg tcagaagcta aaacatca                                    28

<210> SEQ ID NO 49
<211> LENGTH: 16
<212> TYPE: DNA
<213> ORGANISM: Artificial Sequence
<220> FEATURE:
<223> OTHER INFORMATION: synthetic chromosome-specific TaqMan probe
      designed to target chromosome X paralog
<220> FEATURE:
<221> NAME/KEY: modified_base
<222> LOCATION: (1)...(1)
<223> OTHER INFORMATION: t modified by fluorescent reporter VIC
<220> FEATURE:
<221> NAME/KEY: modified_base
<222> LOCATION: (16)...(16)
<223> OTHER INFORMATION: a modified by minor groove binding
      non-fluorescent quencher (MGBNFQ)

<400> SEQUENCE: 49
tctttagcac attgca                                                 16

-continued

<210> SEQ ID NO 50
<211> LENGTH: 17
<212> TYPE: DNA
<213> ORGANISM: Artificial Sequence
<220> FEATURE:
<223> OTHER INFORMATION: synthetic chromosome-specific TaqMan probe
      designed to target chromosome Y paralog
<220> FEATURE:
<221> NAME/KEY: modified_base
<222> LOCATION: (1)...(1)
<223> OTHER INFORMATION: t modified by 6-carboxyfluorescein (FAM)
<220> FEATURE:
<221> NAME/KEY: modified_base
<222> LOCATION: (17)...(17)
<223> OTHER INFORMATION: c modified by minor groove binding
      non-fluorescent quencher (MGBNFQ)

<400> SEQUENCE: 50
tctttaccac actgcac                                                  17

<210> SEQ ID NO 51
<211> LENGTH: 19
<212> TYPE: DNA
<213> ORGANISM: Artificial Sequence
<220> FEATURE:
<223> OTHER INFORMATION: synthetic digital PCR co-amplification forward
      primer for 87-bp amplicon of beta-globin
      (hemoglobin beta (HBB)) HbE mutation forward
      primer

<400> SEQUENCE: 51
gggcaaggtg aacgtggat                                                19

<210> SEQ ID NO 52
<211> LENGTH: 29
<212> TYPE: DNA
<213> ORGANISM: Artificial Sequence
<220> FEATURE:
<223> OTHER INFORMATION: synthetic digital PCR co-amplification forward
      primer for 87-bp amplicon of beta-globin
      (hemoglobin beta (HBB)) HbE mutation reverse
      primer

<400> SEQUENCE: 52
ctattggtct ccttaaacct gtcttgtaa                                     29

<210> SEQ ID NO 53
<211> LENGTH: 14
<212> TYPE: DNA
<213> ORGANISM: Artificial Sequence
<220> FEATURE:
<223> OTHER INFORMATION: synthetic allele-G-specific TaqMan probe
      targeting beta-globin (hemoglobin beta (HBB)) HbE mutation
      normal allele
<220> FEATURE:
<221> NAME/KEY: modified_base
<222> LOCATION: (1)...(1)
<223> OTHER INFORMATION: t modified by fluorescent reporter VIC
<220> FEATURE:
<221> NAME/KEY: modified_base
<222> LOCATION: (14)...(14)
<223> OTHER INFORMATION: c modified by minor groove binding
      non-fluorescent quencher (MGBNFQ)

<400> SEQUENCE: 53
ttggtggtga ggcc                                                     14

<210> SEQ ID NO 54
<211> LENGTH: 14

```
<212> TYPE: DNA
<213> ORGANISM: Artificial Sequence
<220> FEATURE:
<223> OTHER INFORMATION: synthetic allele-A-specific TaqMan probe
      targeting beta-globin (hemoglobin beta (HBB)) HbE mutation
      mutant allele
<220> FEATURE:
<221> NAME/KEY: modified_base
<222> LOCATION: (1)...(1)
<223> OTHER INFORMATION: t modified by 6-carboxyfluorescein (FAM)
<220> FEATURE:
<221> NAME/KEY: modified_base
<222> LOCATION: (14)...(14)
<223> OTHER INFORMATION: c modified by minor groove binding
      non-fluorescent quencher (MGBNFQ)

<400> SEQUENCE: 54
ttggtggtaa ggcc                                                      14

<210> SEQ ID NO 55
<211> LENGTH: 20
<212> TYPE: DNA
<213> ORGANISM: Artificial Sequence
<220> FEATURE:
<223> OTHER INFORMATION: synthetic digital PCR co-amplification forward
      primer for 87-bp and 83-bp amplicon of CD41/42
      deletion mutation normal and mutant allele

<400> SEQUENCE: 55
ttttcccacc cttaggctgc                                                20

<210> SEQ ID NO 56
<211> LENGTH: 23
<212> TYPE: DNA
<213> ORGANISM: Artificial Sequence
<220> FEATURE:
<223> OTHER INFORMATION: synthetic digital PCR co-amplification reverse
      primer for 87-bp and 83-bp amplicon of CD41/42
      deletion mutation normal and mutant allele

<400> SEQUENCE: 56
acagcatcag gagtggacag atc                                            23

<210> SEQ ID NO 57
<211> LENGTH: 19
<212> TYPE: DNA
<213> ORGANISM: Artificial Sequence
<220> FEATURE:
<223> OTHER INFORMATION: synthetic allele-specific TaqMan probe
      targeting CD41/42 deletion mutation normal allele (without
      deletion)
<220> FEATURE:
<221> NAME/KEY: modified_base
<222> LOCATION: (1)...(1)
<223> OTHER INFORMATION: c modified by fluorescent reporter VIC
<220> FEATURE:
<221> NAME/KEY: modified_base
<222> LOCATION: (19)...(19)
<223> OTHER INFORMATION: t modified by minor groove binding
      non-fluorescent quencher (MGBNFQ)

<400> SEQUENCE: 57
cagaggttct ttgagtcct                                                 19

<210> SEQ ID NO 58
<211> LENGTH: 15
<212> TYPE: DNA
<213> ORGANISM: Artificial Sequence
<220> FEATURE:
<223> OTHER INFORMATION: synthetic allele-specific TaqMan probe
      targeting CD41/42 deletion mutation mutant allele (with
```

```
          deletion)
<220> FEATURE:
<221> NAME/KEY: modified_base
<222> LOCATION: (1)...(1)
<223> OTHER INFORMATION: a modified by 6-carboxyfluorescein (FAM)
<220> FEATURE:
<221> NAME/KEY: modified_base
<222> LOCATION: (15)...(15)
<223> OTHER INFORMATION: t modified by minor groove binding
      non-fluorescent quencher (MGBNFQ)

<400> SEQUENCE: 58
agaggttgag tcctt                                                    15
```

DETERMINING PERCENTAGE OF FETAL DNA IN MATERNAL SAMPLE

CLAIM OF PRIORITY

The present application is a divisional of U.S. application Ser. No. 12/178,116 entitled "Determining A Nucleic Acid Sequence Imbalance" filed Jul. 23, 2008, which claims priority from and is a non-provisional application of U.S. Provisional Application No. 60/951,438, entitled "Determining A Nucleic Acid Sequence Imbalance" filed Jul. 23, 2007, the entire contents of which are herein incorporated by reference for all purposes.

CROSS-REFERENCES TO RELATED APPLICATIONS

The present application is also related to U.S. application Ser. No. 12/178,181 entitled "Diagnosing Fetal Chromosomal Aneuploidy Using Genomic Sequencing," filed Jul. 23, 2008, the entire contents of which are herein incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -52-1-2.TXT, created on Oct. 24, 2013, 24,576 bytes, machine format IBM-PC, MS-Windows operating system, is hereby incorporated by reference in its entirety for all purposes.

FIELD OF THE INVENTION

This invention generally relates to the diagnostic testing of genotypes and diseases by determining an imbalance between two different nucleic acid sequences, and more particularly to the identification of Down syndrome, other chromosomal aneuploidies, mutations and genotypes in a fetus via testing a sample of maternal blood. The invention also relates to the detection of cancer, the monitoring of transplantation, and the monitoring of infectious diseases.

BACKGROUND

Genetic diseases, cancers, and other conditions often result from or produce an imbalance in two corresponding chromosomes or alleles or other nucleic acid sequences. That is an amount of one sequence relative to another sequence is larger or smaller than normal. Usually, the normal ratio is an even 50/50 ratio. Down Syndrome (trisomy 21) is such a disease having an imbalance of an extra chromosome 21.

Conventional prenatal diagnostic methods of trisomy 21 involve the sampling of fetal materials by invasive procedures such as amniocentesis or chorionic villus sampling, which pose a finite risk of fetal loss. Non-invasive procedures, such as screening by ultrasonography and biochemical markers, have been used to risk-stratify pregnant women prior to definitive invasive diagnostic procedures. However, these screening methods typically measure epiphenomena that are associated with trisomy 21 instead of the core chromosomal abnormality, and thus have suboptimal diagnostic accuracy and other disadvantages, such as being highly influenced by gestational age.

The discovery of circulating cell-free fetal DNA in maternal plasma in 1997 offered new possibilities for noninvasive prenatal diagnosis (Lo, Y M D and Chiu, R W K 2007 *Nat Rev Genet* 8, 71-77). While this method has been readily applied to the prenatal diagnosis of sex-linked (Costa, J M et al. 2002 *N Engl J Med* 346, 1502) and certain single gene disorders (Lo, Y M D et al. 1998 *N Engl J Med* 339, 1734-1738), its application to the prenatal detection of fetal chromosomal aneuploidies has represented a considerable challenge (Lo, Y M D and Chiu, R W K 2007, supra). First, fetal nucleic acids co-exist in maternal plasma with a high background of nucleic acids of maternal origin that can often interfere with the analysis (Lo, Y M D et al. 1998 *Am J Hum Genet* 62, 768-775). Second, fetal nucleic acids circulate in maternal plasma predominantly in a cell-free form, making it difficult to derive dosage information of genes or chromosomes within the fetal genome.

Significant developments overcoming these challenges have recently been made (Benachi, A & Costa, J M 2007 *Lancet* 369, 440-442). One approach detects fetal-specific nucleic acids in the maternal plasma, thus overcoming the problem of maternal background interference (Lo, Y M D and Chiu, R W K 2007, supra). Dosage of chromosome 21 was inferred from the ratios of polymorphic alleles in the placenta-derived DNA/RNA molecules. However, this method is less accurate when samples contain lower amount of the targeted gene and can only be applied to fetuses who are heterozygous for the targeted polymorphisms, which is only a subset of the population if one polymorphism is used.

Dhallan et al (Dhallan, R, et al. 2007, supra Dhallan, R, et al. 2007 *Lancet* 369, 474-481) described an alternative strategy of enriching the proportion of circulating fetal DNA by adding formaldehyde to maternal plasma. The proportion of chromosome 21 sequences contributed by the fetus in maternal plasma was determined by assessing the ratio of paternally-inherited fetal-specific alleles to non-fetal-specific alleles for single nucleotide polymorphisms (SNPs) on chromosome 21. SNP ratios were similarly computed for a reference chromosome. An imbalance of fetal chromosome 21 was then inferred by detecting a statistically significant difference between the SNP ratios for chromosome 21 and those of the reference chromosome, where significant is defined using a fixed p-value of $\leq 0.05$. To ensure high population coverage, more than 500 SNPs were targeted per chromosome. However, there have been controversies regarding the effectiveness of formaldehyde to enrich to a high proportion (Chung, G T Y, et al. 2005 *Clin Chem* 51, 655-658), and thus the reproducibility of the method needs to be further evaluated. Also, as each fetus and mother would be informative for a different number of SNPs for each chromosome, the power of the statistical test for SNP ratio comparison would be variable from case to case (Lo, Y M D & Chiu, R W K. 2007 *Lancet* 369, 1997). Furthermore, since these approaches depend on the detection of genetic polymorphisms, they are limited to fetuses heterozygous for these polymorphisms.

Using polymerase chain reaction (PCR) and DNA quantification of a chromosome 21 locus and a reference locus in amniocyte cultures obtained from trisomy 21 and euploid fetuses, Zimmermann et al (2002 *Clin Chem* 48, 362-363) were able to distinguish the two groups of fetuses based on the 1.5-fold increase in chromosome 21 DNA sequences in the former. Since a 2-fold difference in DNA template concentration constitutes a difference of only one threshold cycle (Ct), the discrimination of a 1.5-fold difference has been the limit of conventional real-time PCR. To achieve finer degrees of quantitative discrimination, alternative strategies are needed. Accordingly, some embodiments of the present invention use digital PCR (Vogelstein, B et al. 1999 *Proc Natl Acad Sci U S A* 96, 9236-9241) for this purpose.

Digital PCR has been developed for the detection of allelic ratio skewing in nucleic acid samples (Chang, H W et al. 2002 *J Natl Cancer Inst* 94, 1697-1703). Clinically, it has been shown to be useful for the detection of loss of heterozygosity (LOH) in tumor DNA samples (Zhou, W. et al. 2002 *Lancet* 359, 219-225). For the analysis of digital PCR results, sequential probability ratio testing (SPRT) has been adopted by previous studies to classify the experimental results as being suggestive of the presence of LOH in a sample or not (El Karoui at al. 2006 *Stat Med* 25, 3124-3133). In methods used in the previous studies, the cutoff value to determine LOH used a fixed reference ratio of the two alleles in the DNA of 2/3. As the amount, proportion, and concentration of fetal nucleic acids in maternal plasma are variable, these methods are not suitable for detecting trisomy 21 using fetal nucleic acids in a background of maternal nucleic acids in maternal plasma.

It is desirable to have a noninvasive test for fetal trisomy 21 (and other imbalances) detection based on circulating fetal nucleic acid analysis, especially one that is independent of the use of genetic polymorphisms and/or of fetal-specific markers. It is also desirable to have accurate determination of cutoff values and counting of sequences, which can reduce the number of wells of data and/or the amount of maternal plasma nucleic acid molecules necessary for accuracy, thus providing increased efficiency and cost-effectiveness. It is also desirable that noninvasive tests have high sensitivity and specificity to minimize false diagnoses.

Another application for fetal DNA detection in maternal plasma is for the prenatal diagnosis of single gene disorders such as beta-thalassemia. However, as fetal DNA only constitutes a minor fraction of DNA in maternal plasma, it is thought that this approach can only detect a mutation that a fetus has inherited from its father, but which is absent from the mother. Examples of this include the 4 bp deletion in codon 41/42 of the beta-globin gene causing beta-thalassemia (Chiu R W K et al. 2002 *Lancet*, 360, 998-1000) and the Q890X mutation of the cystic fibrosis transmembrane conductance regulator gene causing cystic fibrosis (Gonzalez-Gonzalez et al 2002 *Prenat Diagn*, 22, 946-8). However, as both beta-thalassemia and cystic fibrosis are autosomal recessive conditions, in which the fetus would need to inherit a mutation from each parent before the disease would manifest itself, the detection of merely the paternally-inherited mutation would only increase the risk of having the fetus having the disease from 25% to 50%. Diagnostically this is not ideal. Thus, the main diagnostic application of the existing approach would be for the scenario when no paternally-inherited fetal mutation can be detected in maternal plasma, when the fetus can then be excluded from having the homozygous disease state. However, diagnostically, this approach has the disadvantage that the conclusion is made based on the negative detection of the paternal mutation. Thus, an approach which would allow the complete fetal genotype (be it homozygous normal, homozygous mutant, or heterozygous) to be determined from maternal plasma, without the above limitation, would be very desirable.

BRIEF SUMMARY

Embodiments of this invention provides methods, systems, and apparatus for determining whether a nucleic acid sequence imbalance (e.g., allelic imbalance, mutational imbalance, or chromosome imbalance) exists within a biological sample. One or more cutoff values for determining an imbalance of, for example, a ratio of amounts of the two sequences (or sets of sequences) are chosen.

In one embodiment, the cutoff value is determined based at least in part on the percentage of fetal (clinically relevant nucleic acid) sequences in a biological sample, such as maternal plasma or serum or urine, which contains a background of maternal nucleic acid sequences. In another embodiment, the cutoff value is determined based on an average concentration of a sequence in a plurality of reactions. In one aspect, the cutoff value is determined from a proportion of informative wells that are estimated to contain a particular nucleic acid sequence, where the proportion is determined based on the above-mentioned percentage and/or average concentration.

The cutoff value may be determined using many different types of methods, such as SPRT, false discovery, confidence interval, receiver operating characteristic (ROC). This strategy further minimized the amount of testing required before confident classification could be made. This is of particular relevance to plasma nucleic acid analysis where the template amount is often limiting.

According to one exemplary embodiment, a method is provided for determining whether a nucleic acid sequence imbalance exists within a biological sample, the method comprising: receiving data from a plurality of reactions, wherein the data includes: (1) a first set of quantitative data indicating a first amount of a clinically relevant nucleic acid sequence; and (2) a second set of quantitative data indicating a second amount of a background nucleic acid sequence different from the clinically relevant nucleic acid sequence; determining a parameter from the two data sets; deriving a first cutoff value from an average concentration of a reference nucleic acid sequence in each of the plurality of reactions, wherein the reference nucleic acid sequence is either the clinically relevant nucleic acid sequence or the background nucleic acid sequence; comparing the parameter to the first cutoff value; and based on the comparison, determining a classification of whether a nucleic acid sequence imbalance exists.

According to another exemplary embodiment, a method is provided for determining whether a nucleic acid sequence imbalance exists within a biological sample, the method comprising: receiving data from a plurality of reactions, wherein the data includes: (1) a first set of quantitative data indicating a first amount of a clinically relevant nucleic acid sequence; and (2) a second set of quantitative data indicating a second amount of a background nucleic acid sequence different from the clinically relevant nucleic acid sequence, wherein the clinically relevant nucleic acid sequence and the background nucleic acid sequence come from a first type of cells and from one or more second types of cells; determining a parameter from the two data sets; deriving a first cutoff value from a first percentage resulting from a measurement of an amount of a nucleic acid sequence from the first type of cells in the biological sample; comparing the parameter to the cutoff value; and based on the comparison, determining a classification of whether a nucleic acid sequence imbalance exists.

Other embodiments of the invention are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 2B shows a table of examples of frequently detectable chromosomal aberrations in cancers.

FIG. 6 shows a table that tabulates the expected digital RNA-SNP allelic ratio and $P_r$ of trisomy 21 samples for a range of template concentrations expressed as the average reference template concentration per well ($m_r$) according to an embodiment of the present invention.

FIG. 9A shows a table of a comparison of the effectiveness of the new and old SPRT algorithms for classifying euploid and trisomy 21 cases in 96-well digital RNA-SNP analyses according to an embodiment of the present invention.

FIG. 9B shows a table of a comparison of the effectiveness of the new and old SPRT algorithms for classifying euploid and trisomy 21 cases in 384-well digital RNA-SNP analyses according to an embodiment of the present invention.

FIG. 10 is a table showing the percentages of fetuses correctly and incorrectly classified as euploid or aneuploid and those not classifiable for the given informative counts according to an embodiment of the present invention.

FIG. 11 is a table 1100 showing computer simulations for digital RCD analysis for a pure (100%) fetal DNA sample according to an embodiment of the present invention.

FIG. 12 is a table 1200 showing results of computer simulation of accuracies of digital RCD analysis at $m_r$=0.5 for the classification of samples from euploid or trisomy 21 fetuses with different fractional concentrations of fetal DNA according to an embodiment of the present invention.

FIG. 13A shows a table 1300 of digital RNA-SNP analysis in placental tissues of euploid and trisomy 21 pregnancies according to an embodiment of the present invention.

FIG. 13B shows a table 1350 of digital RNA-SNP analysis of maternal plasma from euploid and trisomy 21 pregnancies according to an embodiment of the present invention.

FIG. 15A shows a table of digital RNA-SNP analysis in placental tissues of euploid and trisomy 21 pregnancies according to an embodiment of the present invention.

FIG. 15B shows a table of digital RNA-SNP data of the 12 reaction panels from one maternal plasma sample according to an embodiment of the present invention.

FIG. 15C shows a table of digital RNA-SNP analysis of maternal plasma from euploid and trisomy 21 pregnancies according to an embodiment of the present invention.

FIG. 16A shows a table for a digital RNA-SNP analysis of euploid and trisomy 18 placentas according to an embodiment of the present invention.

FIG. 16B shows an SPRT interpretation of digital RNA-SNP data for euploid and trisomy 18 placentas according to an embodiment of the present invention.

FIG. 17 shows a table of a digital RCD analysis of 50% placental/maternal blood cell DNA mixtures of euploid and trisomy 21 pregnancies according to an embodiment of the present invention.

FIG. 19 shows a table of digital RCD analysis of amniotic fluid samples from euploid and trisomy 21 pregnancies according to an embodiment of the present invention.

FIG. 20 shows a table of digital RCD analysis of placental DNA samples from euploid and trisomy 18 pregnancies (E=euploid; T18=trisomy 18) according to an embodiment of the present invention.

FIG. 21 shows a table of a multiplex digital RCD analysis of 50% placental/maternal blood cell DNA mixtures of euploid and trisomy 21 pregnancies (E=euploid; T21=trisomy 21; U=unclassified) according to an embodiment of the present invention.

FIGS. 22A and 22B show a table of a multiplex digital RCD analysis of 50% euploid or trisomy 21 placental genomic DNA/50% maternal buffy coat DNA mix according to an embodiment of the present invention. Unclass denotes unclassifiable and T21 denotes trisomy 21.

FIG. 24A shows a table of a digital RMD analysis of female/male and male/male DNA mixtures according to an embodiment of the present invention.

FIG. 24B shows a table of a digital RMD analysis of mixtures with 25% female and 75% male DNA according to an embodiment of the present invention.

FIG. 25 shows a table of a digital RMD analysis of 15%-50% DNA mixtures mimicking maternal plasma samples for HbE mutation according to an embodiment of the present invention.

FIG. 26A shows a table of a digital RMD analysis of 5%-50% DNA mixtures mimicking maternal plasma samples for CD41/42 mutation according to an embodiment of the present invention.

FIG. 26B shows a table of a digital RMD analysis of 20% DNA mixtures mimicking maternal plasma samples for CD41/42 mutation according to an embodiment of the present invention.

DEFINITIONS

Figure 1:
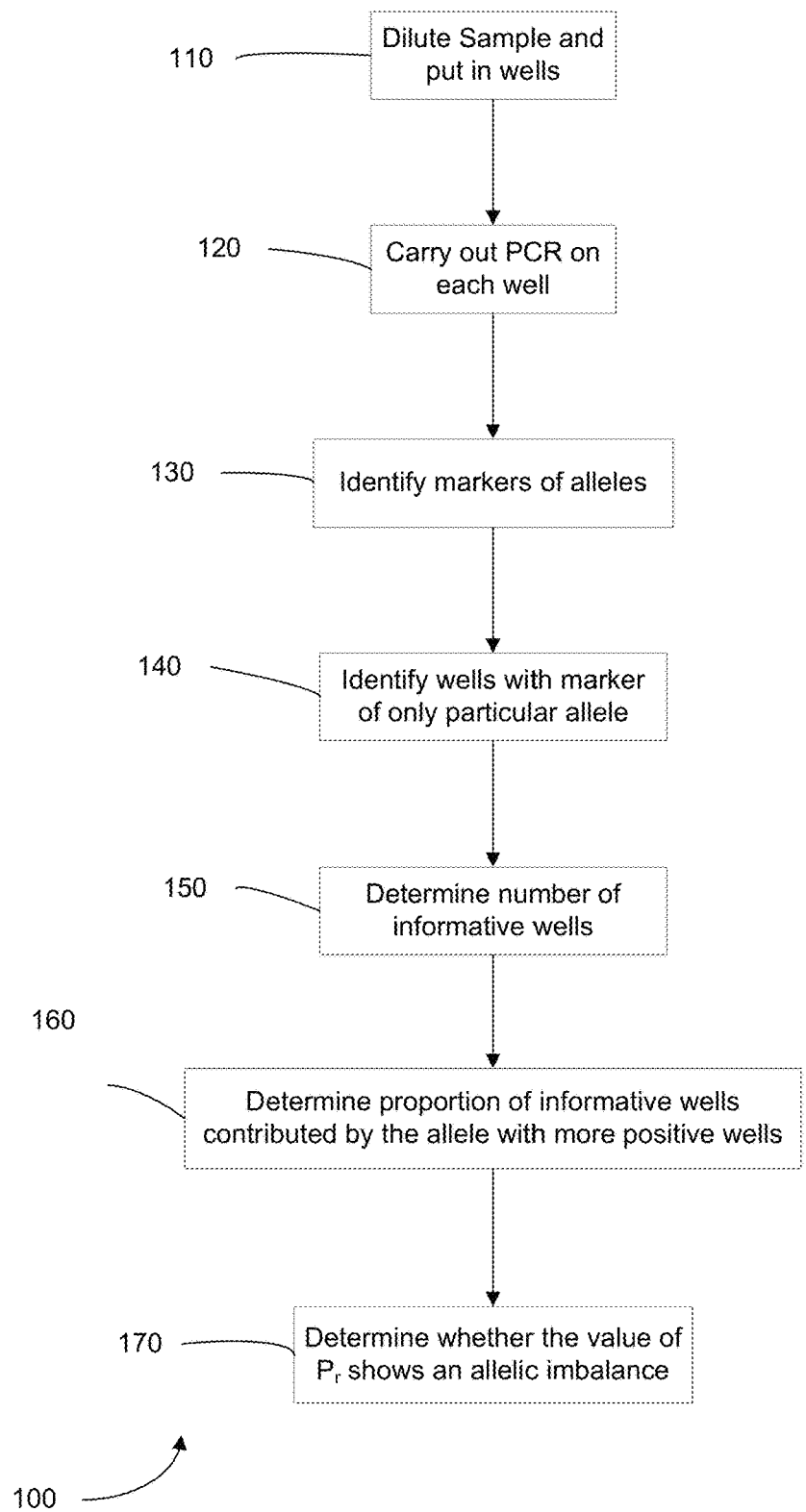
FIG. 1 is a flowchart illustrating a digital PCR experiment.

The term "biological sample" as used herein refers to any sample that is taken from a subject (e.g., a human, such as a pregnant woman) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons).

The term "reaction" as used herein refers to any process involving a chemical, enzymatic, or physical action that is indicative of the presence or absence of a particular polynucleotide sequence of interest. An example of a "reaction" is an amplification reaction such as a polymerase chain reaction (PCR). Another example of a "reaction" is a sequencing reaction, either by synthesis or by ligation. An "informative reaction" is one that indicates the presence of one or more particular polynucleotide sequence of interest, and in one case where only one sequence of interest is present. The term "well" as used herein refers to a reaction at a predetermined location within a confined structure, e.g., a well-shaped vial, cell, or chamber in a PCR array.

The term "clinically relevant nucleic acid sequence" as used herein can refer to a polynucleotide sequence corresponding to a segment of a larger genomic sequence whose potential imbalance is being tested or to the larger genomic sequence itself. One example is the sequence of chromosome 21. Other examples include chromosome 18, 13, X and Y. Yet other examples include mutated genetic sequences or genetic polymorphisms or copy number variations that a fetus may inherit from one or both of its parents. Yet other examples include sequences which are mutated, deleted, or amplified in a malignant tumor, e.g. sequences in which loss of heterozygosity or gene duplication occur. In some embodiments, multiple clinically relevant nucleic acid sequences, or equivalently multiple makers of the clinically relevant nucleic acid sequence, can be used to provide data for detecting the imbalance. For instance, data from five non-consecutive sequences on chromosome 21 can be used in an additive fashion for the determination of a possible chromosomal 21 imbalance, effectively reducing the need of sample volume to 1/5.

The term "background nucleic acid sequence" as used herein refers to a nucleic acid sequence whose normal ratio to the clinically relevant nucleic acid sequence is known, for instance a 1-to-1 ratio. As one example, the background nucleic acid sequence and the clinically relevant nucleic acid sequence are two alleles from the same chromosome that are distinct due to heterozygosity. In another example, the background nucleic acid sequence is one allele that is heterozygous to another allele that is the clinically relevant nucleic acid sequence. Moreover, some of each of the background nucleic acid sequence and the clinically relevant nucleic acid sequence may come from different individuals.

The term "reference nucleic acid sequence" as used herein refers to a nucleic acid sequence whose average concentration per reaction is known or equivalently has been measured.

The term "overrepresented nucleic acid sequence" as used herein refers to the nucleic acid sequence among two sequences of interest (e.g., a clinically relevant sequence and a background sequence) that is in more abundance than the other sequence in a biological sample.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "quantitative data" as used herein means data that are obtained from one or more reactions and that provide one or more numerical values. For example, the number of wells that show a fluorescent marker for a particular sequence would be quantitative data.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "imbalance" as used herein means any significant deviation as defined by at least one cutoff value in a quantity of the clinically relevant nucleic acid sequence from a reference quantity. For example, the reference quantity could be a ratio of 3/5, and thus an imbalance would occur if the measured ratio is 1:1.

DETAILED DESCRIPTION OF THE INVENTION

This invention provides methods, systems, and apparatus for determining whether an increase or decrease compared to a reference (e.g. non-diseased) quantity of a clinically-relevant nucleic acid sequence in relation to other non-clinically-relevant sequences (e.g., a chromosomal or allelic imbalance) exists within a biological sample. One or more cutoff values are chosen for determining whether a change compared to the reference quantity exists (i.e. an imbalance), for example, with regards to the ratio of amounts of two sequences (or sets of sequences). The change detected in the reference quantity may be any deviation (upwards or downwards) in the relation of the clinically-relevant nucleic acid sequence to the other non-clinically-relevant sequences. Thus, the reference state may be any ratio or other quantity (e.g. other than a 1-1 correspondence), and a measured state signifying a change may be any ratio or other quantity that differs from the reference quantity as determined by the one or more cutoff values.

The clinically relevant nucleic acid sequence and the background nucleic acid sequence may come from a first type of cells and from one or more second types of cells. For example, fetal nucleic acid sequences originating from fetal/placental cells are present in a biological sample, such as maternal plasma, which contains a background of maternal nucleic acid sequences originating from maternal cells. Thus, in one embodiment, the cutoff value is determined based at least in part on a percentage of the first type of cells in a biological sample. Note the percentage of fetal sequences in a sample may be determined by any fetal-derived loci and not limited to measuring the clinically-relevant nucleic acid sequences. In another embodiment, the cutoff value is determined at least in part on the percentage of tumor sequences in a biological sample, such as plasma, serum, saliva or urine, which contains a background of nucleic acid sequences derived from the non-malignant cells within the body.

In yet another embodiment, the cutoff value is determined based on an average concentration of a sequence in a plurality of reactions. In one aspect, the cutoff value is determined from a proportion of informative wells that are estimated to contain a particular nucleic acid sequence, where the proportion is determined based on the above-mentioned percentage and/or average concentration. The cutoff value may be determined using many different types of methods, such as SPRT, false discovery, confidence interval, receiver operating characteristic (ROC). This strategy further minimizes the amount of testing required before confident classification can be made. This is of particular relevance to plasma nucleic acid analysis where the template amount is often limiting. Although presented with respect to digital PCR, other methods may be used.

Digital PCR involves multiple PCR analyses on extremely dilute nucleic acids such that most positive amplifications reflect the signal from a single template molecule. Digital PCR thereby permits the counting of individual template molecules. The proportion of positive amplifications among the total number of PCRs analyzed allows an estimation of the template concentration in the original or non-diluted sample. This technique has been proposed to allow the detection of a variety of genetic phenomena (Vogelstein, B et al. 1999, supra) and has previously been used for the detection of loss of heterozygosity in tumor samples (Zhou, W. et al. 2002, supra) and in the plasma of cancer patients (Chang, HW et al. 2002, supra). Since template molecule quantification by digital PCR does not rely on dose-response relationships between reporter dyes and nucleic acid concentrations, its analytical precision should theoretically be superior to that of real-time PCR. Hence, digital PCR could potentially allow the discrimination of finer degrees of quantitative differences between target and reference loci.

To test this, we first assessed if digital PCR could determine the allelic ratio of PLAC4 mRNA (Lo, Y M D, et al. 2007 *Nat Med* 13, 218-223), a placental transcript from chromosome 21, in maternal plasma and thereby distinguish trisomy 21 and euploid fetuses. This approach is referred as the digital RNA-SNP method. We then evaluated whether the increased precision of digital PCR would allow the detection of fetal chromosomal aneuploidies without depending on genetic polymorphisms. We call this digital relative chromosome dosage (RCD) analysis. The former approach is polymorphism-dependent but requires less precision in quantitative discrimination while the latter approach is polymorphism-independent but requires a higher precision for quantitative discrimination.

I. Digital RNA-SNP

A. Overview

Digital PCR is capable of detecting the presence of allelic ratio skewing of two alleles in a DNA sample. For example, it has been used to detect loss of heterozygosity (LOH) in a tumor DNA sample. Assuming that there are two alleles in the DNA sample, namely A and G, and the A allele would be lost in the cells with LOH. When LOH is present in 50% of cells in the tumor sample, the allelic ratio of G:A in the DNA sample would be 2:1. However, if LOH is not present in the tumor sample, the allelic ratio of G:A would be 1:1.

FIG. 1 is a flowchart 100 illustrating a digital PCR experiment. In step 110, the DNA sample is diluted and then distributed to separate wells. Note that the inventors have determined that some plasma nucleic acid species are already quite diluted in the original sample. Accordingly, there is no need for dilution for some templates, if they are already present at the necessary concentrations. In the previous studies (e.g. Zhou et al 2002, supra), a DNA sample is diluted to an extent such that the average concentration of a specific "template DNA" is approximately 0.5 molecule of one of the two templates per well. Note that the term "template DNA" appears to refer to either the A or the G alleles, and that there is no rationale provided for this specific concentration.

In step 120, in each well, a PCR process is carried out to detect the A and/or the G allele simultaneously. In step 130, the markers in each well are identified (e.g. via fluorescence), e.g. A, G, A and G, or neither. In the absence of LOH the abundance of the A and the G alleles in the DNA sample would be the same (one copy each per cell). Therefore, the probabilities of a well being positive for the A allele and for the G allele would be the same. This would be reflected by the similar numbers of wells being positive for the A or the G alleles. However, when LOH is present in 50% or greater of cells in a tumor sample, the allelic ratio of the G and the A alleles would be at least 2:1. Previous methods simply assumed that the sample was at least 50% cancerous. Thus, the probability of a well being positive for the G allele would be higher than that for the A allele. As a result, the number of wells being positive for the G allele would be higher than that for the A allele.

In step 140, to classify the digital PCR results, the number of wells being positive for each allele but not the other would be counted. In the above example, the number of wells being positive for the A allele but negative for the G allele, and the number of wells positive for the G allele but negative for the A allele are counted. In one embodiment, the allele showing less positive wells is regarded as the reference allele.

In step 150, the total number of informative wells is determined as the sum of the numbers of positive wells for either of the two alleles. In step 160, the proportion ($P_r$) of informative wells (an example of a parameter) contributed by the allele with more positive wells is calculated.

$P_r$=No. of wells only positive for the allele with more positive wells/Total no. of wells positive for only one allele (*A* or *G*).

Other embodiments could use all wells with one of the alleles divided by all wells with at least one allele.

In step 170, it is determined whether the value of $P_r$ shows an allelic imbalance. As accuracy and efficiency are desired, this task is not straightforward. One method for determining an imbalance uses a Bayesian-type likelihood method, sequential probability ratio testing (SPRT). SPRT is a method which allows two probabilistic hypotheses to be compared as data accumulate. In other words, it is a statistical method to classify the results of digital PCR as being suggestive of the presence or absence of allelic skewing. It has the advantage of minimizing the number of wells to be analyzed to achieve a given statistical power and accuracy.

In an exemplary SPRT analysis, the experimental results would be tested against the null and alternative hypotheses. The alternative hypothesis is accepted when there is allelic ratio skewing in the sample. The null hypothesis is accepted when there is no allelic ratio skewing in the sample. The value $P_r$ would be compared with two cutoff values to accept the null or alternative hypotheses. If neither hypothesis is accepted, the sample would be marked as unclassified which means that the observed digital PCR result is not sufficient to classify the sample with the desired statistical confidence.

The cutoff values for accepting the null or alternative hypotheses have typically been calculated based on a fixed value of $P_r$ under the assumptions stated in the hypotheses. In the null hypothesis, the sample is assumed to exhibit no allelic ratio skewing. Therefore, the probabilities of each well being positive for the A and the G alleles would be the same and, hence, the expected value of $P_r$ would be 1/2. In the alternative hypothesis, the expected value of $P_r$ has been taken to be 2/3 or about halfway between 0.5 and 2/3, e.g. 0.585. Also, due to a limited number of experiments, one can choose an upper bound (0.585+3/N) and a lower bound taken as (0.585-3/N).

B. Detection of Down Syndrome

In one embodiment of the present invention, digital SNP is used to detect fetal Down syndrome from a pregnant woman's plasma. Using markers specific to fetal/placental cells, the ratio of alleles in chromosome 21 may be measured. For example, to determine if an observed degree of overrepresentation of a PLAC4 allele is statistically significant, SPRT is used.

According to one exemplary embodiment, digital RNA-SNP determines an imbalance in the ratio of polymorphic alleles of an A/G SNP, rs8130833, located on PLAC4 mRNA which is transcribed from chromosome 21 and expressed by the placenta. For a heterozygous euploid fetus, the A and G alleles should be equally represented in the fetal genome (1:1 genomic ratio); while in trisomy 21, the trisomic chromosome 21 would be associated with an additional copy of one of the SNP alleles in the fetal genome giving a 2:1 ratio. The aim of the digital PCR analysis is to determine whether the amounts of the two PLAC4 alleles in the analyzed sample are equal or otherwise. Thus, both the A and G PLAC4 alleles are the target templates. A real-time PCR assay was designed to amplify PLAC4 mRNA and the two SNP alleles were discriminated by TaqMan fluorescent probes. A schematic illustration of the analytical steps is shown in FIG. 2A.

Figure 2A:
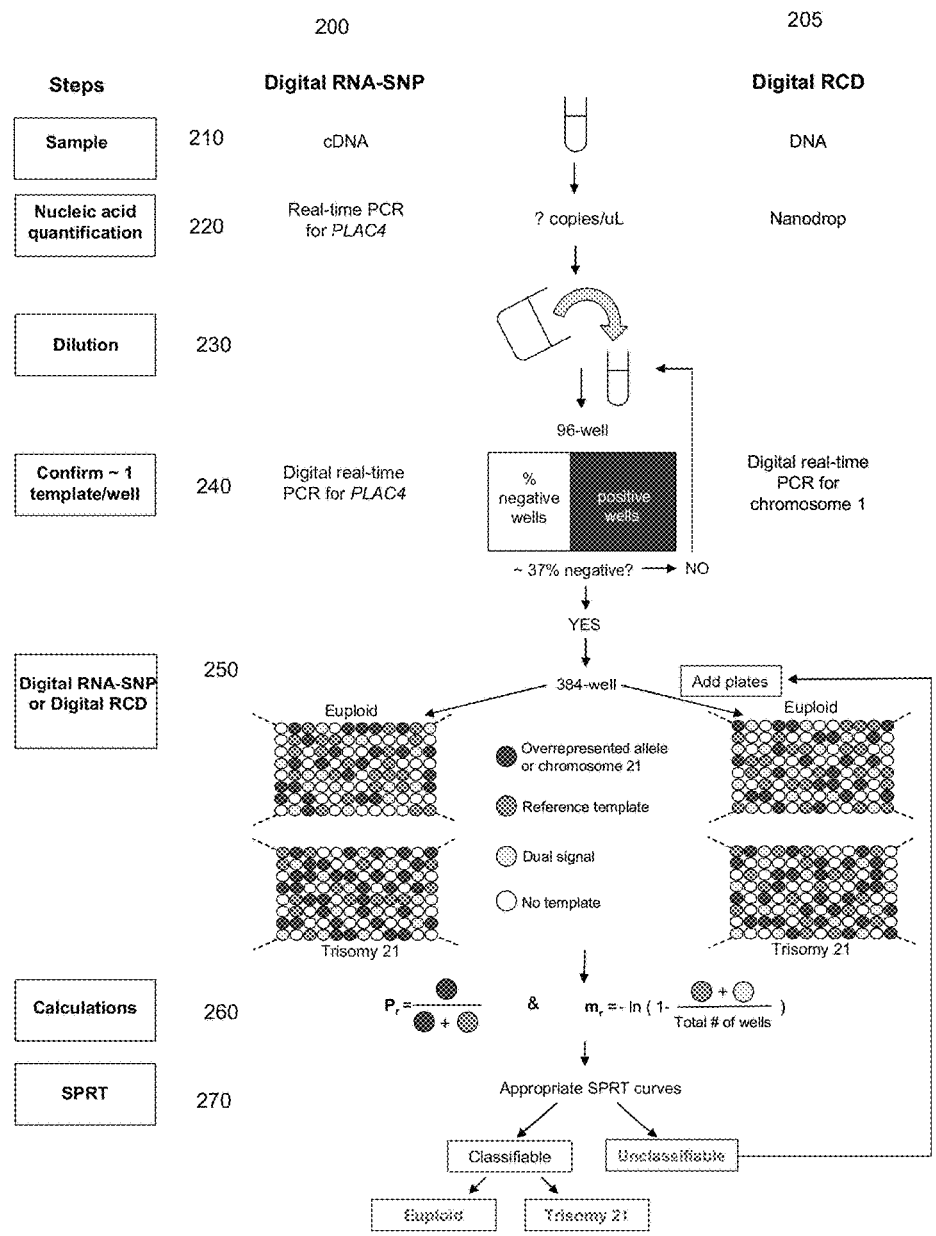
FIG. 2A illustrates a digital RNA-SNP and RCD method according to an embodiment of the present invention.

FIG. 2A illustrates a digital RNA-SNP method 200 according to an embodiment of the present invention. In step 210, the sample is received. In step 220, the nucleic acid sequence, e.g. PLAC4 mRNA, is quantified in extracted RNA samples. In one embodiment, this is done by real-time PCR for PLAC4 mRNA. In one aspect, this step provides the operator with an idea about how much dilution is required before the target reaches the 'realm' of digital PCR analysis.

In step 230, the sample is diluted. In step 240, a concentration of the diluted sample is measured. The diluted sample concentration may be confirmed to be ~1 template/well (i.e. reference or non-reference sequence or either allele). Some embodiments use techniques described in section IV for this measurement. For example, we distributed the diluted sample to 96 wells for real-time PCR analysis to confirm that a usable dilution has been achieved. The dilution concentration may also be left as an unknown, thus removing this step as will be explained later.

In step 250, digital PCR is performed on each well of the array. For example, the same diluted sample was distributed to 384-wells for real-time PCR analysis. From the PCR results, an amount of markers for each nucleic acid sequence and the number of informative wells is identified. An informative well is defined as one that is only positive for the A or G allele but not both. In step 260, a calculation of an expected value of $P_r$ is performed. These steps will be described in more detail later. The calculation includes determining a parameter from values determined in step 250. For example, the actual average template concentration per well may be calculated.

In step 270, an SPRT or other likelihood-ratio test may be performed to determine whether or not an imbalance exists. For a euploid case, we expect an equal number of A-positive and G-positive wells. However, when template molecules from a trisomy 21 fetus are analyzed, the number of wells containing just one allele should be higher than that containing just the other allele. In short, allelic imbalance is expected for trisomy 21.

As mentioned above, SPRT is a Bayesian-type likelihood method which allows two probabilistic hypotheses to be compared as data accumulate. In digital PCR analysis for trisomy 21 detection, the alternative hypothesis is accepted when allelic imbalance exists (i.e. trisomy 21 detected); and the null hypothesis is accepted when there is no allelic imbalance (i.e. trisomy 21 not detected). The allele with the higher number of counts is referred as the potentially overrepresented allele and its proportion among all informative wells ($P_r$) would be calculated. SPRT is applied to determine if the $P_r$ indicates sufficient degree of allelic imbalance that would be expected for a trisomy 21 sample.

Figure 3:
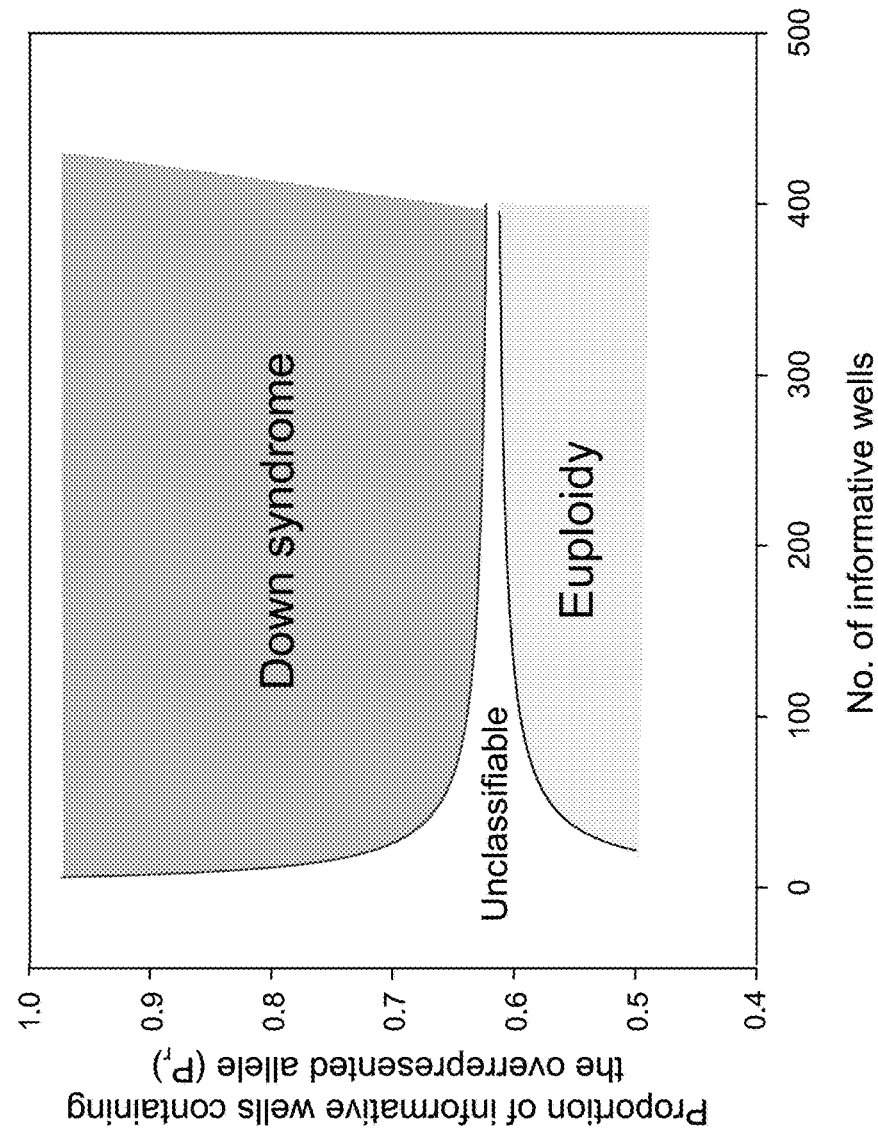
FIG. 3 illustrates a graph having SPRT curves used to determine Down syndrome according to an embodiment of the present invention.

Operationally, SPRT can be applied and interpreted through the use of graphs with a pair of SPRT curves that are constructed to define the probabilistic boundaries for accepting or rejecting either hypothesis. FIG. 3 illustrates a graph having SPRT curves for determining Down syndrome according to an embodiment of the present invention. The SPRT curves plot the required proportion of informative wells positive for the potentially overrepresented allele $P_r$, (y-axis) for a given total number of informative wells (x-axis) when confident classification could be made. As depicted in FIG. 3, the upper curve sets the probabilistic boundaries for accepting the alternative hypothesis; while the lower curve sets the probabilistic boundaries for accepting the null hypothesis.

The experimentally derived $P_r$ value would be compared with the expected value of $P_r$ to accept or reject either hypothesis. If the null hypothesis was accepted, the samples were classified as having been obtained from pregnant women with euploid fetuses. If the alternative hypothesis was accepted, the samples were classified as having been obtained from pregnant women with trisomy 21 fetuses. Alternatively, either hypothesis could not be accepted if the $P_r$ for the given number of informative counts has not yet reached the required level of statistical confidence for disease classification. These cases were deemed unclassifiable until more data were available. If disease classification is not possible, additional 384-well plates may be performed until the aggregated data become classifiable by SPRT.

SPRT thus offers the advantage that a smaller amount of testing is required for a given level of confidence than other statistical methods. In practical terms, SPRT allows the acceptance or rejection of either of the hypotheses as soon as the required amount of data has been accumulated and thus minimizes unnecessary additional analyses. This feature is of particular relevance to the analysis of plasma nucleic acids which are generally present at low concentrations where the number of available template molecules is limiting. In addition to a strict classification, the classification may also include a percent accuracy. For example, a classification resulting from a comparison with a cutoff value may provide that a sample shows a likelihood of a nucleic acid sequence imbalance with a certain percentage, or equivalently that determined imbalance is accurate to a certain percentage or other value.

A similar approach could be applied to determine the genotype of a fetus with regard to either a mutation or genetic polymorphism, using fetal nucleic acids in maternal plasma or serum. One should recall that a fetus would inherit half of its genome from its mother. As an illustration, consider a particular genetic locus with two alleles, A and B. If the mother is a heterozygote with a genotype of AB, the fetus could theoretically have a genotype of AA, BB or AB. If the fetus has a genotype of AB, i.e., the same as that of the mother, then there will only be nucleic acids of the AB genotype (from both the mother and fetus) in maternal plasma. Thus, nucleic acid or allelic balance is seen in maternal plasma. On the other hand, if the fetus has a genotype of AA or BB, then there would be allelic imbalance with an overrepresentation of the A or the B allele, respectively, in maternal plasma. This consideration is also applicable to disease-causing mutations (e.g. those causing cystic fibrosis or beta-thalassemia or spinal muscular atrophy), in which case A could be considered as the wildtype allele and B could be considered as the mutant allele.

II. Digital RCD

A disadvantage of digital RNA-SNP is that it can only be applied to cases heterozygous for the analyzed SNP. One improvement is that it would be ideal if a noninvasive test for detecting fetal trisomy 21 or other fetal chromosomal aneuploidies (e.g. trisomy 18, 13, and the sex chromosome aneuploidies) based on circulating fetal nucleic acid analysis were independent of the use of genetic polymorphisms. Thus, in one embodiment, chromosome dosage is determined by digital PCR analysis of a non-polymorphic chromosome 21 locus relative to one located on a reference chromosome, namely chromosome 1 in this study. A change of the ratio of chromosome 21 to chromosome 1 from 2:2 in the genome of a euploid fetus is differentiated from a trisomy 21 case. In digital PCR analysis for trisomy 21 detection, the two hypotheses to be compared would be the null hypothesis that there is no chromosomal imbalance (i.e. trisomy 21 not detected) and the alternative hypothesis that a chromosomal imbalance exists (i.e. trisomy 21 detected).

This approach can be generalized to the other chromosomes involved in other chromosomal aneuploidies, e.g. chromosome 18 in trisomy 18, chromosome 13 in trisomy 13, chromosome X in Turner syndrome. In addition, apart from chromosome 1, other chromosomes not involved in the aneuploidies concerned can also be used as a reference chromosome. A similar approach can also be applied to the detection of cancer, by analyzing the change of ratio of a chromosome commonly deleted, in part, in cancer, to a reference chromosome. Examples of the former include chromosome 5q in colorectal cancer, chromosome 3p in lung cancer and chromosome 9p in nasopharyngeal carcinoma. FIG. 2B lists some common cancer-related chromosomal aberrations which result in sequence imbalance.

FIG. 2A also illustrates a digital RCD method 205 according to an embodiment of the present invention. In one embodiment for steps 220-230, extracted DNA is quantified, for example, via Nanodrop techniques and diluted to a concentration of approximately one target template from either chromosomes 21 or the normalizing chromosome (such as chromosome 1) per well. In one embodiment in step 240, the confirmation may be performed by analyzing the diluted DNA sample by the assay using the chromosome 1 probe only in a 96-well format to confirm if ~37% level of the wells were negative before proceeding to digital RCD analysis using both TaqMan probes in 384-well plates. The significance of the 37% will be described later in Section IV.

The testing of step 240 and results of step 250 may be done with a real-time PCR assay designed to amplify a paralogous sequence (Deutsch, S. et al. 2004 *J Med Genet* 41, 908-915) present on both chromosomes which are distinguished by paralogous sequence variations that are discriminated by a pair of TaqMan probes. In this context, an informative well is defined as one that is positive for either the chromosome 21 or chromosome 1 locus but not both. For a euploid fetus, the number of informative wells positive for either locus should be approximately equal. For a trisomy 21 fetus, there should be an overrepresentation of wells positive for chromosome 21 than chromosome 1. The exact proportion of the overrepresentation is described in the following sections.

III. Incorporating Percentage of Fetal Sequences

A disadvantage of embodiments of methods 200 and 205 described above is that fetal specific markers are required. Accordingly, in one embodiment of the present invention, non-fetal specific markers are used. In order to use such non-fetal specific markers, embodiments of the present invention measure the fractional concentration of fetal DNA in the maternal plasma (i.e. the biological sample). With such information, a more useful value of $P_r$ may be calculated as follows.

Even with the small fractional percentage of fetal DNA in maternal plasma, a trisomy 21 fetus would contribute an additional dose of chromosome 21 sequences per genome-equivalent (GE) of fetal DNA released into maternal plasma. For example, a maternal plasma sample from a euploid pregnancy containing 50 GE/ml of total DNA with 5 GE/ml DNA contributed by the fetus (i.e. 10% fetal DNA fractional concentration) should contain a total of 100 copies (90 maternal copies +10 fetal copies) of chromosome 21 sequences per milliliter of maternal plasma. For a trisomy 21 pregnancy, each fetal GE would contribute three copies of chromosome 21, resulting in a total of 105 copies/ml (90 maternal copies +15 fetal copies) of chromosome 21 sequences in maternal plasma. At 10% fetal DNA concentration, the amount of chromosome 21 derived sequences in the maternal plasma of a trisomic pregnancy would therefore be 1.05 times that of a euploid case. Thus, if an analytical approach could be developed to determine this small degree of quantitative difference, a polymorphism-independent test for noninvasive prenatal diagnosis of fetal trisomy 21 would be achieved.

Accordingly, the degree of overrepresentation would be dependent on the fractional fetal DNA concentration in the analyzed DNA sample. For example, when placental DNA is analyzed, the theoretical RCD ratio in the fetal genome should be 3:2, i.e. 1.5-fold difference. However, as described above, the theoretical RCD ratio would decrease to 1.05 when a maternal plasma sample containing 10% fetal DNA is analyzed. The experimentally derived $P_r$ is calculated by dividing the number of wells positive only for the chromosome 21 locus by the total number of informative wells. The experimentally derived $P_r$ is subjected to the SPRT analysis with the calculated $P_r$ and the theoretical RCD ratio.

Figure 4:
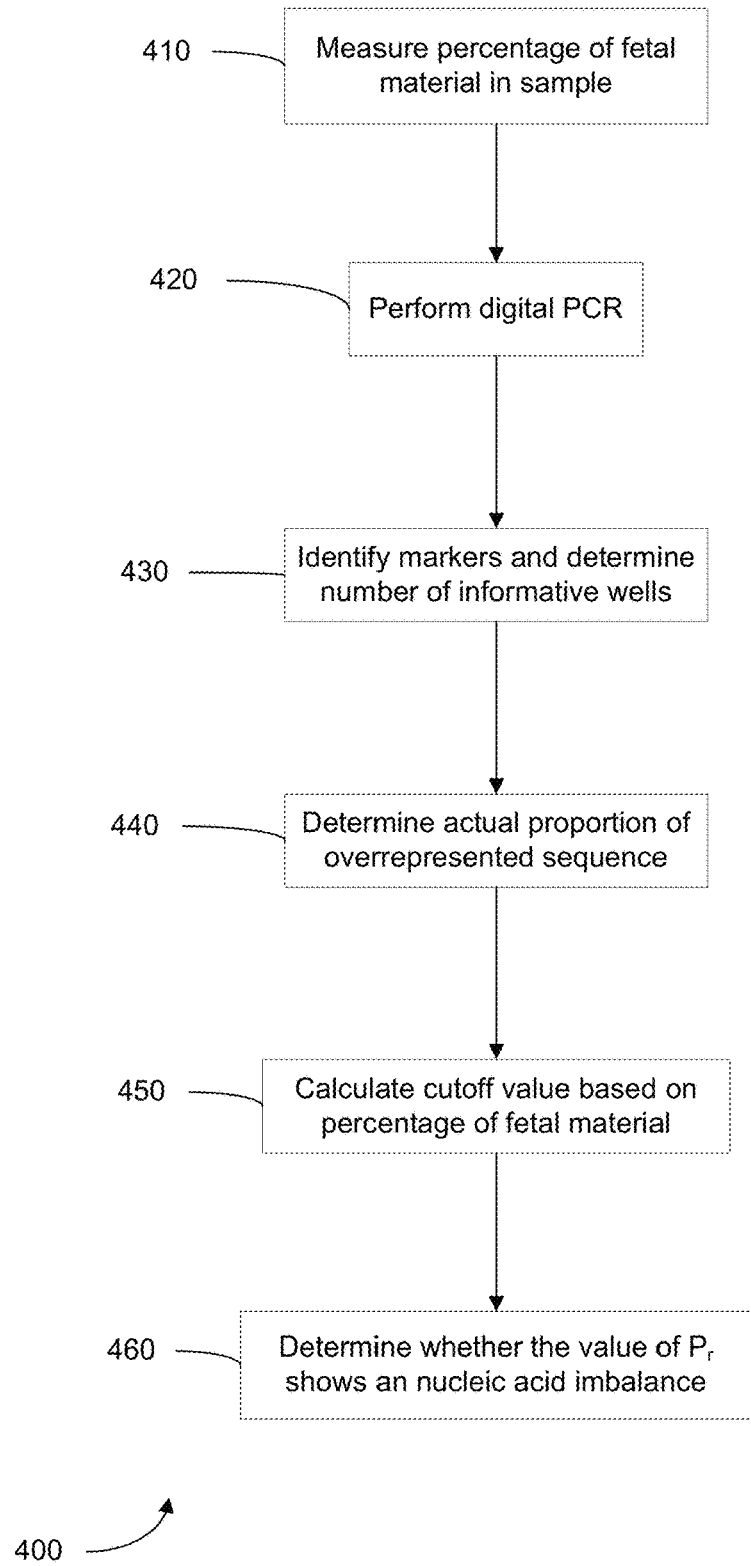
FIG. 4 shows a method of determining a disease state using a percentage of fetal cells according to an embodiment of the present invention.

FIG. 4 shows a method 400 of determining a disease state using a percentage of fetal nucleic acids according to an embodiment of the present invention. In step 410, the fractional percentage of fetal material is measured. In one embodiment, the fractional percentage is determined by measuring the amount of a fetal-specific marker (e.g. Y-chromosome, genetic polymorphism markers (e.g. SNPs), placental epigenetic signatures) in relation to a non-fetal-specific marker (i.e. gene sequence present in both mother and fetus). The actual measurement could be done by real-time PCR, digital PCR, sequencing reactions (including massively parallel genomic sequencing) or any other quantitative methods. In one aspect, it is preferable not to use the gene target that could potentially be in allelic imbalance for this measurement.

In step 420, digital PCR or other measurement method is performed, including diluting the sample, placing the diluted sample in the wells, and measuring the reactions in each well. In step 430, the PCR results are used to identify markers of different reference nucleic acid sequences (such as chromosomes or alleles). In step 440, the actual proportion ($P_r$) of the overrepresented sequence is calculated. In step 450, the cutoff value for determining a disease state is calculated using the percentage of fetal material in the sample. In step 460, from the actual $P_r$ and the cutoff value, it is determined whether an imbalance exists.

In one embodiment, the fractional percentage of reference nucleic acid sequences is incorporated in a digital RNA-SNP method. Thus, when investigating a LOH due to cancer cells, this can be done with tumor samples with less than 50% cancer cells. It also may be used on samples with greater than 50% cancer cells to obtain a more accurate $P_r$ and thus reduce the number of false positives, which would lead to incorrect diagnoses. In another embodiment, the fetal nucleic acid percentage is incorporated in a digital PCR method to determine if a fetus has inherited a parental gene mutation (e.g. that causing cystic fibrosis or beta-thalassemia or spinal muscular atrophy) or polymorphism from maternal plasma nucleic acid analysis.

IV. Incorporating Average Concentration Per Well

Another disadvantage of previous methods (e.g. Zhou, W. et al. 2002, supra) is that the average concentration of templates per well (in) is required to be 1 per well. Given that it is difficult to obtain an exact concentration, this can lead to inaccuracies. Furthermore, even with an exact concentration of 1 template per well, previous methods have ignored the statistical distribution of the templates in a well. In the previous methods, i.e. the old algorithm, the expected value of $P_r$ for accepting the alternative hypothesis is assumed to be the allelic ratio and, thus, is independent of the average concentration of the template DNA per well.

However, due to a natural statistical variation of the templates in the diluted sample, there will not be exactly 1 template per well. Embodiments of the present invention measure the average concentration of at least one of the sequences, which is then used to calculate the cutoff value, i.e. the expected $P_r$. In one aspect, this calculation involves a statistical distribution to determine a probability of a well containing the different nucleic acid sequences, which is then used to determine the expected $P_r$.

In one embodiment, the average concentration is taken of one reference nucleic acid sequence, which in one instance is nucleic acid sequence with the lower concentration in the DNA sample. In the case of a sample without an imbalance, the concentrations of the two sequences in the sample would be the same and either one can be regarded as the reference allele. In the case of a sample with, for example, LOH, the allele which is deleted in the cancer cells would be regarded as the reference allele. The average concentration of the reference allele would be denoted as $m_r$. In another embodiment, the sequence with the higher concentration may be taken as the reference sequence.

A. Digital-SNP. Example Using SPRT and Digital PCR

Figure 5:
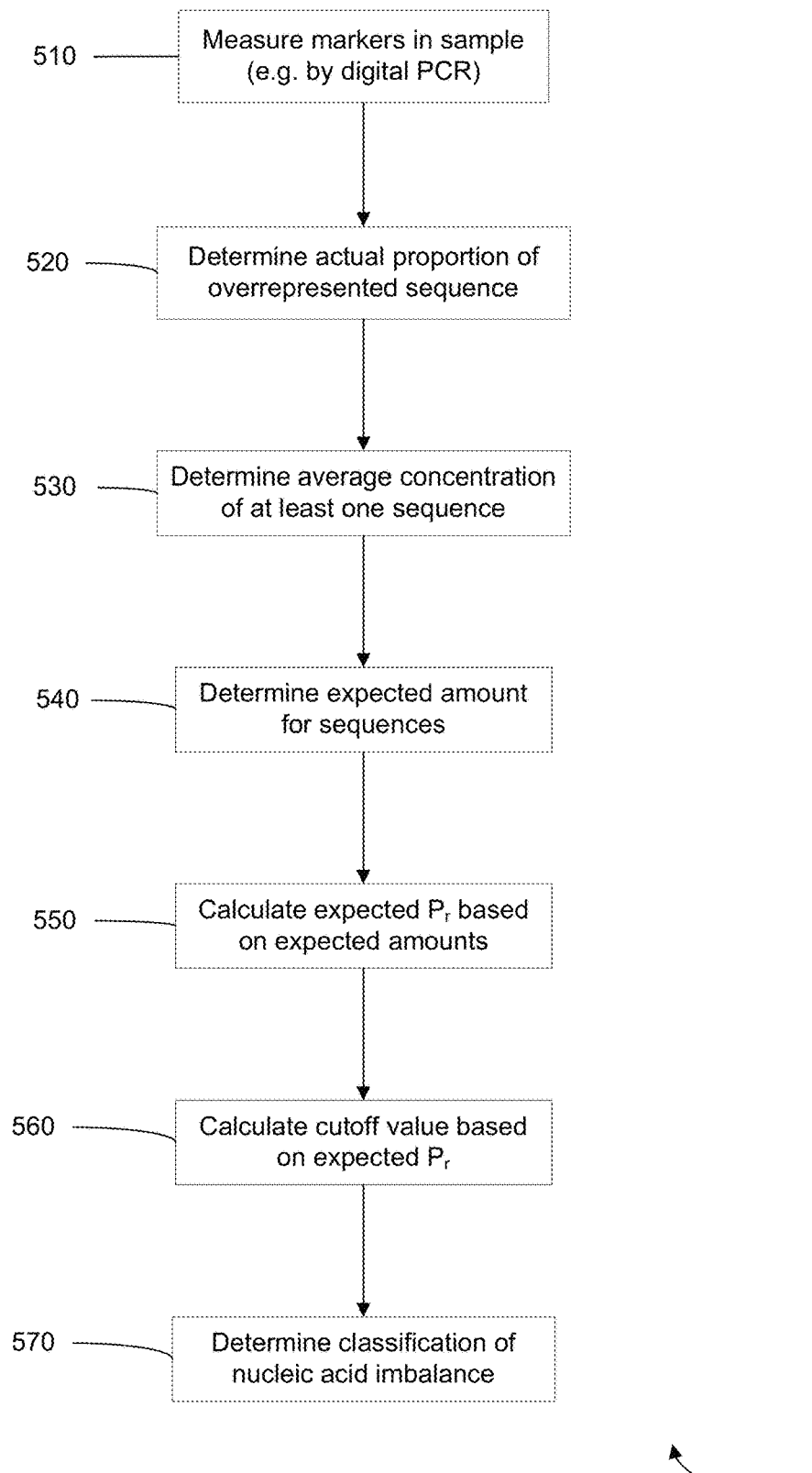
FIG. 5 shows a method of determining a disease state using an average concentration according to an embodiment of the present invention.

FIG. 5 shows a method 500 of determining a disease state using an average template concentration according to an embodiment of the present invention. In step 510, an amount of the different sequences are measured. This may be done for example by counting the makers in a digital PCR experiment as explained above. However, it may be done by other methods that do not involve an amplification step or that do not use a fluorescent marker, but could use other properties, such as physical properties like mass, specific optical properties or base-pairing properties.

In step 520, the actual proportion of the overrepresented sequence is determined. This may be done as described above by taking the number of wells showing only that sequence and dividing by the number of informative wells. In step 530, the average concentration of at least one of the sequences is measured (the reference sequence). In one embodiment, the reference sequence is the overrepresented sequence. In another embodiment, the reference sequence is the underrepresented sequence. The measurement may be done by counting the number of wells negative for the reference sequence in the digital PCR experiment. The relationship between the proportion of negative wells and the average template concentration is described by the Poisson distribution as described in the next subsection.

In step 540, an expected amount of wells positive for the different sequences is calculated, for example, using a Poisson distribution. The expected amount may be as a probability of the sequence per well, an average sequence per well, the number of wells containing the sequence or any other suitable quantity. In step 550, the expected $P_r$ is calculated from the expected amounts. In step 560, a cutoff value is calculated from the expected $P_r$, for example, by using SPRT. In step 570, a classification of the nucleic acid sequence imbalance is determined. Specific aspects of method 500 are now described.

1. Determining Expected Amount of Sequences

Once the average concentration per well (reaction or reaction mixture) is known from step 530, the expected number of wells showing that sequence may be calculated in step 540. This amount may be expressed as a %, a fractional value, or an integer value. Using a specific example for illustration, assume the average concentration of the reference template per well ($m_r$) is 0.5 per well and the genotype of the trisomy 21 fetus at the PLAC4 SNP, rs8130833, is AGG. Therefore, the reference template would be the A allele and the overrepresented template would be the G allele.

In one embodiment, a Poisson distribution is assumed for the distribution of the A allele among the reaction mixtures of the wells of the measurement procedure, such as digital PCR. In other embodiments, other distribution functions are used, such as binomial distribution.

The Poisson equation is:

$$P(n) = \frac{m^n e^{-m}}{n!}$$

where, n=number of template molecules per well; P(n)-probability of n template molecules in a particular well; and m=average number of template molecules in one well in a particular digital PCR experiment.

Accordingly, the probability of any well not containing any molecule of the A allele at an average A-allele concentration of 0.5 would be:

$$P(0) = \frac{0.5^0 e^{-0.5}}{0!} = e^{-0.5} = 0.6065.$$

Hence, the probability of any well containing at least one molecule of the A allele would be: 1−0.6065=0.3935. Therefore, ~39% of the wells would be expected to contain at least one molecule of the A allele.

As for the non-reference nucleic acid sequence, for each cell of a trisomy 21 fetus, the genomic ratio of A to G would be 1:2. Assuming that the A to G ratio in the extracted RNA or DNA sample would remain unchanged, the average concentration of the G allele per well would be two times that of the A allele, i.e. 2×0.5=1.

Accordingly, the probability of any well not containing any molecule of the G allele at an average G-allele concentration of 1 would be:

$$P(0) = \frac{1^0 e^{-1}}{0!} = e^{-1} = 0.3679$$

Hence, the probability of any well containing at least one molecule of the G allele would be: 1−0.3679=0.6321. Therefore, ~63% of the wells would be expected to contain at least one molecule of the G allele.

2. Determining Proportion of Overrepresented Sequence

After the expected amounts are calculated, the proportion of the overrepresented nucleic acid sequence may be determined. Assuming that the filling of the wells with the A allele and the G allele are independent, the probability of a well containing both alleles would be 0.3935×0.6321=0.2487. Therefore, ~25% of the wells would be expected to contain both alleles.

The proportion of wells expected to contain the A allele but not the G allele would be the number of wells containing at least one A allele deducted by the number of wells containing both the A and G alleles: 0.3935−0.2487=0.1448. Similarly, the proportion of wells expected to contain the G allele but not the A allele would be: 0.6321−0.2487=0.3834. An informative well is defined as a well being positive for either the A allele or the G allele but not both.

Hence, the expected ratio of wells containing the A allele relative to the G allele in a digital RNA-SNP analysis is 0.1448/0.3834. In other words, the proportion of wells positive only for the G allele is 2.65 times that of wells positive only for the A allele. This is in contrast to the fetal genomic ratio where the overrepresented allele is 2 times that of the other allele.

For SPRT analysis, the proportion of the informative wells positive for the overrepresented allele ($P_r$) is calculated and interpreted using SPRT curves. In the current example, the proportion of informative wells would be: 0.1448+0.3834=0.5282. Hence, the expected $P_r$ of a trisomy 21 case at $m_r$ 0.5 is: 0.3834/0.5282=0.73.

As the average template concentration (m) is a key parameter in the Poisson equation, the $P_r$ would vary with m. FIG. 6 shows a table 600 that tabulates the expected digital RNA-SNP allelic ratio and $P_r$ of trisomy 21 samples for a range of template concentrations expressed as the average reference template concentration per well ($m_r$) according to an embodiment of the present invention. Table 600 shows the expected allelic ratio and proportion of informative wells positive for the overrepresented allele ($P_r$) for a series of average reference template concentrations per well ($m_r$).

The expected value of $P_r$ varies with the average concentration of the reference allele per well ($m_r$) in a non-linear fashion. As shown in table 600, the expected value of $P_r$ for accepting the alternative hypothesis would increase with $m_r$. As the expected value of $P_r$ for accepting the null hypothesis is fixed at 0.5, the samples with and without allelic imbalance would separate more widely in terms of the value of $P_r$ when $m_r$ increases. Note that in other embodiments the value for accepting the null hypothesis may be other than 0.5. This might occur when the normal ratio is different than 1:1, e.g., 5:3, and thus an imbalance would occur when the ratio deviates from 5:3. The difference in the amounts of the two different nucleic acid sequences would then be determined on a case by case basis.

However, as previous methods (e.g., Zhou, W. et al. 2002, supra) used a fixed expected value of $P_r$ for LOH samples, they underestimated the value of $P_r$ for those samples with LOH (alternative hypothesis accepted). The degree of underestimation would increase with $m_r$. In other words, the higher the average concentration of the reference allele in the DNA sample, the more inaccurate the old methods would be. This underestimation of $P_r$ for accepting the alternative hypothesis would lead to the inaccurate calculation of the cutoff values for accepting both the null and alternative hypotheses.

3. Calculating Cutoff Values Based on Expected $P_r$

For embodiments using SPRT, one may use the equations for calculating the upper and lower boundaries of the SPRT curves from El Karoui at al. (2006). Furthermore, the level of statistical confidence preferred for accepting the null or alternative hypothesis could be varied through adjusting the threshold likelihood ratio in the equations. In this study, a threshold likelihood ratio of 8 is used because this value had been shown to provide satisfactory performance to discriminate samples with and without allelic imbalance in the context of cancer detection. Thus, in one embodiment, the equations for calculating the upper and lower boundaries of the SPRT curves are:

Upper boundary=$[(\ln 8)/N - \ln \delta]/\ln \gamma$

Lower boundary=$[(\ln 1/8)/N - \ln \delta]/\ln \gamma$ where, $\delta = (1-\theta_1)/(1-\theta_0)$
$\gamma = -(\theta_1(1-\theta_0)/\theta_0(1-\theta_1))$
$\theta_0$=proportion of informative wells containing the non-reference allele if the null hypothesis is true
=0.5 (see below)
$\theta_1$=proportion of informative wells containing the non-reference (i.e. overrepresented) allele if the alternative hypothesis is true
N=number of informative wells
=number of wells positive for either allele only
(ln is a mathematical symbol representing the natural logarithm, i.e. $\log_e$.)

For the determination of $\theta_0$ for accepting the null hypothesis, the sample is assumed to be obtained from a pregnant woman carrying a euploid fetus. Under this assumption, the expected number of wells positive for either template would be 1:1, and thus the expected proportion of informative wells containing the non-reference allele would be 0.5.

For the determination of $\theta_1$ for accepting the alternative hypothesis, the sample is assumed to be obtained from a pregnant woman carrying a trisomy 21 fetus. The calculations for the expected $P_r$ of trisomy 21 cases for digital RNA-SNP analysis are detailed in Table 600. Hence, $\theta_1$ for digital RNA-SNP analysis refers to the data shown in the last column of table 600.

4. Measurement of Average Concentration

The measurement of $m_r$ may be performed through a variety of mechanisms as known or will be known to one skilled in the art. In one embodiment, the value of $m_r$ is determined during the experimental process of digital PCR analysis. As the relationship between the value of $m_r$ and the total number of wells being positive for the reference allele can be governed by a distribution (e.g. the Poisson distribution), $m_r$ can be calculated from the number of wells being positive for the reference allele using this formula:

$$m_r = -\ln(1-\text{proportion of wells being positive for the reference allele})$$

Note that ln is the natural logarithm, i.e., $\log_e$. This approach provides a direct and precise estimation of $m_r$ in the DNA sample used for the digital PCR experiment.

This method may be used to achieve a desired concentration. For example, the extracted nucleic acids of a sample may be diluted to a specific concentration, such as one template molecule per reaction well, as done in step 240 of method 200. In an embodiment using the Poisson distribution, the expected proportion of wells with no template may be calculated as $e^{-m}$, where m is the average concentration of template molecules per well. For example, at an average concentration of one template molecule per well, the expected proportion of wells with no template molecule is given by $e^{-1}$, i.e., 0.37 (37%). The remaining 63% of wells will contain one or more template molecules. Typically, the number of positive and informative wells in a digital PCR run would then be counted. The definition of informative wells and the manner by which the digital PCR data are interpreted depends on the application.

In other embodiments, the average concentration per well, $m_r$, is measured by another quantification method, for example, quantitative real-time PCR, semi-quantitative competitive PCR, real-competitive PCR using mass spectrometric methods, etc.

B. Digital RCD

Digital RCD using the average concentration may be performed in a similar manner to the digital SNP method described above. The numbers of wells positive for the reference chromosome (non-chromosome 21) marker, the chromosome 21 marker and both markers can be determined by digital PCR. The average concentration of the reference marker per well ($m_r$) can be calculated from the total number of wells negative for the reference marker, irrespective of the positivity of the chromosome 21 marker, according to the Poisson probability function as in the calculation of $m_r$ for the digital SNP analysis.

SPRT analysis may then be used for classifying a plasma sample as being obtained from a pregnant woman carrying a euploid or a trisomy 21 fetus. The null hypothesis would be accepted when the fetus was euploid. In this scenario, the expected ratio for the wells positive for the reference marker and chromosome 21 marker would be 1:1 and, thus, the expected proportion of informative wells with positive signal for chromosome 21 marker would be 0.5. The alternative hypothesis would be accepted when the fetus was trisomic for chromosome 21. In this scenario, if the sample DNA was solely derived from the fetus, the average concentration of the chromosome 21 marker in each well would be 3/2 times the average concentration of the reference marker ($m_r$).

While digital RCD may be used to determine chromosome dosage through the detection of fetal-specific markers, e.g. epigenetic signatures of the placenta (Chim, S S C. et al. 2005 *Proc Natl Acad Sci USA* 102, 14753-14758), an embodiment of the digital RCD analysis uses non-fetal-specific markers. Thus, an additional step of measuring the percentage of fetal material would occur when non-fetal specific markers are used. Therefore, the average concentration of the chromosome 21 marker per well would be dependent on the proportion of the fetal DNA in the sample and can be calculated using: $m_r$ [(200%+fetal DNA percentage)/200%].

Again using a specific example for illustration, the average concentration of the reference template, chromosome 1, per well ($m_r$) is assumed to be 0.5 and 50% of the DNA is assumed to be derived from the fetus and 50% of the DNA in the sample is derived from the mother.

Accordingly, using the Poisson distribution, the probability of any well not containing any molecule of the chromosome 1 locus when its average concentration is 0.5 per well would be:

$$P(0) = \frac{0.5^0 e^{-0.5}}{0!} = e^{-0.5} = 0.6065$$

Hence, the probability of any well containing at least one molecule of the chromosome 1 locus would be: 1−0.6065=0.3935. Therefore, ~39% of the wells would be expected to contain at least one molecule of the locus.

For each cell of this trisomy 21 fetus, the genomic ratio of chromosome 21 to chromosome 1 would be 3:2. The ratio between chromosome 21 and chromosome 1 in the DNA sample would be dependent on the fractional fetal DNA concentration (fetal DNA %) and would be: 3× fetal DNA %+2 (1−fetal DNA %): 2× fetal DNA %+2×(1−fetal DNA %). Thus, in this case when the fractional fetal DNA concentration is 50%, the ratio would be: (3×50%+2×50%)/(2×50%+2×50%)=1.25. If the digital SNP method did not use fetal specific markers, such a calculation could also be used to calculate the average concentration of the non-reference sequence.

Hence, when the average concentration of the chromosome 1 locus per well is 0.5, the average concentration of the chromosome 21 locus per well is: 1.25×0.5=0.625. Accordingly, the probability of any well not containing any molecule of the chromosome 21 locus when its average concentration is 0.625 per well would be:

$$P(0) = \frac{0.625^0 e^{-0.625}}{0!} = e^{-0.625} = 0.5353$$

Hence, the probability of any well containing at least one molecule of the chromosome 21 locus would be: 1−0.5353=0.4647. Therefore, ~46% of the wells would be expected to contain at least one molecule of the locus. Assuming that the filling of the wells with either loci are independent, the probability of a well containing both loci would be 0.3935×0.4647=0.1829. Therefore, ~18% of the wells would be expected to contain both loci.

The proportion of wells expected to contain the chromosome 1 locus but not the chromosome 21 locus would be the number of wells containing at least one chromosome 1 locus deducted by the number of wells containing both loci: 0.3935−0.1829=0.2106. Similarly, the proportion of wells expected to contain the chromosome 21 locus but not both loci would be: 0.4647−0.1829=0.2818. An informative well is defined as a well positive for either the chromosome 1 locus or the chromosome 21 locus but not both.

Hence, the expected chromosome 21 to chromosome 1 ratio in digital RCD analysis is 0.2818/0.2106=1.34. In other words, the proportion of wells positive only for the chromosome 21 locus is 1.34 times that of wells positive only for the chromosome 1 locus. This is in contrast to the ratio of 1.25 in the DNA sample.

For SPRT analysis, the proportion of the informative wells positive for the chromosome 21 locus ($P_r$) would need to be calculated and interpreted using SPRT curves. In the current example, the proportion of informative wells would be: 0.2106+0.2818=0.4924. Hence, the expected Pr of a trisomy 21 case with 50% fetal DNA at $m_r$ 0.5 is: 0.2818/0.4924=0.57.

Figure 7:
FIG. 7 shows a table that tabulates the expected $P_r$ for the fractional fetal DNA concentrations of 10%, 25%, 50% and 100% in trisomy 21 samples at a range of template concentrations expressed as the average reference template concentration per well ($m_r$) according to an embodiment of the present invention.

As the average template concentration (m) is a key parameter in the Poisson equation, the $P_r$ would vary with m. FIG. 7 shows a table 700 that tabulates the expected $P_r$ for the fractional fetal DNA concentrations of 10%, 25%, 50% and 100% in trisomy 21 samples at a range of template concentrations expressed as the average reference template concentration per well ($m_r$) according to an embodiment of the present invention. The calculations for the expected $P_r$ of trisomy 21 cases for digital RCD analyses are detailed in table 700. Hence, $\theta_1$ for digital RCD analysis of samples with varying fetal DNA fractional concentrations can be obtained from the columns showing the corresponding expected $P_r$-values in table 700.

C. Results

1. Comparison of Different $m_r$

The basis for the difference between the theoretical (as in the fetal genome) and experimentally-expected degree of allelic or chromosomal imbalance and the calculations to determine the latter for a range of $m_r$ values are shown in tables 600 and 700. In digital RNA-SNP analysis of a trisomy 21 sample, when $m_r$-0.5, wells containing just the overrepresented allele with respect to wells containing just the reference allele, namely the digital RNA-SNP ratio, is 2.65 (table 600). In digital RCD analysis of a specimen composed of 100% fetal DNA, when $m_{r=0.5}$, wells positive solely for the chromosome 21 locus with respect to those positive solely for the chromosome 1 locus, namely the digital RCD ratio, is 1.7 (table 700) ($P_r$=0.63, thus the digital RCD ratio is 0.63/(1−0.63)=1.7). As the fractional fetal DNA concentration decreases, the digital RCD ratio decreases for the same $m_r$ (table 700).

As shown in tables 600 and 700, the extent of allelic or chromosomal overrepresentation increases with $m_r$. However, the percentage of informative wells approaches its maximum around $m_r$=0.5 and decreases gradually with further increase in $m_r$. In practice, the decline in the proportion of informative wells could be compensated by increasing the total number of wells analyzed if the amount of template molecule for the specimen is not limiting, but additional wells would require an increase in reagent costs. Hence, optimal digital PCR performance is a trade-off between the template concentration and total number of wells tested per sample.

2. Example Using SPRT Curves

As discussed above, the expected degree of allelic or chromosomal imbalance for a digital PCR experiment is dependent on the actual template concentration per reaction mixture (e.g. a well). We describe the template concentration based on the reference allele, i.e. the average reference template concentration per well ($m_r$). As shown in the above equation, the expected $P_r$ can be used to determine the plotting of the upper and the lower SPRT curves. Since the expected $P_r$ is in turn dependent on the value of $m_r$, the plotting of the SPRT curves would essentially be dependent on the value of $m_r$. Thus, in practice, a set of SPRT curves relevant for the actual $m_r$ of a digital PCR dataset would need to be used for the interpretation of the $P_r$ from that particular run.

Figure 8:
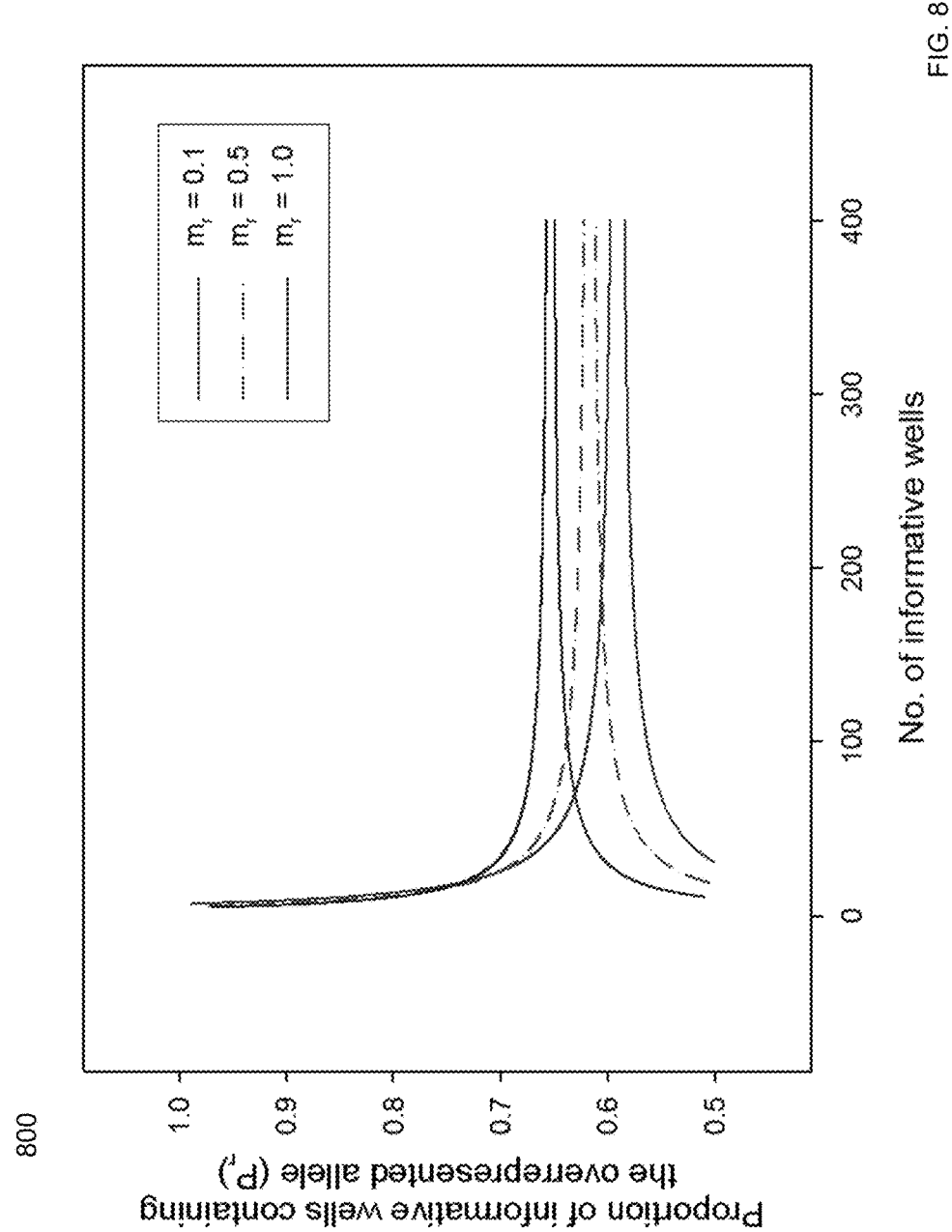
FIG. 8 shows a plot illustrating the degree of differences in the SPRT curves for $m_r$ values of 0.1, 0.5 and 1.0 for digital RNA-SNP analysis according to an embodiment of the present invention.

FIG. 8 shows a plot 800 illustrating the degree of differences in the SPRT curves for $m_r$ values of 0.1, 0.5 and 1.0 for digital RNA-SNP analysis according to an embodiment of the present invention. Each set of digital PCR data should be interpreted with the specific curves relevant to the exact $m_r$ value of that particular run. Note that since the expected degree of allelic or chromosomal imbalance for the digital RNA-SNP and RCD approaches are different (2:1 for the former and 3:2 for the latter), different sets of SPRT curves are needed for the two digital PCR systems. The experimentally derived $P_r$ is interpreted with the relevant SPRT curves selected by the corresponding $m_r$ of the digital PCR run. This is in contrast to the previous reported use of SPRT for molecular detection of LOH by digital PCR where a fixed set of curves had been used.

The practical manner for interpreting the digital PCR data using SPRT is illustrated below using a hypothetical digital RNA-SNP run. After digital RNA-SNP analysis of each case, the number of wells positive for the A allele only, the G allele only or both alleles are counted. The reference allele is defined as the allele with the smaller number of positive wells. The value of $m_r$ is calculated using the total number of wells negative for the reference allele, irrespective of whether the other allele is positive, according to the Poisson probability density function. The data of our hypothetical example are as follows:

In a 96-well reaction, 20 wells are positive for the A allele only, 24 wells are positive for the G allele only, and 33 wells are positive for both alleles. The A allele is regarded as the reference allele because there are less A-positive than G-positive wells. The number of wells negative for the reference allele is 96−20−33=43. Therefore, $m_r$ can be calculated using the Poisson equation: −ln(43/96)=0.80. The experimentally determined $P_r$ of this case is: 24/(20+24)=0.55.

According to table 600, the expected $P_r$ of a trisomy 21 sample at $m_r$=0.8 is 0.76. Thus, $\theta_1$ is 0.76 for this case. The SPRT curves based on $\theta_1$=0.76 would be used to interpret the experimentally derived $P_r$ of this case which is 0.55. When $P_r$=0.55 is fitted onto the relevant SPRT curves, the data point falls under the lower curve. Hence, the case is classified as euploid, see FIG. 3.

3. Comparison to Old Method

FIG. 9A shows a table 900 of a comparison of the effectiveness of the new and old SPRT algorithms for classifying euploid and trisomy 21 cases in 96-well digital RNA-SNP analyses. FIG. 9B shows a table 950 of a comparison of the effectiveness of the new and old SPRT algorithms for classifying euploid and trisomy 21 cases in 384-well digital RNA-SNP analyses. The new algorithm refers to the selection of SPRT curves specific for the $m_r$ derived from the digital PCR data. The old algorithm refers to the use of a fixed set of SPRT curves for all digital PCR runs. The effect of incorrect calculation of the cutoff values on the accuracy of classification is revealed by the simulation analysis shown in table 900.

Compared with the use of a fixed set of SPRT curves in previous studies, the proportion of unclassifiable data is much lower with our approach, as shown in tables 900 and 950. For example, using our approach, at $m_r$=0.5, 14% and 0% of trisomy 21 samples would be unclassifiable for 96-well and 384-well digital RNA-SNP analyses, respectively, but 62% and 10%, respectively, with the use of fixed curves (Table 900). Hence, our approach allows disease classification with lesser number of informative wells.

As shown in table 900, the new algorithm is more accurate in classifying the samples as having or not having allelic ratio skewing for all values of $m_r$ from 0.1 to 2.0. For example, when $m_r$ equals 1.0 and a 96-well digital RNA-SNP run is performed, the new algorithm correctly classifies 88% and 92% of samples with and without allelic ratio skewing, respectively, whereas the percentage of correct classification of samples with and without allelic ratio skewing using the old algorithm is only 19% and 36%, respectively.

Using the new algorithm, the separation of samples with and without allelic ratio skewing would increase with $m_r$. As a result, the classification accuracies would increase with $m_r$. The effect of increase in separation of the two groups of samples on the classification accuracy would diminish when $m_r$ increases to beyond 2.0 because of the reduction in the percentage of informative wells. In contrast, using the old algorithm, the classification accuracies significantly reduce when $m_r$ increases because of the increased deviation of expected P value from its true value.

Our experimental and simulation data show that digital RNA-SNP is an effective and accurate method for trisomy 21 detection. As PLAC4 mRNA in maternal plasma is derived purely from the fetus, for 12 of the 13 maternal plasma samples tested, only one 384-well digital PCR experiment was required for correct classification (Table 1350 of FIG. 13B). This homogenous, real-time digital PCR-based approach thus offers an alternative to the mass spectrometry-based approach for RNA-SNP analysis (Lo, Y M D, et al. 2007 *Nat Med*, supra). Apart from placental-specific mRNA transcripts, we also envision that other types of fetal-specific nucleic acid species in maternal plasma could be used for digital PCR-based detection of fetal chromosomal aneuploidies. One example is fetal epigenetic markers (Chim, S S C et al. (2005) *Proc Natl Acad Sci U S A* 102, 14753-14758; Chan. K C A et al. (2006) *Clin Chem* 52, 2211-2218), which have recently been used for the noninvasive prenatal detection of trisomy 18 using the epigenetic allelic ratio (EAR) approach (Tong, Y K et al. (2006) *Clin Chem* 52, 2194-2202). Thus, we predict that digital EAR would be a possible analytical technique.

V. Increasing %, Multiple Markers, and PCR Alternatives

As described above, the application of embodiments of the present invention to DNA extracted from maternal plasma can be complicated when the fetal DNA only constitutes a minor fraction of maternal plasma DNA, with a mean fractional concentration of some 3% between weeks 11 and 17 of gestation. Nevertheless, as shown herein, digital RCD allows aneuploidy detection even when the aneuploid DNA is present as a minor population. With a decreasing fractional concentration of fetal DNA, such as may be present during early gestation, a larger number of informative counts is needed for digital RCD. A significance of the present work, as summarized in table 1200 of FIG. 12, is that we have provided a set of benchmark parameters, e.g. fractional fetal DNA and total template molecules required, which diagnostic assays can be built upon. In our opinion, 7680 total number of reactions for a fractional fetal DNA concentration of 25% is a particularly attractive set of benchmark parameters. These parameters should allow euploid and trisomy 21 samples to be classifiable correctly 97% of the time, as shown in table 1200.

The number of plasma DNA molecules that are present per unit volume of maternal plasma is limited (Lo, Y M D. et al. 1998 *Am J Hum Genet* 62, 768-7758). For example, in early pregnancy, the median maternal plasma concentration of an autosomal locus, the β-globin gene, has been shown to be 986 copies/mL, with contributions from both the fetus and mother (Lo, Y M D. et al. 1998 *Am J Hum Genet* 62, 768-7758). To capture 7,680 molecules, DNA extracted from some 8 mL of maternal plasma would be needed. This volume of plasma, obtainable from ~15 mL of maternal blood, is at the limit of routine practice. However, we envision that multiple sets of chr21 and reference chromosome targets can be combined for digital RCD analysis. For 5 pairs of chr21 and reference chromosome targets, just 1.6 mL of maternal plasma would be needed to provide the number of template molecules needed for analysis. Multiplex single molecule PCR could be performed. The robustness of such multiplex single molecule analysis has been demonstrated previously for single molecule haplotyping (Ding, C. and Cantor, C R. 2003 *Proc Natl Acad Sci USA* 100, 7449-7453).

Alternatively, to achieve a fractional fetal DNA concentration of 25%, methods may allow the selective enrichment of fetal DNA (Li, Y. et al. 2004 *Clin Chem* 50, 1002-1011) or the suppression of the maternal DNA background (Dhallan, R et al. 2004 *JAMA* 291, 1114-1119) or both, in maternal plasma. Apart from such physical methods for fetal DNA enrichment and maternal DNA suppression, it would also be possible to use a molecular enrichment strategy, such as by targeting fetal DNA molecules which exhibit a particular DNA methylation pattern (Chim, S S C et al, 2005 *Proc Nat Acad Sci USA* 102, 14753-14758, Chan, K C A et al. 2006 *Clin Chem* 52, 2211-2218; Chiu, R W K et al. 2007 *Am J Pathol* 170, 941-950.)

Additionally, there are now a number of alternative approaches to the manual set up of digital real-time PCR analyses as used in the current study for conducting digital PCR. These alternative approaches include microfluidics digital PCR chips (Warren, L et al. 2006 *Proc Natl Acad Sci USA* 103, 17807-17812; Ottesen, E A et al. 2006 *Science* 314, 1464-1467), emulsion PCR (Dressman. D et al. 2003 *Proc Natl Acad Sci U S A* 100, 8817-8822), and massively parallel genomic sequencing (Margulies, M. et al. 2005 *Nature* 437, 376-380) using for example the Roche 454 platform, the Illumina Solexa platform, and the SOLiD™ system of Applied Biosystems, etc. With regard to the latter, our method is also applicable to massively parallel sequencing methods on single DNA molecules, which do not require an amplification step, such as the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 *Clin Chem* 53, 1996-2001). With the use of these methods, digital RNA-SNP and digital RCD could be performed rapidly on a large number of samples, thus enhancing the clinical feasibility of the methods proposed here for noninvasive prenatal diagnosis.

EXAMPLES

The following examples are offered to illustrate, but not to limit the claimed invention.

I. Computer Simulations

Computer simulation was performed to estimate the accuracy of diagnosing trisomy 21 using the SPRT approach. The computer simulation was performed with the Microsoft Excel 2003 software (Microsoft Corp., USA) and SAS 9.1 for Windows software (SAS Institute Inc., NC, USA). The performance of digital PCR is an interplay between the reference template concentration ($m_r$), number of informative counts and projected degree of allelic or chromosomal imbalance ($P_r$). Separate simulations were performed for a range of each of these variables. Since the decision boundaries of the SPRT curves for digital RNA-SNP and digital RCD were different, the simulation analyses for the two systems were performed separately.

For each digital PCR condition simulated (i.e. $m_r$, fetal DNA fractional concentration, total well number), two rounds of simulation were performed. The first round simulated the scenario that the tested samples were obtained from pregnant women carrying euploid fetuses. The second round simulated the scenario when the tested samples were obtained from pregnant women carrying trisomy 21 fetuses. For each round, testing of 5000 fetuses was simulated.

A. RNA-SNP

For digital RNA-SNP, simulations of a 384-well experiment with $m_r$=0.1 to $m_r$=2.0 were performed. At each $m_r$ value, we simulated the scenario whereby 5000 euploid and 5000 trisomy 21 fetuses were tested. The SPRT curves appropriate for the given $m_r$ were used to classify the 10,000 fetuses. FIG. 10 is a table 1000 showing the percentages of fetuses correctly and incorrectly classified as euploid or aneuploid and those not classifiable for the given informative counts according to an embodiment of the present invention. The accuracies for diagnosing euploid and aneuploid cases are both 100%, for $m_r$ between 0.5 and 2.0. When $m_r$=0.1, only 57% and 88% of euploid and trisomy 21 fetuses could be accurately classified after the analysis of 384 wells.

The simulation data were generated as described in the following steps:

In step 1, for each well, two random numbers were generated using the Random(Poisson) function of the SAS program (www.sas.com/technologies/analytics/statistics/index.html) to represent the A and the G alleles, respectively. The Random(Poisson) function would generate positive integers starting from 0 (i.e. 0, 1, 2, 3, . . . ) and the probability of each integer being generated was dependent on the probability of this number according to the Poisson probability density function for a given mean value which represented the average concentration of the alleles per well. A well was regarded as positive for the A allele if the random number representing the A allele was larger than zero, i.e. contained 1 or more molecules of the A allele. Similarly, the well was regarded as positive for the G allele if the random number representing the G allele was larger than zero.

To simulate the scenario of a pregnant woman carrying a euploid fetus, the same mean value was used for generating the random numbers for the A allele and the G allele. For example, in the analysis simulating digital RNA-SNP analyses at $m_r$=0.5, the mean value for either the A allele of the G allele was set identically to 0.5 which meant an average concentration for either allele of 0.5 molecule per well. Using the Poisson equation, at a mean concentration of 0.5, the proportion of wells being positive for the A or the G alleles would be the same and was 0.3935, see table 600.

When simulating the digital RNA-SNP analysis of a pregnant woman with a trisomy 21 fetus at $m_r$=0.5, the average concentration of the overrepresented allele per well would be expected to be 2 times of that of the reference allele, i.e. 1. In this situation, the probability of a well being positive for the overrepresented allele was 0.6321, see table 600.

After generating a random number for a digital PCR well, the well could be classified as one of the following statuses:

a. negative for both the A and the G alleles
b. positive for both the A and the G alleles
c. positive for the A allele but negative for the G allele
d. positive for the G allele but negative for the A allele In step 2, step 1 was repeated until the desired number of wells, 384 wells for the current simulation, had been generated. The numbers of wells positive for the A allele only and the G allele only were counted. The allele with less positive wells was regarded as the reference allele and the allele with more positive wells was regarded as the potentially overrepresented allele. The number of the informative wells was the total number of wells positive for either allele but not both. The proportion of informative wells containing the potentially overrepresented allele ($P_r$) was then calculated. The upper and lower boundaries for the relevant SPRT curves to accept the null or alternative hypothesis were calculated according to an embodiment of the present invention.

In step 3, 5000 simulations were performed for each of the two scenarios of the pregnant woman carrying a euploid or a trisomy 21 fetus. Each simulation could be regarded as an independent biological sample obtained from pregnant women. In Table 1000, the correct classification of euploid cases refers to those euploid cases in which the null hypothesis was accepted and the incorrect classification of euploid cases refers to those euploid cases in which the alternative hypothesis was accepted. Similarly, those trisomy 21 cases in which the alternative hypothesis was accepted were regarded as correctly classified and those trisomy 21 cases in which the null hypothesis was accepted were regarded as incorrectly classified. For both groups, those cases in which neither the null or alternative hypothesis was accepted after the pre-specified total number of wells had been simulated were regarded as unclassified.

In step 4, steps 1 to 3 were performed for $m_r$ ranging from 0.1 to 2.0 at increments of 0.1.

B. RCD

FIG. 11 is a table 1100 showing computer simulations for digital RCD analysis for a pure (100%) fetal DNA sample for $m_r$ ranging from 0.1 to 2.0 according to an embodiment of the present invention. As the fractional fetal DNA concentration becomes lower, the degree of chromosome 21 overrepresentation diminishes and thus a larger number of informative wells for accurate disease classification is required. Hence, simulations were further performed for fetal DNA concentrations of 50%, 25% and 10% for a total well number ranging from 384 to 7680 wells at $m_r$=0.5.

FIG. 12 is a table 1200 showing results of computer simulation of accuracies of digital RCD analysis at $m_r$=0.5 for the classification of samples from euploid or trisomy 21 fetuses with different fractional concentrations of fetal DNA according to an embodiment of the present invention. The performance of digital RCD is better for cases with a higher fetal DNA fractional concentration. At 25% fetal DNA concentration and a total number of 7680 PCR analyses, 97% of both euploid and aneuploid cases would be classifiable with no incorrect classification. The remaining 3% of cases require further analyses until classification can be achieved.

The procedures for simulating digital RCD analyses were similar to those described for digital RNA-SNP analysis. The steps for the simulations are described below:

In step 1, two random numbers under the Poisson probability density function were generated to represent the reference locus, chromosome 1, and the chromosome 21 locus. For subjects carrying euploid fetuses, the average concentrations of both the chromosome 1 and chromosome 21 loci were the same. In this simulation analysis, an average template concentration of 0.5 for each locus per well was used. For subjects carrying trisomy 21 fetuses, the $m_r$ in this simulation was 0.5 but the average concentration of the chromosome 21 locus per well would depend on the fractional fetal DNA concentration in the tested sample, as shown in Table 700. The distribution of the reference and/or the chromosome 21 loci to a well was determined by the random numbers representing the respective locus which were generated according to the Poisson probability density function with the appropriate average concentration of the locus per well.

In step 2, step 1 was repeated until the desired number of wells had been generated, e.g. 384 wells for a 384-well plate experiment. The numbers of wells positive for chromosome 1 only and chromosome 21 only were counted. The number of the informative wells was the total number of wells positive for either one of the chromosomes but not both. The proportion of informative wells positive for chromosome 21 ($P_r$) was then calculated. The upper and lower boundaries of the relevant SPRT curves to accept the null or alternative hypothesis were calculated as described in the earlier section on SPRT analysis.

In step 3, 5000 simulations were performed for each of the two scenarios of the pregnant woman carrying a euploid or a trisomy 21 fetus. Each simulation could be regarded as an independent biological sample obtained from pregnant women. In Table 1100, the correct classification of euploid cases refers to those euploid cases in which the null hypothesis was accepted and the incorrect classification of euploid cases refers to those euploid cases in which the alternative hypothesis was accepted. Similarly, those trisomy 21 cases in which the alternative hypothesis was accepted were regarded as correctly classified and those trisomy 21 cases in which the null hypothesis was accepted were regarded as incorrectly classified. For both groups, those cases in which neither the null or alternative hypothesis was accepted after the pre-specified total number of wells had been simulated were regarded as unclassified.

In step 4, steps 1 to 3 were repeated for samples with 10% 25%, 50% and 100% fetal DNA at total well numbers ranging from 384 to 7680.

II. Validation of Trisomy 21 Detection

A. RNA-SNP for PLAC4

The practical feasibility of digital RNA-SNP was demonstrated using the rs8130833 SNP on the PLAC4 gene on chromosome 21 (Lo, Y M D et al. 2007 *Nat Med* 13, 218-223). Placental DNA and RNA samples from two euploid and two trisomy 21 heterozygous placentas were analyzed. The placental DNA samples were analyzed with the digital RNA-SNP protocol but with the omission of the reverse transcription step, thus essentially converting the procedure to digital DNA-SNP analysis. To strike a balance between the chance of correct case classification and the proportion of informative wells, we diluted the samples aiming for one allele of any type per well and confirmed by a 96-well digital PCR analysis. This was followed by a 384-well digital RNA-SNP experiment. $P_r$ and $m_r$ were calculated and the SPRT curve for this $m_r$ value was used for data interpretation.

FIG. 13A shows a table 1300 of digital RNA-SNP analysis in placental tissues of euploid and trisomy 21 pregnancies according to an embodiment of the present invention. Genotypes were determined by mass spectrometric assay. "Euploid" was assigned when the experimentally obtained $P_r$ was below the unclassifiable region; "T21", representing trisomy 21, was assigned when the experimentally obtained $P_r$ was above the unclassifiable region. T21, trisomy 21. Each of these cases was correctly classified, using both the DNA and RNA samples, with one 384-well experiment.

We further tested plasma RNA samples from nine women carrying euploid fetuses and four women carrying trisomy 21 fetuses. FIG. 13B shows a table 1350 of digital RNA-SNP analysis of maternal plasma from euploid and trisomy 21 pregnancies according to an embodiment of the present invention. All of the cases were correctly classified. Initial results for one trisomy 21 case (M2272P) fell within the unclassifiable region between the SPRT curves after one 384-well experiment. Thus, an additional 384-well run was performed. New $m_r$ and $P_r$ values were calculated from the aggregated data from the total of 768 wells and the classification was performed using a new set of SPRT curves selected based on this $m_r$ value. The case was then scored correctly as aneuploid.

Our experimental and simulation data show that digital RNA-SNP is an effective and accurate method for trisomy 21 detection. As PLAC4 mRNA in maternal plasma is derived purely from the fetus, for 12 of the 13 maternal plasma samples tested, only one 384-well digital PCR experiment was required for correct classification. This homogenous, real-time digital PCR-based approach thus offers an alternative to the mass spectrometry-based approach for RNA-SNP analysis. Apart from placental-specific mRNA transcripts, we also envision that other types of fetal-specific nucleic acid species in maternal plasma could be used for digital PCR-based detection of fetal chromosomal aneuploidies. One example is fetal epigenetic markers which have recently been used for the noninvasive prenatal detection of trisomy 18 using the epigenetic allelic ratio (EAR) approach (Tong Y K et al. 2006 *Clin Chem,* 52, 2194-2202). Thus, we predict that digital EAR would be a possible analytical technique.

B. RCD

Figure 14A:
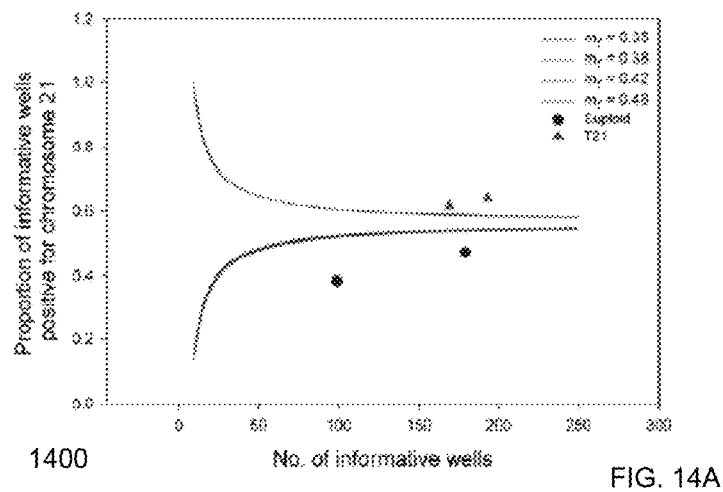
FIG. 14A-14C show plots illustrating a cutoff curve resulting from an RCD analysis according to an embodiment of the present invention.

The practical feasibility of digital RCD for trisomy 21 detection was also investigated using a PCR assay targeting paralogous sequences on chromosome 21 and 1. Paralogous loci were used here by way of examples. Non-paralogous sequences on chromosome 21 and any other reference chromosome can also be used for RCD. Placental DNA samples from two euploid and two trisomy 21 placentas were diluted to approximately one target template from either chromosome per well and confirmed by a 96-well digital PCR analysis. Each confirmed sample was analyzed by a 384-well digital RCD experiment and the values of $P_r$ and $m_r$ were calculated. For digital RCD, the chromosome 1 paralog was the reference template. This $m_r$ value was used to select a corresponding set of SPRT curves for data interpretation. All of the placental samples were correctly classified as shown in FIG. 14A.

Figure 14B:
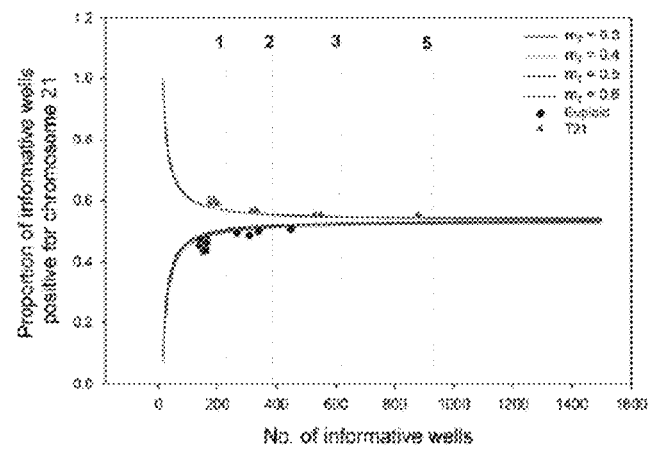
Figure 14C:
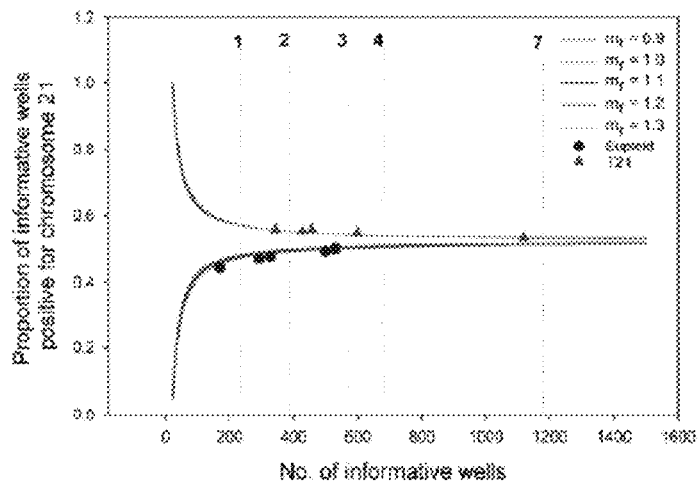

To demonstrate that the digital RCD approach can be used to detect trisomy 21 DNA which is mixed with an excess of euploid DNA, such as the scenario of fetal DNA in maternal plasma, mixtures containing 50% and 25% of trisomy 21 placental DNA in a background of euploid maternal blood cell DNA were analyzed. Placental DNA from 10 trisomy 21 and 10 euploid cases was each mixed with an equal amount of euploid maternal blood cell DNA, thus producing twenty 50% DNA mixtures. FIG. 14B shows a plot 1440 illustrating the SPRT interpretation for RCD analysis of the 50% fetal DNA mixtures according to an embodiment of the present invention. Similarly, placental DNA from 5 trisomy 21 and 5 euploid cases was each mixed with 3 times excess of euploid maternal blood cell DNA, thus producing ten 25% DNA mixtures. FIG. 14C shows a plot 1470 illustrating the SPRT interpretation for RCD analysis of the 25% fetal DNA mixtures. All the euploid and aneuploid DNA mixtures were correctly classified, as shown in FIGS. 14B and 14C.

Each sample reached the point of being classifiable after a number of 384-well digital PCR analyses as marked on FIGS. 14B and 14C. For the 50% DNA mixtures, the number of 384-well plates required ranged from one to five. For the 25% DNA mixtures, the number of 384-well plates required ranged form one to seven. The cumulative proportion of cases being correctly classified with the addition of every 384 digital PCR analyses were as predicted by the computer simulation presented in Table 1200.

III. Method with Digital PCR

A. Digital RNA-SNP

All RNA samples were first reverse transcribed with a gene-specific reverse transcription primer using the ThermoScript reverse transcriptase (Invitrogen). Sequence of the reverse transcription primer was 5'-AGTATATAGAACCAT-GTTTAGGCCAGA-3' (SEQ ID NO:1) (Integrated DNA Technologies, Coralville, IA). The subsequent treatment of the reverse transcribed RNA (i.e. the cDNA) samples for digital RNA-SNP, and DNA samples (e.g. placental DNA) was essentially the same. Prior to digital PCR analysis, DNA and the cDNA samples were first quantified using a real-time PCR assay towards PLAC4, consisting of primers 5'-CCGCTAGGGTGTCTTTTAAGC-3' (SEQ ID NO:2), 5'-GTGTTGCAATACAAAATGAGTTTCT-3' (SEQ ID NO:3), and the fluorescent probe 5'-(FAM)ATTGGAG-CAAATTC(MGBNFQ)-3' (SEQ ID NO:4) (Applied Biosystems, Foster City, CA), where FAM is 6-carboxyfluorescein and MGBNFQ is a minor groove binding non-fluorescent quencher.

A calibration curve was prepared by serial dilutions of HPLC-purified single-stranded synthetic DNA oligonucleotides (Proligo, Singapore) specifying the amplicon. The sequence was 5'-CGCCGCTAGGGTGTCTTTTAAGCTAT-TGGAGCAAATTCAAATTTGGCT-TAAAGAAAAAGAAACTCATTTTGTATTGCAACAC-CAGGAGTATCCCAAGGGACTCG-3' (SEQ ID NO:5). The reaction was set up using 2× TaqMan Universal PCR Master Mix (Applied Biosystems) in a reaction volume of 25 µL. 400 nM of each primer and 80 nM of the probe were used in each reaction. The reaction was initiated at 50° C. for 2 min, followed by 95° C. for 10 min and 45 cycles of 95° C. for 15s and 60° C. for 1 min in an ABI PRISM 7900HT Sequence Detection System (Applied Biosystems). Serial dilutions of the DNA or cDNA samples were then undertaken such that the subsequent digital PCR amplification could be performed at approximately one template molecule per well. At such a concentration, it was expected that approximately 37% of the reaction wells would show negative amplification and was first confirmed by conducting a 96-well digital real-time PCR analysis. This was followed by digital RNA-SNP analysis conducted in 384-well plates using a set of non-intron spanning primers: the forward primer 5'-TTTGTATTGCAACACCATTTGG-3' (SEQ ID NO:6) and the gene-specific reverse transcription primer described above.

Two allele-specific TaqMan probes targeting each of the two alleles of the rs8130833SNP on the PLAC4 sequence were designed. Their sequences were 5'-(FAM) TCGTCGTCTAACTTG(MGBNFQ)-3' (SEQ ID NO:7) and 5'-(VIC)ATTCGTCATCTAACTTG(MGBNFQ)-3' (SEQ ID NO:8) for the G and A alleles, respectively. The reaction was set up using 2× TaqMan Universal PCR Master Mix in a reaction volume of 5 µL. Each reaction contains 1× TaqMan Universal PCR Master Mix, 572 nM of each primer, 107 nM of the allele-G-specific probe and 357 nM of the allele-A-specific probe. The reaction was carried out in the ABI PRISM 7900HT Sequence Detection System. The reaction was initiated at 50° C. for 2 min, followed by 95° C. for 10 min and 45 cycles of 95° C. for 15s and 57° C. for 1 min. During the reaction, the fluorescence data were collected by the "Absolute Quantification" application of the SDS 2.2.2 software (Applied Biosystems). The software automatically calculated the baselines and the threshold values. The number of wells which were positive for either the A or the G alleles was recorded and subjected to SPRT analysis.

B. Digital RCD Analysis

All placental and maternal buffy coat DNA samples used in this study were first quantified by the NanoDrop spectrophotometer (NanoDrop Technology, Wilmington, DE). The DNA concentration is converted to copies/µL using a conversion of 6.6 pg/cell. The amount of DNA corresponding to approximately one template per well was determined by serially diluting the DNA samples and confirmed with the real-time PCR assay in a 96-well format where we expect approximately 37% of the wells to show negative amplification. The PCR setup for the confirmatory plate was the same as described below except that only the probe for the reference chromosome was added. In the digital RCD analysis, the paralogous loci on chromosome 21 and 1 (Deutsch, S. et al. 2004 *J Med Genet* 41, 908-915) were first co-amplified by forward primer 5'-GTTGTTCTG-CAAAAAACCTTCGA-3' (SEQ ID NO:9) and reverse primer 5'-CTTGGCCAGAAATACTTCATTACCATAT-3' (SEQ ID NO:10). Two chromosome-specific TaqMan probes were designed to target the chromosome 21 and 1 paralogs, and their sequences were 5'-(FAM)TACCTC-CATAATGAGTAAA(MGBNFQ)-3' (SEQ ID NO:11) and 5'-(VIC)CGTACCTCTGTAATGTGTAA(MGBNFQ)-3' (SEQ ID NO:12), respectively. Each reaction contained 1× TaqMan Universal PCR Master Mix (Applied Biosystems), 450 nM of each primer, and 125 nM of each probe. The total reaction volume was 5 µL/well. The reaction was initiated at 50° C. for 2 min, followed by 95° C. for 10 min and 50 cycles of 95° C. for 15s and 60° C. for 1 min. All real-time PCR experiments were carried out on an ABI PRISM 7900HT Sequence Detection System (Applied Biosystems), and the fluorescence data were collected by the "Absolute Quantification" application of the SDS 2.2.2 software (Applied Biosystems). The default baselines and manual threshold values were used. The number of wells which were positive for either chromosome 21 or chromosome 1 was recorded and subjected to SPRT analysis. One or more 384-well plates would be analyzed until disease classification was possible by SPRT.

IV. Using Microfluidics-Based Digital PCR

A. Digital RNA-SNP

This example demonstrates the performance of digital PCR analysis using microfluidics-based digital PCR. A variant of this approach is illustrated here, by way of example but not by way of limitation to, using a Fluidigm BioMark™ System. This system can perform over 9000 digital PCRs per run.

Placental tissues and maternal peripheral blood samples were obtained from pregnant women carrying euploid or trisomy 21 fetuses. Genotyping of the rs8130833 SNP on the PLAC4 gene was carried out in placental DNA samples by primer extension followed by mass spectrometry. RNA was extracted from the placental and maternal plasma samples.

All RNA samples were reverse transcribed with a gene-specific reverse transcription primer (5'-AGTATATAGAAC-CATGTTTAGGCCAGA-3'; SEQ ID NO:13) using the ThermoScript reverse transcriptase (Invitrogen). For the placental cDNA samples, serial dilutions were performed such that the subsequent digital PCR amplification could be performed at approximately one template molecule per well.

Digital PCR was conducted on the BioMark System™ (Fluidigm) with a 12.765Digital Array (Fluidigm). Each Digital Array consists of 12 panels for accommodating 12sample-assay mixtures. Each panel is further partitioned into 765 wells for carrying out a 7-nL reaction/well. The rs8130833 SNP region on the PLAC4 gene was amplified by the forward primer (5'-TTTGTATTGCAACACCATTTGG-3'; SEQ ID NO:14) and the gene-specific reverse transcription primer described above. Two allele-specific TaqMan probes targeting each of the two alleles of the rs8130833 SNP were designed. Their sequences were 5'-(FAM) TCGTCGTCTAACTTG(MGBNFQ)-3' (SEQ ID NO:15) and 5'-(VIC)ATTCGTCATCTAACTTG(MGBNFQ)-3' (SEQ ID NO:16) for the G and A alleles, respectively. The reaction for one array panel was set up using 2× TaqMan Universal PCR Master Mix in a reaction volume of 10 µL. Each reaction contains 1× TaqMan Universal PCR Master Mix, 572 nM of each primer, 53.5 nM of the allele-G-specific probe, 178.5 nM of the allele-A-specific probe and 3.5 4 of the cDNA sample. One reaction panel was used for each placental cDNA sample while 12 panels were used for each maternal plasma sample. The sample-assay mixtures were loaded into the Digital Array by a NanoFlex™ IFC controller (Fluidigm). The reaction was carried out in the BioMark™ System. The reaction was initiated at 50° C. for 2 min, followed by 95° C. for 10 min and 40 cycles of 95 C for 15s and 57° C. for 1 min.

Placental RNA samples from one euploid and two T21 heterozygous placentas were analyzed in a 765-well reaction panel. For each sample, the number of informative wells, comprising the ones positive for either the A or the G allele (but not both), was counted. The proportion of the overrepresented allele among all the informative wells (Pr) was determined. SPRT curves appropriate for the exact average reference template concentration per well ($m_r$) of these runs were applied to determine if the experimentally-obtained Pr indicated a euploid or T21 sample. As shown in FIG. 15A, all RNA samples were correctly classified using this approach.

We further tested the plasma RNA samples from four women carrying euploid fetuses and one woman carrying a trisomy 21 fetus. Each sample was analyzed in twelve 765-well reaction panels, i.e. 9180 reactions per plasma RNA sample. FIG. 15B shows the number of informative wells for each of the 12 panels for this plasma RNA sample. As shown in the table, the template concentration in the plasma sample was so diluted that the number of informative wells in any one reaction panel was not sufficient for the SPRT classification. The informative wells from three reaction panels had to be combined before this sample was classified as a euploid sample (FIG. 15C). FIG. 15C shows that using the aggregated data from two to twelve panels, all of the plasma cases could be correctly classified.

Compared with the manual method for performing digital PCR, this microfluidics-based method is much more rapid and less labor-intensive. The whole process could be completed in two and a half hours.

B. Digital RNA-SNP Analysis for the Prenatal Detection of Trisomy 18

In this example, we used a digital PCR-based allelic discrimination assay on serpin peptidase inhibitor clade B (ovalbumin) member 2 (SERPINB2) mRNA, a placenta-expressed transcript on chromosome 18, to detect an imbalance in the ratio of polymorphic alleles for trisomy 18 fetuses. Extraction of DNA and RNA from placental tissue samples was performed using the QIAamp DNA Mini Kit (Qiagen, Hilden, Germany) and the TRIzol reagent (Invitrogen, Carlsbad, Calif.), respectively, as described in the manufacturers' protocols. The extracted placental RNA samples were subjected to DNase I treatment (Invitrogen) for removal of contaminating genomic DNA. Genotyping of the rs6098 SNP on the SERPINB2 gene was carried out in placental tissue DNA samples with a Homogenous MassEXTEND (hME) assay using the MassARRAY Compact (Sequenom, San Diego) as previously described.

Reverse transcription for the SERPINB2 transcript was performed on the placental tissue RNA samples with a gene-specific primer 5'-CGCAGACTTCTCACCAAACA-3' (SEQ ID NO:17) (Integrated DNA Technologies, Coralville, IA) using the ThermoScript reverse transcriptase (Invitrogen). All cDNA samples were diluted to a concentration such that the subsequent digital PCR amplification could be performed at an average concentration of one template molecule per reaction well. Digital PCR was set up using the TaqMan Universal PCR Master Mix (Applied Biosystems, Foster City, CA) and the BiomarkTM PCR Reagents (Fluidigm, San Francisco). The forward primer 5'-CTCA-GCTCTGCAATCAATGC-3' (SEQ ID NO:18) (Integrated DNA Technologies) and the reverse primer (identical to the gene-specific primer used for reverse transcription) were used at a concentration of 600 nM. The two TaqMan probes targeting the A or G allele of the rs6098 SNP on the SERPINB2 sequence were 5'-(FAM)CCACAGGGAATT-ATTT (MGBNFQ)-3' (SEQ ID NO:19) and 5'-(VIC) CCACAGGGGATTATTT(MGBNFQ)-3' (SEQ ID NO:20) (Applied Biosystems). FAM is 6-carboxyfluorescein and MGBNFQ is a minor groove-binding nonfluorescent quencher, and were used at concentrations of 300 nM and 500 nM, respectively. Each sample-reagent mix was partitioned into 765 reaction wells on a Biomark™ 12.765 Digital Array using the Nanoflex™IFC Controller (Fluidigm). After partitioning, the array was placed in the Biomark™ Real-time PCR System (Fluidigm) for thermal amplification and fluorescence detection. The reaction was initiated at 50°C. for 2 min and continued at 95°C. for 5 min followed by 45 cycles of 95°C. for 15 sec and 59°C. for 1 min. After amplification, the number of informative wells (one that was positive for either the A or G allele only) and the number of wells positive for both alleles were counted and subjected to sequential probability ratio test (SPRT) analysis.

For a heterozygous euploid fetus, the A and G alleles should be equally represented (1:1) in the fetal genome, whereas for trisomy 18, there would be an additional copy of one allele thus giving a ratio of 2:1 in the fetal genome. A series of SPRT curves were generated for interpretation of different samples. These curves illustrate the expected proportion of informative wells positive for the overrepresented allele $P_r$ (y-axis) for a given total number of informative wells (x-axis) needed for classification. For each sample, the experimentally derived $P_r$ was compared with the expected $P_r$ value. Samples above the upper curve were classified as trisomy 18, whereas those below the bottom curve were classified as euploid. The area between the two curves is the unclassifiable region.

The feasibility of digital RNA-SNP analysis for the detection of fetal trisomy 18 was demonstrated by using the rs6098 SNP on the SERPINB2 gene. Placental tissue DNA samples from subjects with euploid and trisomy 18 fetuses were first genotyped by mass spectrometry for identifying heterozygous cases. Nine euploid and three trisomy 18 heterozygous placentas were found and subjected to digital RNA-SNP analysis. For each sample, $P_r$ and $m_r$ were calculated, and the SPRT curve for this $m_r$ value was used for disease classification. As shown in FIG. 16A, all samples were correctly classified. The $P_r$ values for trisomy 18 placentas were above the unclassifiable region, whereas those for euploid placentas fell below this region.

Samples with SPRT curves based on $m_r$=0.1, 0.2, and 0.3 are illustrated in FIG. 16B. These data suggest that the digital RNA-SNP method is a valuable diagnostic tool for trisomy 18 pregnancies. The two curves represent the boundaries for the unclassifiable region. Samples with data points above the upper curve were classified as aneuploid, whereas those with data points below the bottom curve were classified as euploid.

C. Digital RCD Analysis

This example demonstrates the performance of digital RCD analysis using microfluidics-based digital PCR. A variant of this approach is illustrated here, by way of example but not by way of limitation to, using a Fluidigm BioMark™ System. This system can perform over 9000 digital PCRs per run.

Placental tissues, maternal blood cell and amniotic fluid samples were obtained from pregnant women carrying euploid or trisomy 21 (T21) fetuses. Placental DNA from 10 T21 and 10 euploid cases was each mixed with an equal amount of euploid maternal blood cell DNA, thus producing twenty 50% DNA mixtures. To ensure accurate fetal proportion in the mixture samples, the extracted DNA was first quantified by optical density (OD) measurement at 260 nm. They were then digitally quantified by the BioMark™ System (Fluidigm) using the 12.765 Digital Arrays (Fluidigm). The assay for quantifying the samples was the same as described below except that only the probe for the reference chromosome was used.

The chromosome dosage in the 50% DNA mixtures and amniotic fluid samples was determined by digital PCR analysis of a nonpolymorphic chromosome 21 locus relative to one located on chromosome 1. A 101-bp amplicon of a pair of paralogous loci on chromosome 21 and 1 was first co-amplified by forward primer 5'-GTTGTTCTG-CAAAAAACCTTCGA-3' (SEQ ID NO:21) and reverse primer 5'-CTTGGCCAGAAATACTTCATTACCATAT-3' (SEQ ID NO:22). Two chromosome-specific TaqMan probes were designed to distinguish between the chromosome 21 and 1 paralogs, and their sequences were 5'-(FAM)TACCTCCATAATGAGTAAA(MGBNFQ)-3' (SEQ ID NO:23) and 5'-(VIC)CGTACCTCTGTAATGTGTAA(MGBNFQ)-3' (SEQ ID NO:24), respectively. The use of paralogous loci was used here by way of example only. In other words, non-paralogous loci could also be used for such analysis.

In order to demonstrate the use of the digital RCD approach to detect trisomy 18 (T18), another assay targeting paralogous sequences on chromosome 21 and 18 was designed. A 128-bp amplicon of the paralogous loci on chromosome 21 and 18 was first co-amplified by forward primer 5'-GTACAGAAACCACAAACTGATCGG-3' (SEQ ID NO:25) and reverse primer 5'-GTCCAGGCT-GTGGGCCT-3' (SEQ ID NO:26). Two chromosome-specific TaqMan probes were designed to distinguish between the chromosome 21 and 18 paralogs, and their sequences were 5'-(FAM)AAGAGGCGAGGCAA(MGBNFQ)-3' (SEQ ID NO:27) and 5'-(VIC)AAGAGGACAGGCAAC (MGBNFQ)-3' (SEQ ID NO:28), respectively. The use of paralogous loci was used here by way of example only. In other words, non-paralogous loci could also be used for such analysis.

All experiments were carried out on the BioMark™ System (Fluidigm) using the 12.765 Digital Arrays (Fluidigm). The reaction for one panel was set up using 2× TaqMan Universal PCR Master Mix (Applied Biosystems) in a reaction volume of 10 µL. Each reaction contained 1× TaqMan Universal PCR Master Mix, 900 nM of each primer, 125 nM of each probe and 3.5 µL of a 50% placental/maternal blood cell DNA sample. The sample/assay mixture was loaded into the Digital Array by the NanoFlex™ IFC controller (Fluidigm). The reaction was carried out on the BioMark™ System for detection. The reaction was initiated at 50° C. for 2 min, followed by 95° C. for 10 min and 40 cycles of 95° C. for 15 s and 57° C. for 1 min.

The euploid and T21 50% placental/maternal blood cell DNA samples were analyzed on the digital arrays with the chr21/chr1 assay. For each sample, the number of informative wells, comprising the ones positive for only chr21 or chr1 markers (but not both), was counted.

Figure 18:
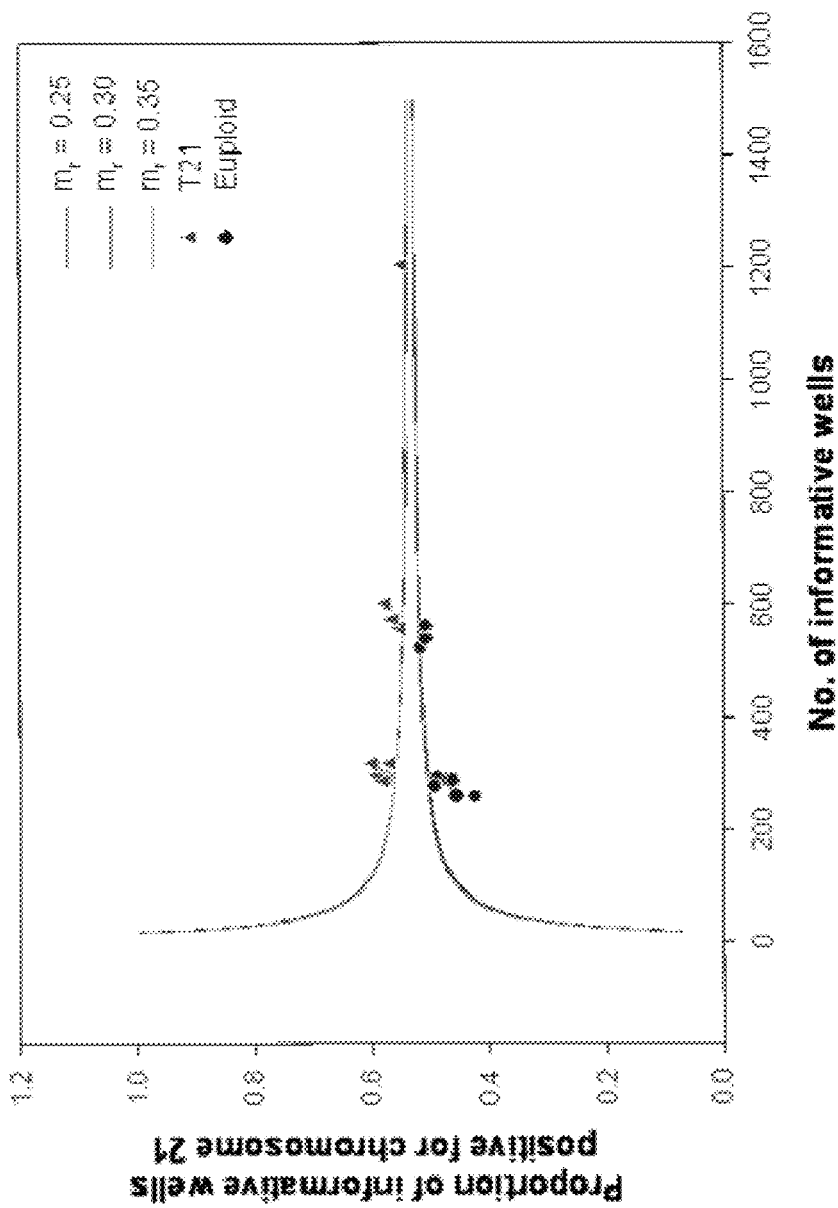
FIG. 18 shows a SPRT curve illustrating the decision boundaries for correct classification according to an embodiment of the present invention.

The proportion of the overrepresented marker among all the informative wells ($P_r$) was determined. SPRT curves appropriate for the exact average reference template concentration per well ($m_r$) for any one of the digital PCR panels were applied to determine if the experimentally-obtained $P_r$ indicated a euploid or T21 sample. Data were aggregated from extra panels for samples which remained unclassified until a decision could be made. As shown in FIG. 17, all 50% placental/maternal blood cell DNA samples were correctly classified using this approach with data ranging from one to four panels needed. A SPRT curve was also plotted to show the decision boundaries for correct classification, as shown in FIG. 18.

We further applied the RCD analysis on amniotic fluid samples obtained from 23 women carrying euploid fetuses and 6 women carrying T21 fetuses. Each sample was analyzed in a single 765-well reaction panel with the chr21 or chr1 assay. FIG. 19 shows the SPRT classification summary. As shown in FIG. 19, all the 29 samples were classified correctly. The digital RCD method is thus an alternative approach for the detection of trisomies using microsatellite (Levett L J, et al. A large-scale evaluation of amino-PCR for the rapid prenatal diagnosis of fetal trisomy. Ultrasound Obstet Gynecol 2001; 17: 115-8) or single nucleotide polymorphism (SNP) (Tsui N B, et al. Detection of trisomy 21 by quantitative mass spectrometric analysis of single-nucleotide polymorphisms. Clin Chem 2005; 51: 2358-62) markers or real-time non-digital PCR (Zimmermann B, et al. Novel real-time quantitative PCR test for trisomy 21. Clin Chem 2002; 48: 362-3) in miscellaneous sample types used for prenatal diagnosis, such as amniotic fluid and chorionic villus biopsies.

In an attempt to detect T18 cases, we applied the chr21/chr18 assay on 3 euploid and 5 T18 placental DNA samples. The proportion of the overrepresented marker among all the informative wells ($P_r$) was calculated. All of them were classified correctly except one T18 case was misclassified as euploid. The results were summarized in FIG. 20.

V. Using Multiplex Digital RCD Assays on Mass-Spectrometric Platform

The number of plasma DNA molecules that are present per unit volume of maternal plasma is limited (Lo Y M D. et al. 1998 *Am J Hum Genet* 62, 768-7758). For example, in early pregnancy, the median maternal plasma concentration of an autosomal locus, the β-globin gene, has been shown to be 986 copies/mL, with contributions from both the fetus and mother (Lo Y M D. et al. 1998 *Am J Hum Genet* 62, 768-7758). To capture 7,680 molecules, DNA extracted from some 8 mL of maternal plasma would be needed. This volume of plasma, obtainable from ~15 mL of maternal blood, is at the limit of routine practice. However, we envision that multiple sets of chr21 and reference chromosome targets can be combined for digital RCD analysis. For 5 pairs of chr21 and reference chromosome targets, just 1.6 mL of maternal plasma would be needed to provide the number of template molecules needed for analysis. Multiplex single molecule PCR could be performed. The robustness of such multiplex single molecule analysis has been demonstrated previously for single molecule haplotyping (Ding, C. and Cantor, C R. 2003 *Proc Natl Acad Sci U S A* 100, 7449-7453).

In one example, placental tissues and maternal blood cell samples were obtained from pregnant women carrying euploid or trisomy 21 (T21) fetuses. 5 euploid and 5 T21 placental DNA samples were each mixed with equal proportions of maternal blood cell DNA to produce 10 DNA mixtures mimicking plasma samples with 50% fetal DNA. To ensure accurate fetal proportion in the mixture samples, the extracted DNA was first quantified by optical density (OD) measurement at 260 nm. They were then digitally quantified by real-time PCR in 384-well format. The assay for quantifying the samples was the same as described in the previous example of digital RCD analysis.

The chromosome dosage in the 50% mix was determined by digital PCR analysis of a nonpolymorphic chromosome 21 locus relative to one located on chromosome 1. The method is called Digital Relative Chromosome Dosage (RCD) analysis. A 121-bp amplicon (inclusive of a 10-mer on each primer) of a pair of paralogous loci on chromosome 21 and 1 was co-amplified by forward primer 5'- ACGTTGGATGGTTGTTCTGCAAAAAACCTTCGA-3' (SEQ ID NO:29) and reverse primer 5'- ACGTTGGATGCTTGGCCAGAAATACTTCATTACCATAT-3' (SEQ ID NO:30). An extension primer which targets the base differences between chromosome 21 and chromosome 1 was designed, and its sequence is 5'-CTCATCCTCACTTCGTACCTC-3' (SEQ ID NO:31).

In order to demonstrate the utility of multiplexing digital PCR assays to detect T21cases, another digital RCD assay targeting paralogous sequences on chromosome 21 and 18 was designed. A 148-bp amplicon (inclusive of a 10-mer on each primer) of the paralogous loci on chromosome 21 and 18 was co-amplified by forward primer 5'-ACGTTGGATGGTACAGAAACCACAAACTGATCGG-3' (SEQ ID NO:32) and reverse primer 5'-ACGTTGGATGGTCCAGGCTGTGGGCCT-3' (SEQ ID NO:33). An extension primer which targets the base differences between chromosome 21 and chromosome 18 was designed, and its sequence is 5'-ACAAAAGGGGGAAGAGG-3' (SEQ ID NO:34).

Multiplex digital RCD analysis was performed using primer extension protocol. PCR reaction was set up using GeneAmp PCR Core Reagent Kit (Applied Biosystems) in a reaction volume of 5 μL. Each reaction contained 1× Buffer II, 2 mM MgCl$_2$, 200 μM dNTP mix, 0.2 U AmpliTaq Gold, 200 nM of each of the 4 primers and the 50% DNA mix. The assay/sample mixture was dispensed into 384-well PCR plate and the reaction was initiated at 50° C. for 2 min, followed by 95° C. for 10 min and 40 cycles of 95° C. for 15 s and 57° C. for 1 min.

PCR products were subjected to shrimp alkaline phosphatase (SAP) treatment to remove unincorporated dNTPs. The mixture was incubated at 37° C. for 40 min followed by 85° C. for 5 min. Primer extension reaction was then carried out. In brief, 771 nM of extension primer from chr21/chr1 assay, 1.54 μM of extension primer from chr21/chr18 assay, 0.67 U Thermosequenase (Sequenom), and 64 μM each of ddCTP, ddGTP, dATP and dTTP in an extension cocktail were added to the SAP-treated PCR products. The reaction conditions were 94° C. for 2 min, followed by 94° C. for 5 s, 50° C. for 5 s, and 72° C. for 5 s for 80 cycles. 16 μL of water and 3 mg of the Clean Resin (Sequenom) were added to the extension products for a final clean up. The mixtures were mixed in a rotator for 20 to 30 min, followed by a centrifugation step at 361 g for 5 min. Fifteen to 25 nL of the final products were dispensed onto a SpectroCHIP (Sequenom) by a MassARRAY Nanodispenser S (Sequenom). Data acquisition from the SpectroCHIP was done in the MassARRAY Analyzer Compact Mass Spectrometer (Sequenom). Mass data were imported into the MassARRAY Typer (Sequenom) software for analysis.

The five euploid and five T21 50% placental/maternal DNA samples were analyzed with the duplex RCD assay. For each sample, the number of informative wells from individual assay, comprising the ones positive for only chr21 or chr1 or chr18 markers, was counted. The proportion of the chr21 marker among all the informative wells ($P_r$) was calculated separately for each RCD assay. Sequential probability ratio test (SPRT) was then applied to determine if the $P_r$ indicated a euploid or T21 sample. By doing so, the number of wells required was reduced as each plate was counted twice.

The chr21/chr1 assay was usually applied first. If the sample remained unclassified, then the values from the chr21/chr18 assay would be added for further calculations. Extra plates were used for samples which remained unclassified until a decision could be made. As shown in FIG. 21, all euploid 50% mix samples were correctly classified using a single 384-well plate. Several T21 cases required 2 or more plates for correct classification. If only one assay was used, a greater number of plates would be needed to attain the number of informative wells required when classification was achieved. For example, data for case N0230 was unclassifiable when either of the RCD assays was used alone. However, correct classification was achieved when data from the two assays were combined. If the duplex RCD assays were not used, additional plates of analyses would be needed. We would expect a further reduction of well number with a higher level of multiplexing of assays.

In another example, we developed a 4-plex assay targeting 4 different amplicons on chromosome 21 and their corresponding paralogous partners located on other non-chromosome-21 autosomes. This 4-plex assay was used in digital RCD analysis followed by SPRT classification of samples from euploid and trisomy 21 pregnancies. DNA extractions from placental samples were performed using the QIAamp tissue kit (Qiagen, Hilden, Germany).

All placental and maternal buffy coat DNA samples used in this study were first quantified by the NanoDrop spectrophotometer (NanoDrop Technology, Wilmington, DE). The DNA concentration was converted to genome equivalent (GE)/µL using a conversion of 6.6pg/cell. The amount of DNA corresponding to approximately one template per well was determined by serially diluting the DNA samples. Under such a condition, we would expect approximately 37% of the wells to show negative amplification. In multiplex digital RCD analysis, 4 sets of paralogous sequence targets were selected: the paralogous loci on chromosome 21 and 1 were co-amplified by the forward primer 5'-ACGTTGGATGTTGATGAAGTCTCATCTCTACTTCG-3' (SEQ ID NO:35) and the reverse primer 5'-ACGTTGGATGCAATAAGCTTGGCCAGAAATACT-3' (SEQ ID NO:36), resulting in an amplicon of 81 bp. The paralogous loci on chromosome 21 and 7 were co-amplified by the forward primer 5'-ACGTTGGATGGAATTTAAGCTAAATCAGCCTGAACTG-3' (SEQ ID NO:37) and the reverse primer 5'-ACGTTGGATGGTTTCTCATAGTTCATCGTAGGCTTAT-3' (SEQ ID NO:38), resulting in an amplicon of 82 bp. The paralogous loci on chromosome 21 and 2were co-amplified by the forward primer 5'-ACGTTGGATGTCAGGCAGGGTTCTATGCAG-3' (SEQ ID NO:39) and the reverse primer 5'-ACGTTGGATGAGGCGGCTTCCTGGCTCTTG-3' (SEQ ID NO:40), resulting in an amplicon of 101 bp. The paralogous loci on chromosome 21and 6 were co-amplified by the forward primer 5'-ACGTTGGATGGCTCGTCTCAGGCTCGTAGTT-3' (SEQ ID NO:41) and the reverse primer 5'- ACGTTGGATGTTTCTTCGAGCCCTTCTTGG-3' (SEQ ID NO:42), resulting in an amplicon of 102 bp. Each reaction contained 10× buffer II (Applied Biosystems), MgCl$_2$ and 100 nM of each primer. The total reaction volume was 5 µL/well. The reaction was initiated at 95° C. for 5 min, followed by 45 cycles of 95° C. for 30 sec, 62° C. for 30 sec and 72° C. for 30 sec, and a final extension at 72° C. for 7 min. All conventional PCR amplifications were carried out on a GeneAmp PCR System 9700 (Applied Biosystems). The unincorporated nucleotides were deactivated by shrimp alkaline phosphatase (SAP) treatment. Each reaction contained 10× SAP buffer (Sequenom) and SAP enzyme (Sequenom). 2 µL of SAP mix was added to each PCR. The SAP reaction was incubated at 37° C. for 40 min and 85° C. for 5 min. After the SAP treatment, primer extension reaction was carried out on the PCR products using the iPLEX Gold kit (Sequenom). . The paralogous sequence mismatches (PSMs) on the paralogous loci on chromosomes 21 and 1 were interrogated by the extension primer 5'-GTCTCATCTCTACTTCGTACCTC-3' (SEQ ID NO:43). The PSMs on the paralogous loci on chromosomes 21 and 7 were interrogated by the extension primer 5'-TTTTACGCTGTCCCCATTT-3' (SEQ ID NO:44). The PSMs on the paralogous loci on chromosomes 21 and 2 were interrogated by the extension primer 5'-GGTCTATGCAGGAGCCGAC-3' (SEQ ID NO:45). The PSMs on the paralogous loci on chromosomes 21 and 6 were interrogated by the extension primer 5'-TGGGCGCGGGAGCGGACTTCGCTGG-3' (SEQ ID NO:46). Each reaction contained 10×iPLEX buffer (Sequenom), iPLEX termination mix (Sequenom), iPLEX enzyme (Sequenom) and 343 nM of each extension primer, except for the extension primer for PSMs on chromosomes 21 and 6 which was used at 1.03 µM. 2 µL of iPLEX mix was added to 5 µL of PCR product. The iPLEX reaction was cycled according to a 200-short-cycle program. Briefly, the samples were first denatured at 94° C. for 35 sec, followed by annealing at 52° C. for 5 sec and extension at 80° C. for 5 sec. The annealing and extension cycle was repeated four more times for a total of five cycles and then looped back to a 94° C. denaturing step for 5 sec, after which was the 5-cycle annealing and extension loop again. The five annealing and extension cycles with the single denaturing step were repeated 39 times for a total of 40. A final extension at 72° C. for 3min was performed. The iPLEX reaction products were diluted with 16 µL water and desalted by 6 mg resin for each PCR. The 384-well plate was centrifuged at 1600 g for 3 min before dispensing onto the SpectroCHIP (Sequenom) and the matrix-assisted laser desorption/ionization time-of-flight (MALDI-TOF) mass spectrometry MS Analysis (Sequenom).

The number of wells which were positive for only chromosome 21 or only the reference chromosome for each of the four assays was independently recorded. For each assay, the Poisson corrected numbers of molecules for chromosome 21 and the reference chromosome were calculated. The sum of the Poisson corrected number of molecules for chromosome 21 as well as the sum of the Poisson corrected number of reference chromosomes from all four assays were calculated and deemed as the informative counts for the 4-plex assay. The $P_r$ value was the chromosome 21 count for the 4-plex assay divided by the sum of the chromosome 21 and reference chromosome counts for the 4-plex assay. The experimentally derived $P_r$ values were subjected to SPRT analysis. One or more 384-well plates would be analyzed until disease classification was possible by SPRT. A total of two 50% euploid placental genomic DNA/50% maternal buffy coat DNA mix and two 50% trisomy 21 placental genomic DNA/50% maternal buffy coat DNA mix were analyzed.

The experimentally derived $P_r$ value would be compared with the expected value of $P_r$ to test the null or alternative hypotheses. Alternatively, neither the null or alternative hypothesis could be accepted if the $P_r$ for the given number of informative counts has not yet reached the required level of statistical confidence for disease classification. These cases were deemed unclassifiable until more data were available.

The results and the SPRT classification of each sample are tabulated in FIGS. 22A and 22B. The two euploid samples required 2 and 5 384-well multiplex digital RCD analyses before SPRT classification could be reached. Data from none of the individual member of the 4-plex assay allowed disease classification by SPRT. Both trisomy 21 samples were each correctly classified with just one 384-well multiplex digital RCD analysis. Similarly, data from none of the individual member of the 4-plex assay allowed disease classification by SPRT. However, the composite counts from the 4-plex assay allowed correct SPRT classification. These data illustrated that by using multiplex digital RCD, the effective number of informative counts were substantially increased for a given number of digital PCR analyses performed as compared to the use of a single-plex digital RCD assay.

VI. Using Digital Epigenetic Relative Chromosome Dosage

Here we outline an approach called digital epigenetic relative chromosome dosage (digital ERCD) in which epigenetic markers exhibiting a fetal-specific DNA methylation pattern, or other epigenetic changes, on a chromosome involved in a chromosomal aneuploidy (e.g. chromosome 21 in trisomy 21) and on a reference chromosome, are subjected to digital PCR analysis. The ratio of the number of wells positive for the chromosome 21 epigenetic marker to that positive for the reference chromosome epigenetic marker in plasma DNA extracted from pregnant women bearing normal fetuses will give us the reference range. The ratio will be expected to be increased if the fetus has trisomy 21. It is obvious to those of skill in the art that more than one chromosome 21 markers and more than one reference chromosome markers could be used in this analysis.

One example of a gene on chromosome 21 which exhibits a fetus (placenta)-specific methylation pattern is the *Holocarboxylase synthetase* (HLCS) gene. HLCS is hypermethylated in the placenta, but hypomethylated in maternal blood cells; and is covered in U.S. patent application Ser. No. 11/784,499, which is incorporated herein by reference. One example of a gene on a reference chromosome which exhibits a fetus (placenta)-specific methylation pattern is the RASSF1A gene on chromosome 3 [10]. RASSF1A is hypermethylated in the placenta but is hypomethylated in maternal blood cells, see U.S. patent application Ser. No. 11/784,501, which is incorporated herein by reference.

In the application of hypermethylated HLCS and hypermethylated RASSF1A to digital PCR detection of trisomy 21 in a fetus using maternal plasma, maternal peripheral blood is first collected. Then the blood is subjected to centrifugation and the plasma is harvested. DNA from the plasma is then extracted using techniques well-known to those of skill in the art, such as using a QIAamp Blood kit (Qiagen). The plasma DNA is then subjected to digestion using one or more methylation-sensitive restriction enzymes, such as HpaII and BstUI. These methylation-sensitive restriction enzyme(s) will cut the maternal, non-methylated versions of these genes, while leaving the fetal hypermethylated sequences intact. The digested plasma DNA sample is then diluted to an extent that on average approximately 0.2 to 1 molecule of either the restriction enzyme treated but intact HLCS or RASSF1A sequences will be detected per reaction well. Two real-time PCR systems will be used to amplify the diluted DNA, one with two primers and one TaqMan probe specific to the HLCS gene, encompassing the region that will be cut by the restriction enzyme(s) if the sequence in unmethylated; and the other one towards the RASSF1A gene, similarly with two primers and one TaqMan probe. With regard to the latter RASSF1A primer/probe set, one example has been described by Chan et al 2006, Clin Chem 52, 2211-2218. The TaqMan probes towards the HLCS and RASSF1A targets will have different fluorescent reporters, such as FAM and VIC, respectively. A 384-well plate is then used to perform the digital PCR experiment. The number of wells scored positive for just HLCS and those scored positive for just RASSF1A will be counted, and a ratio of these counts will be taken. The HLCS:RASSF1A ratio will be expected to be higher for maternal plasma taken from a pregnant woman carrying a trisomy 21 fetus, when compared with one carrying a normal euploid fetus. The degree of over-representation will be dependent on the average reference template concentration per well in the digital PCR run.

Other methods for scoring these results will be possible, for the example the counting of the number of wells positive for HLCS, irrespective of the concurrent positivity for RASSF1A; and vice versa for RASSF1A, irrespective of the concurrent positivity for HLCS. Furthermore, in replacement of calculating the ratio, either the total number, or the difference in the HLCS and RASSF1A counts could be used to indicate the trisomy 21 status of a fetus.

Apart from doing the digital PCR in plates, it will also be obvious to those of skill in the art that other variants of digital PCR can be used, e.g. microfluidics chips, nanoliter PCR microplate systems, emulsion PCR, polony PCR and rolling-circle amplification, primer extension and mass spectrometry, etc. These variants of digital PCR are named by way of examples, and not as limitations.

Apart from real-time PCR, it will also be obvious to those of skill in the art that methods such as mass spectrometry can be used to score the digital PCR results.

Apart from using methylation-sensitive restriction enzymes to differentiate the fetal and maternal versions of HLCS and RASSF1A, it will be obvious to those of skill in the art that other methods for ascertaining the methylation status would also be applicable, e.g. bisulfite modification, methylation-specific PCR, immunoprecipitation using antibody to methylated cytosine, mass spectrometry, etc.

It will also be obvious to those of skill in the art that the approach illustrated in this example and other examples in this patent application can be used in the other bodily fluids in which fetal DNA may be found, including maternal urine, amniotic fluid, transcervical washings, chorionic villus, maternal saliva, etc.

VII. Massively Parallel Genomic Sequencing Using Emulsion PCR and Other Strategies Here we shall describe another example whereby a digital readout of nucleic acid molecules can be used for the detection of fetal chromosomal aneuploidies, e.g. trisomy 21, in maternal plasma. Fetal chromosomal aneuploidy results from abnormal dose(s) of a chromosome or chromosomal region. It is desirable that noninvasive tests have high sensitivity and specificity to minimize false diagnoses. However, fetal DNA is present in low absolute concentration and represent a minor portion of all DNA sequences in maternal plasma and serum. Hence, the number of digital PCR sampling targeting specific gene loci cannot be increased infinitely within the same biological specimen. Hence, the analysis of multiple sets of specific target loci may be used to increase the amount of data that could be obtained from a specimen without increasing the number of digital PCR sampling performed.

Accordingly, embodiments allow the noninvasive detection of fetal chromosomal aneuploidy by maximizing the amount of genetic information that could be inferred from the limited amount of fetal nucleic acids which exist as a minor population in a biological sample containing maternal background nucleic acids. In one aspect, the amount of genetic information obtained is sufficient for accurate diagnosis yet not overly excessive so as to contain costs and the amount of input biological sample required.

Massively parallel sequencing, such as that achievable on the 454 platform (Roche) (Margulies, M. et al. 2005 *Nature* 437, 376-380), Illumina Genome Analyzer (or Solexa platform) or SOLiD System (Applied Biosystems) or the Helicos True Single Molecule DNA sequencing technology (Harris T D et al. 2008 *Science*, 320, 106-109), the single molecule, real-time (SMRT™) technology of Pacific Biosciences, and nanopore sequencing (Soni G V and Meller A. 2007 *Clin Chem* 53: 1996-2001), allow the sequencing of many nucleic acid molecules isolated from a specimen at high orders of multiplexing in a parallel fashion (Dear Brief Funct Genomic Proteomic 2003; 1: 397-416). Each of these platforms sequences clonally expanded or even non-amplified single molecules of nucleic acid fragments.

As a high number of sequencing reads, in the order of hundred thousands to millions or even possibly hundreds of millions or billions, are generated from each sample in each run, the resultant sequenced reads form a representative profile of the mix of nucleic acid species in the original specimen. For example, the haplotype, trascriptome and methylation profiles of the sequenced reads resemble those of the original specimen (Brenner et al Nat Biotech 2000; 18: 630-634; Taylor et al Cancer Res 2007; 67: 8511-8518). Due to the large sampling of sequences from each specimen, the number of identical sequences, such as that generated from the sequencing of a nucleic acid pool at several folds of coverage or high redundancy, is also a good quantitative representation of the count of a particular nucleic acid species or locus in the original sample.

In one embodiment, random sequencing is performed on DNA fragments that are present in the plasma of a pregnant woman, and one obtains genomic sequences which would originally have come from either the fetus or the mother. Random sequencing involves sampling (sequencing) a random portion of the nucleic acid molecules present in the biological sample. As the sequencing is random, a different subset (fraction) of the nucleic acid molecules (and thus the genome) may be sequenced in each analysis. Embodiments will work even when this subset varies from sample to sample and from analysis to analysis, which may occur even using the same sample. Examples of the fraction are about 0.1%, 0.5%, or 1% of the genome. In other embodiments, the fraction is at least any one of these values.

A bioinformatics procedure may then be used to locate each of these DNA sequences to the human genome. It is possible that a proportion of such sequences will be discarded from subsequent analysis because they are present in the repeat regions of the human genome, or in regions subjected to inter-individual variations, e.g. copy number variations. An amount of the chromosome of interest and of one or more other chromosomes may thus be determined.

In one embodiment, a parameter (e.g. a fractional representation) of a chromosome potentially involved in a chromosomal aneuploidy, e.g. chromosome 21 or chromosome 18 or chromosome 13, may then be calculated from the results of the bioinformatics procedure. The fractional representation may be obtained based on an amount of all of the sequences (e.g. some measure of all of the chromosomes) or a particular subset of chromosomes (e.g. just one other chromosome than the one being tested.)

This fractional representation is then compared to a reference range established in pregnancies involving normal (i.e. euploid) fetuses. It is possible that in some variants of the procedure, the reference range would be adjusted in accordance with the fractional concentration of fetal DNA (f) in a particular maternal plasma sample. The value of f can be determined from the sequencing dataset, e.g. using sequences mappable to the Y chromosome if the fetus is male. The value of f may also be determined in a separate analysis, e.g. using fetal epigenetic markers (Chan K C A et al 2006 Clin Chem 52, 2211-8) or from the analysis of single nucleotide polymorphisms.

In one aspect, even when a pool of nucleic acids in a specimen is sequenced at <100% genomic coverage, and among the proportion of captured nucleic acid molecules, most of each nucleic acid species is only sequenced once, dosage imbalance of a particular gene locus or chromosome can also be quantitatively determined. In other words, the dosage imbalance of the gene locus or chromosome is inferred from the percentage representation of the said locus among all mappable sequenced tags of the specimen.

In one aspect for the massively parallel genomic sequencing approach, representative data from all of the chromosomes may be generated at the same time. The origin of a particular fragment is not selected ahead of time. The sequencing is done at random and then a database search may be performed to see where a particular fragment is coming from. This is contrasted from situations when a specific fragment from chromosome 21 and another one from chromosome 1 are amplified.

In one example, a proportion of such sequences would be from the chromosome involved in an aneuploidy such as chromosome 21 in this illustrative example. Yet other sequences from such a sequencing exercise would be derived from the other chromosomes. By taking into account of the relative size of chromosome 21 compared with the other chromosomes, one could obtain a normalized frequency, within a reference range, of chromosome 21-specific sequences from such a sequencing exercise. If the fetus has trisomy 21, then the normalized frequency of chromosome 21-derived sequences from such a sequencing exercise will increase, thus allowing the detection of trisomy 21. The degree of change in the normalized frequency will be dependent on the fractional concentration of fetal nucleic acids in the analyzed sample.

In one embodiment, we used the Illumina Genome Analyzer for single-end sequencing of human genomic DNA and human plasma DNA samples. The Illumina Genome Analyzer sequences clonally-expanded single DNA molecules captured on a solid surface termed a flow cell. Each flow cell has 8 lanes for the sequencing of 8 individual specimens or pools of specimens. Each lane is capable of generating ~200 Mb of sequence which is only a fraction of the 3 billion basepairs of sequences in the human genome. Each genomic DNA or plasma DNA sample was sequenced using one lane of a flow cell. The short sequence tags generated were aligned to the human reference genome and the chromosomal origin was noted. The total number of individual sequenced tags aligned to each chromosome were tabulated and compared with the relative size of each chromosome as expected from the reference human genome or non-disease representative specimens. Chromosome gains or losses were then identified.

The described approach is only one exemplification of the presently described gene/chromosome dosage strategy. Alternatively, paired end sequencing could be performed. Instead of comparing the length of the sequenced fragments from that expected in the reference genome as described by Campbell et al (Nat Genet 2008; 40: 722-729), the number of aligned sequenced tags were counted and sorted according to chromosomal location. Gains or losses of chromosomal regions or whole chromosomes were determined by comparing the tag counts with the expected chromosome size in the reference genome or that of a non-disease representative specimen In another embodiment, the fraction of the nucleic acid pool that is sequenced in a run is further sub-selected prior to sequencing. For example, hybridization based techniques such as oligonucleotide array could be used to first sub-select for nucleic acid sequences from certain chromosomes, e.g. a potentially aneuploid chromosome and other chromosome(s) not involved in the aneuploidy tested. Another example is that a certain sub-population of nucleic acid sequences from the sample pool is sub-selected or enriched prior to sequencing. For example, it has been reported that fetal DNA molecules in maternal plasma are comprised of shorter fragments than the maternal background DNA molecules (Chan et al Clin Chem 2004; 50: 88-92). Thus, one may use one or more methods known to those of skill in the art to fractionate the nucleic acid sequences in the sample according to molecule size, e.g. by gel electrophoresis or size exclusion columns or by microfluidics-based approach. Yet, alternatively, in the example of analyzing cell-free fetal DNA in maternal plasma, the fetal nucleic acid portion could be enriched by a method that suppresses the maternal background, such as by the addition of formaldehyde (Dhallan et al JAMA 2004; 291: 1114-9).

Other single molecule sequencing strategies such as that by the Roche 454 platform, the Applied Biosystems SOLiD platform, the Helicos True Single Molecule DNA sequencing technology, the single molecule, real-time (SMRT™) technology of Pacific Biosciences, and nanopore sequencing could similarly be used in this application.

Examples of results and a further discussion (e.g. for sequencing and calculating parameters) may be found in concurrently filed application "DIAGNOSING FETAL CHROMOSOMAL ANEUPLOIDY USING GENOMIC SEQUENCING," which is incorporated by reference. Note that methods described herein for determining a cutoff value may be implemented when the reaction is sequencing, e.g. as described in this section.

The determination of the fractional concentration of fetal DNA in maternal plasma can also be done separate to the sequencing run. For example, the Y chromosome DNA concentration could be pre-determined using real-time PCR, microfluidics PCR or mass spectrometry. In fact, fetal DNA concentration could be determined using loci other than the Y chromosome and applicable to female fetuses. For example, Chan et al showed that fetal-derived methylated RASSF1A sequences would be detected in the plasma of pregnant women in the background of maternally derived unmethylated RASSF1A sequences (Chan et al, Clin Chem 2006;52:2211-8). The fractional fetal DNA concentration can thus be determined by dividing the amount of methylated RASSF1A sequences by the amount of total RASSF1A (methylated and unmethylated) sequences.

It is expected that maternal plasma would be preferred over maternal serum for practicing our invention because DNA is released from the maternal blood cells during blood clotting. Thus, if serum is used, it is expected that the fractional concentration of fetal DNA will be lower in maternal plasma than maternal serum. In other words, if maternal serum is used, it is expected that more sequences would need to be generated for fetal chromosomal aneuploidy to be diagnosed, when compared with a plasma sample obtained from the same pregnant woman at the same time.

Yet another alternative way of determining the fractional concentration of fetal DNA would be through the quantification of polymorphic differences between the pregnant women and the fetus (Dhallan R, et al. 2007 Lancet, 369, 474-481). An example of this method would be to target polymorphic sites at which the pregnant woman is homozygous and the fetus is heterozygous. The amount of fetal-specific allele can be compared with the amount of the common allele to determine the fractional concentration of fetal DNA.

In contrast to the existing techniques for detecting chromosomal aberrations, including comparative genomic hybridization, microarray comparative genomic hybridization, quantitative real-time polymerase chain reaction, which detect and quantify one or more specific sequence(s), massively parallel sequencing is not dependent on the detection or analysis of predetermined or a predefined set of DNA sequences. A random representative fraction of DNA molecules from the specimen pool is sequenced. The number of different sequence tags aligned to various chromosomal regions is compared between specimens containing or not containing tumoral DNA. Chromosomal aberrations would be revealed by differences in the number (or percentage) of sequences aligned to any given chromosomal region in the specimens.

In another example the sequencing technique on plasma cell-free DNA may be used to detect the chromosomal aberrations in the plasma DNA for the detection of a specific cancer. Different cancers have a set of typical chromosomal aberrations. Changes (amplifications and deletions) in multiple chromosomal regions may be used. Thus, there would be an increased proportion of sequences aligned to the amplified regions and a decreased proportion of sequences aligned to decreased regions. The percentage representation per chromosome could be compared with the size for each corresponding chromosome in a reference genome expressed as percentage of genomic representation of any given chromosome in relation to the whole genome. Direct comparisons or comparisons to a reference chromosome may also be used.

VIII. Mutation Detection

Fetal DNA in maternal plasma exists as a minor population, with an average of 3% to 6% of maternal plasma DNA being contributed by the fetus. Because of this reason, most of the previous work in the field has focused on the detection of DNA targets which the fetus has inherited from the father, and which are distinguishable from the majority maternal DNA background in maternal plasma. Examples of such previously detected targets include the SR Y gene on the Y chromosome (Lo Y M D et al. 1998 Am J Hum Genet, 62, 768-775) and the RHD gene when the mother is RhD-negative (Lo Y M D et al. 1998 N Engl J Med, 339, 1734-1738.

For fetal mutation detection, previous strategies using maternal plasma are limited to autosomal dominant conditions in which the father is a carrier, the exclusion of autosomal recessive diseases by direct mutation detection when the father and mother carries different mutations, or by linkage analysis (Ding C. et al 2004 Proc Nat Acad Sci USA 101, 10762-10767). These previous strategies have significant limitations. For example, for a couple where both the male and female partners carry the same mutation, then it would be impossible to carry out meaningful prenatal diagnosis by direct mutation detection in maternal plasma.

Figure 23:
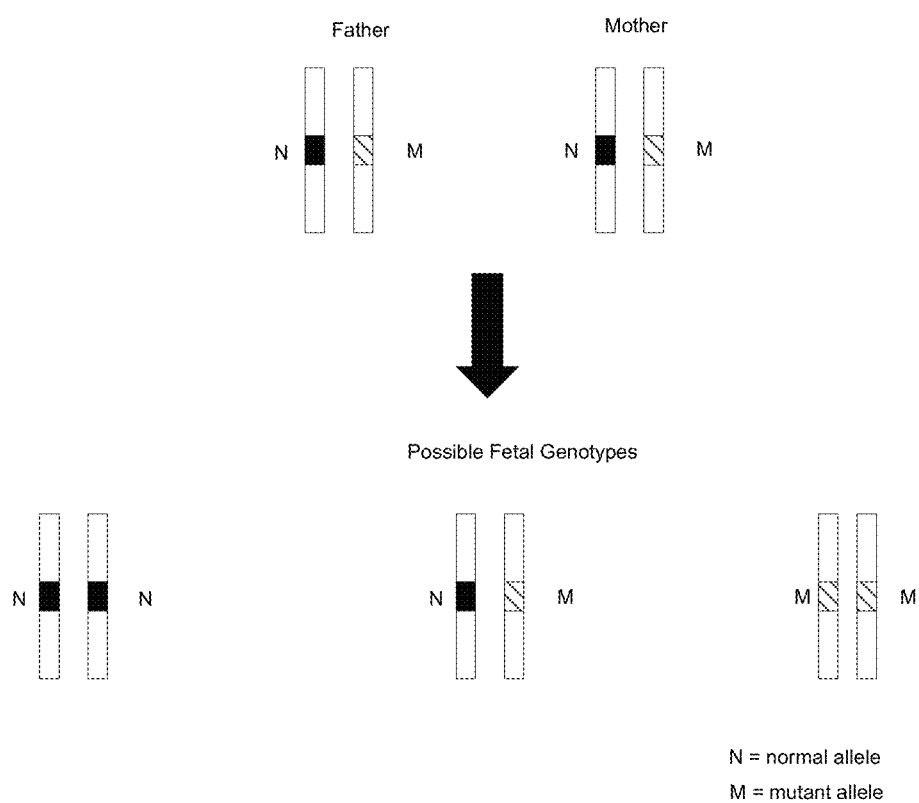
FIG. 23 shows a scenario where both the male and female partners carry the same mutation.

Such a scenario is illustrated in FIG. 23. In this scenario, there will be three possible fetal genotypes, NN, NM and MM, where N represents the normal allele and M represents the mutant allele. Examples of mutant alleles include those causing cystic fibrosis, beta-thalassemia, alpha-thalassemia, sickle cell anemia, spinal muscular atrophy, congenital adrenal hyperplasia, etc. Other examples of such disorders can be found in the Online Mendelian Inheritance in Man (OMIM) www.ncbi.nlm.nih.gov/sites/entrez?db=OMIM&itool=toolbar. In maternal plasma, most of the DNA will be coming from the mother and would be NM. For any of the three fetal genotypes, there will not be any unique fetal allele which would allow its unique detection in maternal plasma. Thus, the conventional strategy cannot be applied here.

Embodiments described herein allow handing such scenarios. In the scenario where the mother and fetus are both NM, then the N allele and M allele will be in allelic balance. However, if the mother is NM and the fetus is NN, then there will be allelic imbalance in maternal plasma, with the N allele being overrepresented. On the other hand, if the mother is NM and the fetus is MM, then there will be allelic imbalance in maternal plasma, with the M allele being overrepresented. Thus, for fetal mutation detection, the null hypothesis refers to the absence of allelic imbalance when the fetus is of the NM genotype. The alternative hypothesis refers to the presence of allelic imbalance and the fetal genotype could be NN or MM depending on whether the N or M allele is overrepresented.

The presence or absence of allelic imbalance can be determined by digital PCR using embodiments described herein. In a first scenario, a particular volume of maternal plasma contains the DNA released from 100 cells, in which 50 are from the mother and 50 are from the fetus. Thus, the fractional concentration of fetal DNA in this volume of plasma is 50%. When the mother is of the genotype NM, then there will be 50 N alleles and 50 M alleles contributed by the mother. If the fetus is of the genotype NM, then there will be 50 N alleles and 50 M alleles contributed by the fetus. Therefore, there will be no allelic imbalance between the N allele and the M allele, a total of 100 copies each. On the other hand, if the fetus is of the NN genotype, then there will be 100 fetal-derived N alleles in this volume of plasma. Thus, there will be a total of 150 N alleles to 50 M alleles. In other words, there will be allelic imbalance between N and M, with N being overrepresented at a ratio of 3:1 in relation to M.

In the converse situation, if the fetus is of the MM genotype, then there will be 100 fetal-derived M alleles in this volume of plasma. Thus, there will be 150 M alleles to 50 N alleles. In other words, there will be allelic imbalance between N and M, with M being overrepresented at a ratio of 3:1 in relation to N. Such allelic imbalance can be measured by digital PCR. The allele with the smaller number of positive wells is considered as the reference template. Similar to digital RNA-SNP and digital RCD analyses, the actual distribution of the alleles in the digital PCR experiment would be governed by the Poisson probability density function. Therefore, while the theoretical degree of allelic imbalance in the present scenario is 3:1, the expected degree of allelic imbalance would be dependent on the average template concentration per well during the digital PCR analysis. Thus interpretation cutoffs, such as for SPRT analysis, appropriate for the average reference template concentration per well ($m_r$) would need to be used for case classification.

Furthermore, the degree of allelic imbalance that needs to be measured is dependent on the fractional fetal DNA concentration. In contrast to the above example, let's consider a particular volume of maternal plasma contains the DNA released from 100 cells, in which 90 are from the mother and 10 are from the fetus. Thus, the fractional concentration of fetal DNA in this volume of plasma is 10%. When the mother is of the genotype NM, then there will be 90 N alleles and 90 M alleles contributed by the mother. If the fetus is of the genotype NM, then there will be 10 N alleles and 10 M alleles contributed by the fetus. Therefore, there will be no allelic imbalance between the N allele and the M allele, a total of 100 copies each. On the other hand, if the fetus is of the NN genotype, then there will be 20 fetal-derived N alleles in this volume of plasma. Thus, there will be a total of 110 N alleles to 90 M alleles.

In other words, there will be allelic imbalance between N and M, with N being overrepresented. In the converse situation, if the fetus is of the MM genotype, then there will be 20 fetal-derived M alleles in this volume of plasma. Thus, there will be 110 M alleles to 90 N alleles. In other words, there will be allelic imbalance between N and M, with M being overrepresented. The theoretical degree of allelic imbalance when the fetal DNA fractional concentration is 10% would be 110:90, which is different to the 3:1 ratio when there is 50% fetal DNA as shown in the above example. Thus interpretation cutoffs, such as for SPRT analysis, appropriate for the fetal DNA fractional concentration would need to be used for case classification.

Thus, plasma DNA will be extracted. The amount of maternal and fetal DNA in the plasma sample will be quantified, for example by the real-time PCR assays previously established (Lo, et al. 1998 *Am J Hum Genet* 62, 768-775) or other types of quantifier well-known to those of skill in the art, e.g. SNP markers (Dhallan R et al. 2007 *Lancet,* 369, 474-481) and fetal epigenetic markers (Chan K C A et al. 2006 *Clin Chem,* 52, 2211-2218). The fetal DNA percentage will be calculated. Then the quantified plasma DNA sample is prepared (e.g. diluted or concentrated) such that during digital PCR analysis, each reaction well will contain an average of one template molecule (can be either the N or M allele). The digital PCR analysis will be carried out using a pair of primers, plus two TaqMan probes, one specific to the N allele, while the other one specific to the M allele. The number of wells which are positive only for M and the number of wells which are positive only for N will be counted. The ratio of these wells will be used to determine if there is evidence of allelic imbalance. Statistical evidence of allelic imbalance can be sought by methods well-known to those of skill in the art, such as using SPRT. In one variant of this analysis, it is also possible to count the number of wells which are positive either for M only or for M and N; as well as to count the number of wells which are positive either for N only or for M and N; and to derive a ratio of these counts. Once again, statistical evidence of allelic imbalance can be sought by methods well-known to those of skill in the art, such as using SPRT.

The dosage determination of fetal gene mutation, called digital relative mutant dosage (RMD), was validated using female/male (XX/XY) DNA mixtures. Blood cell DNA from a male and a female was each mixed with male DNA, producing samples with XX or XY genotypes in a background of XY at fractional concentrations of 25% and 50%, respectively, as shown in FIG. 24A.

In addition, blood cell samples were also obtained from 12 male and 12 female subjects. The female blood cell DNA (genotype XX) was each mixed with a 3-fold excess of male blood cell DNA (genotype XY), thus producing 12 DNA mixtures with 25% of DNA with XX genotype in a background of 75% DNA with XY genotype, with results shown in FIG. 24B.

An aim of the SPRT analysis was to determine the minor genotype present in the background DNA. In DNA mixtures with 25% of XX DNA in a background of 75% XY DNA, the minor allele would be the Y derived from the 75% of DNA. Since 25% of the DNA in the sample was of XX genotype, if there were a total of 200 molecules of DNA in the sample, then 150 molecules would have originated from the XY individual. Hence, the number of Y alleles would be expected to be 75. The number of X alleles contributed by the male proportion of DNA (genotype XY) is also 75. The number of X alleles contributed by the female (genotype XX) is 50 (2 times 25). Therefore, X to Y ratio is 125/75=(1+25%)/(1−25%)=5/3.

For the second part of this study, blood cell samples were obtained from male and female subjects carrying HbE (G→A) and CD41/42 (CTTT/−) mutations on the beta-globin gene, i.e., the hemoglobin, beta (HBB) gene. To mimic maternal plasma samples obtained from heterozygous mothers (MN, where M=mutant and N=wildtype) bearing male fetuses with all possible genotypes (MM, MN or NN), blood cell DNA from males who were either homozygous for the wildtype alleles (NN) or heterozygous (MN) for one of the two mutations was each mixed with a blood cell DNA sample collected from females heterozygous for the same mutation (MN). DNA mixtures at various fractional male/mutant DNA concentrations were thus produced. Blood cell DNA sample from a female homozygous for the CD41/42 deletion (MM) was also used for preparing the DNA mixtures. To ensure an accurate male proportion for the SPRT classification, the fractional male DNA concentration of each DNA mixture was determined using the ZFY/X assay.

The digital ZFY/X assay was used for validating the SPRT as well as determining the fractional male DNA concentration in the DNA mixtures. The dosage of Zinc Finger protein sequences on chromosome X (ZFX) and Y (ZFY) was determined by digital PCR analysis. An 87-bp amplicon of the ZFX and ZFY loci was first co-amplified by the forward primer 5'-CAAGTGCTGGACTCAGATGTAACTG-3' (SEQ ID NO:47) and the reverse primer 5'-TGAAGTAATGTCAGAAGCTAAAACATCA-3' (SEQ ID NO:48). Two chromosome-specific TaqMan probes were designed to distinguish between the chromosome X and Y paralogs, and their sequences were 5'-(VIC)TCTTTAGCACATTGCA(MGBNFQ)-3' (SEQ ID NO:49) and 5'-(FAM)TCTTTACCACACTGCAC(MGBNFQ)-3' (SEQ ID NO:50), respectively.

The mutant dosage in the DNA mixtures was determined by digital PCR analysis of the normal allele relative to the mutant allele. For the HbE mutation, an 87-bp amplicon of the normal and mutant alleles was first co-amplified by the forward primer 5'-GGGCAAGGTGAACGTGGAT-3' (SEQ ID NO:51) and the reverse primer 5'-CTATTGGTCTCCTTAAACCTGTCTTGTAA-3' (SEQ ID NO:52). Two allele-specific TaqMan probes were designed to distinguish between the normal (G) and mutant (A) alleles, and their sequences were 5'-(VIC)TTGGTGGTGAGGCC (MGB-NFQ)-3' (SEQ ID NO:53) and 5'-(FAM)TGGTGGTAAGGCC (MGBNFQ)-3' (SEQ ID NO:54), respectively. Results for the HbE mutation are shown in FIG. 25.

For the CD41/42 deletion mutation, an 87-and 83-bp amplicon of the normal and mutant alleles was first co-amplified by the forward primer 5'-TTTTCCCACCCTTAGGCTGC-3' (SEQ ID NO:55) and the reverse primer 5'-ACAGCATCAGGAGTGGACAGATC-3' (SEQ ID NO:56), respectively. Two allele-specific TaqMan probes were designed to distinguish between the normal (without deletion) and mutant (with deletion) alleles, and their sequences were 5'-(VIC)CAGAGGTTCTTTGAGTCCT(MGBNFQ)-3' (SEQ ID NO:57) and 5'-(FAM)AGAGGTTGAGTCCTT (MGBNFQ)-3' (SEQ ID NO:58), respectively. Results for the HbE mutation are shown in FIGS. 26A and 26B.

These experiments were carried out on the BioMark™ System (Fluidigm) using the 12.765 Digital Arrays (Fluidigm). The reaction for one panel was set up using 2× TaqMan Universal PCR Master Mix (Applied Biosystems) in a reaction volume of 10 μL. For the CD41/42 and ZFY/X assays, each reaction contained 1× TaqMan Universal PCR Master Mix, 900 nM of each primer, 125 nM of each probe and 3.5 μL of DNA mixture at 1 ng/μL. For the HbE assay, 250 nM and 125 nM of probes targeting the normal (G) and mutant (A) alleles were added, respectively. The sample/assay mixture was loaded into the Digital Array by the NanoFlex™ IFC controller (Fluidigm). The reaction was carried out on the BioMark™ System for signal detection. The reaction was initiated at 50° C. for 2 min, followed by 95° C. for 10 min and 50 cycles of 95° C. for 15 s and 57° C. (for ZFY/X and CD41/42) or 56° C. (for HbE) for 1 min. At least one reaction panel was used for each case, and data were aggregated from extra panels for samples which remained unclassified until a decision could be made.

It will also be obvious to those of skill in the art that the digital PCR can be performed using methods well-known to those of skill in the art, e.g. microfluidics chips, nanoliter PCR microplate systems, emulsion PCR, polony PCR, rolling-circle amplification, primer extension and mass spectrometry.

IX. Example with Cancer

In one embodiment, the present invention may be performed to classify a sample as having allelic ratio skewing or not, as may occur in a cancerous tumor. In one aspect, for each case, the number of wells with positive signal for the A allele only, the G allele only, and both alleles were determined by digital PCR. The reference allele was defined as the allele with the smaller number of positive wells. (In the unlikely scenario that both alleles have the same number of positive wells, then either can be used as the reference allele.) The inferred average concentration of the reference allele per well ($m_r$) was calculated using the total number of wells negative for the reference allele, irrespective whether the other allele was positive, according to the Poisson probability density function. We use a hypothetical example to illustrate the calculation.

In a 96-well reaction, 20 wells are positive for the A allele, 24 wells are positive for the G allele, and 28 wells are positive for both alleles. The A allele would be regarded as the reference allele because less wells are positive for this allele. The number of wells negative for the reference allele would be 96−20−28=48. Therefore, $m_r$ can be calculated using the Poisson distribution and would be −ln(48/96)=0.693.

In the context of LOH detection, the null hypothesis refers to a sample that is assumed to lack allelic ratio skewing caused by the presence of a deletion of one allele. Under this assumption, the expected ratio of the number of positive wells for the two alleles would be 1:1 and, thus, the expected proportion of informative wells (wells positive for only one allele) containing the potentially overrepresented allele would be 0.5.

In the context of LOH detection, the alternative hypothesis refers to a sample that is assumed to have allelic ratio skewing caused by the presence of a deletion of one allele in 50% of the cells of the sample. As the allelic ratio between the overrepresented allele and the reference allele is 2:1, the average concentration of the overrepresented allele per well would be doubled that of the reference allele. However, the number of wells positive for the overrepresented allele would not be simply two times that for the reference allele but would follow the Poisson distribution.

An informative well is defined as a well positive for either the A or the G allele but not for both alleles. The calculation of the expected proportion of the number of wells containing the overrepresented alleles for samples with allelic ratio skewing is the same as is shown in Table 600. In the above example, if LOH is present in 50% of tumor cells, the average concentration of the G allele per well would be 2 times 0.693=1.386. If LOH is present in more than 50% of the tumor cells, then the average concentration of the G allele per well would be according to the formula: $1/[1-(\text{proportion with LOH})] \times m_r$.

The expected proportion of wells positive for the G allele would be $1-e^{-1.386}=0.75$ (i.e., 75% or 72 wells). Assuming that the positivity of a well for the A or G allele is independent, 0.5×0.75=0.375 of the wells would be positive for both the A and G alleles. Hence, 0.5−0.375=0.125 of the wells would be positive for the A allele only and 0.75−

0.375=0.375 of the wells would be positive for the G allele only. Therefore, the proportion of informative wells would be 0.125+0.375=0.5. The expected proportion of informative wells carrying the G allele would be 0.375/0.5=0.75. This expected value for $P_r$ can then be used for the construction of appropriate SPRT curves for determining whether allelic ratio skewing (i.e. LOH in this context) is present in the sample.

The actual proportion of informative wells carrying the non-reference allele experimentally determined by the digital PCR analysis ($P_r$) was then used to determine whether the null or alternative hypothesis would be accepted, or whether further analysis with more wells would be necessary. The decision boundaries for $P_r$ to accept the null or alternative hypothesis was calculated based on a threshold likelihood ratio of 8 as this value had been shown to provide satisfactory performance to discriminate samples with and without allelic imbalance in the context of cancer detection (Zhou, W, et al. (2001) *Nat Biotechnol* 19, 78-81; Zhou et a 2002, supra). In the above example, the number of informative wells would be 20+24=44 and the experimentally obtained $P_r$ would be 24/44=0.5455. The decision boundaries would be ≤0.5879 to accept the null hypothesis and ≥0.6739 to accept the alternative hypothesis. Therefore, the sample in this example would be classified as NOT having allelic ratio skewing.

In conclusion, we outlined an approach to detect sequence imbalance in a sample. In one embodiment, this invention can be used for the noninvasive detection of fetal chromosomal aneuploidy, such as trisomy 21 by analysis of fetal nucleic acids in maternal plasma. This approach can also be applied to other biological materials containing fetal nucleic acids, including amniotic fluid, chorionic villus samples, maternal urine, endocervical samples, maternal saliva, etc. First, we demonstrated the use of this invention for determining allelic imbalance of a SNP on PLAC4 mRNA, a placenta-expressed transcript on chromosome 21, in maternal plasma of women bearing trisomy 21 fetuses. Second, we demonstrated that our invention can be used as a non-polymorphism based method, through relative chromosome dosage (RCD) analysis, for the noninvasive prenatal detection of trisomy 21. Such a digital RCD-based approach involves the direct assessment of whether the total copy number of chromosome 21 in a sample containing fetal DNA is overrepresented with respect to a reference chromosome. Even without elaborate instrumentation, digital RCD allows the detection of trisomy 21 in samples containing 25% fetal DNA. We applied the sequential probability ratio test (SPRT) to interpret the digital PCR data. Computer simulation analyses confirmed the high accuracy of the disease classification algorithm.

We further outlined that the approach can be applied to the determination of other forms of nucleic acid sequence imbalances other than chromosomal aneuploidy, such as that for the detection of fetal mutation or polymorphism detection in maternal plasma and regional gains and losses in the genomes of malignant cells through the analysis of tumor-derived nucleic acids in plasma.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

Figure 27:
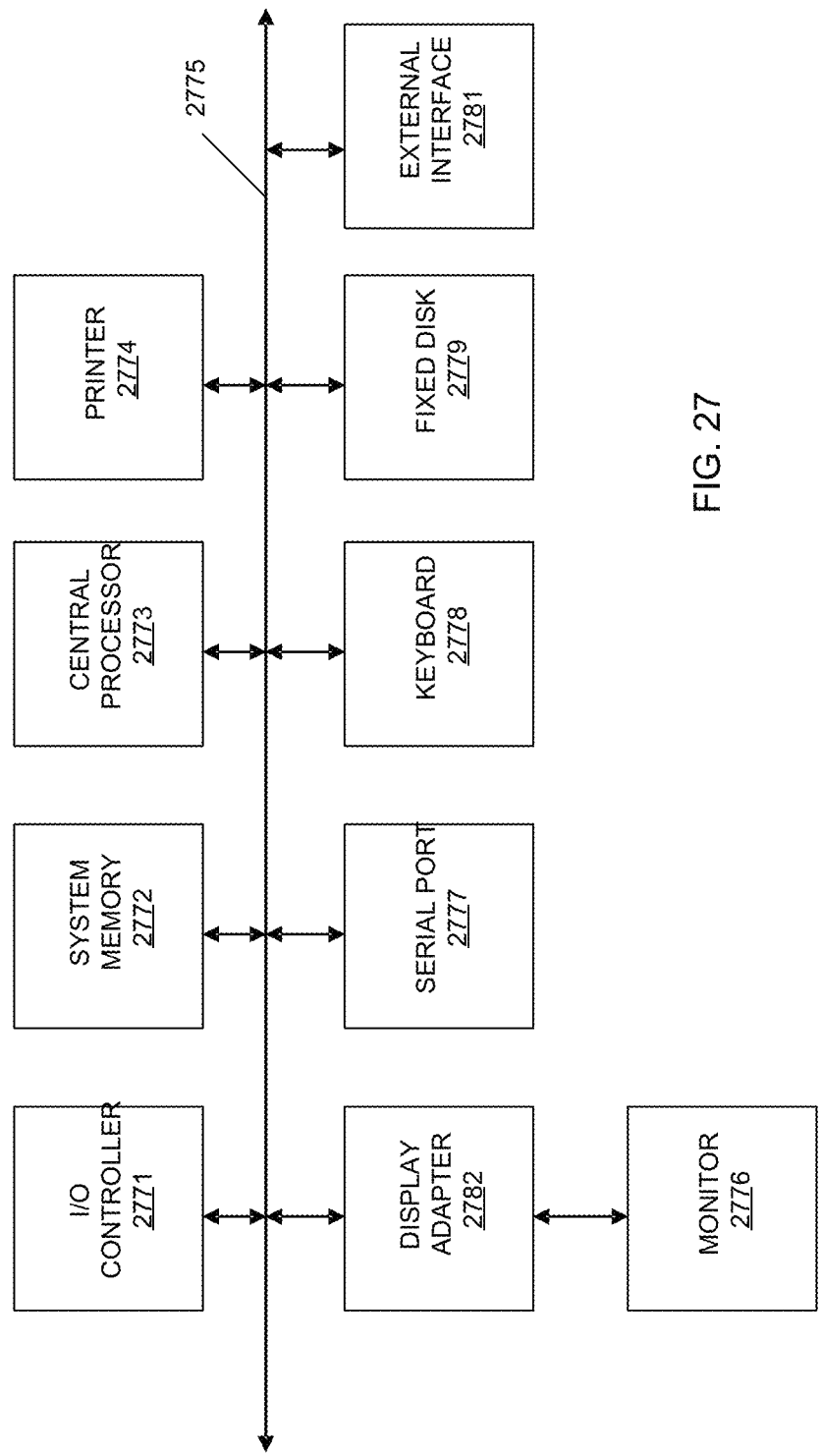
FIG. 27 shows a block diagram of an exemplary computer apparatus usable with system and methods according to embodiments of the present invention.

An example of a computer system is shown in FIG. 27. The subsystems shown in FIG. 27 are interconnected via a system bus 2775. Additional subsystems such as a printer 2774, keyboard 2778, fixed disk 2779, monitor 2776, which is coupled to display adapter 2782, and others are shown. Peripherals and input/output (I/O) devices, which couple to I/O controller 2771, can be connected to the computer system by any number of means known in the art, such as serial port 2777. For example, serial port 2777 or external interface 2781 can be used to connect the computer apparatus to a wide area network such as the Internet, a mouse input device, or a scanner. The interconnection via system bus allows the central processor 2773 to communicate with each subsystem and to control the execution of instructions from system memory 2772 or the fixed disk 2779, as well as the exchange of information between subsystems. The system memory 2772 and/or the fixed disk 2779 may embody a computer readable medium.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

All publications, patents, and patent applications cited herein are hereby incorporated by reference in their entirety for all purposes.

What is claimed is:

1. A method of measuring a fractional concentration of fetal DNA in a biological sample of a female subject pregnant with a fetus, the biological sample including a mixture of cell-free nucleic acid molecules from the female subject and from the fetus, and wherein the female subject is homozygous at a first locus for a first allele and the fetus is heterozygous at the first locus for the first allele and a second allele different from the first allele, the method comprising:

separating the cell-free nucleic acid molecules of the biological sample into a first plurality of reactions;

measuring signals from the first plurality of reactions, each of the first plurality of reactions involving the first locus, wherein the signals are indicative of a presence or absence of the first allele and the second allele at the first locus in each of the first plurality of reactions;

receiving, at a computer system, first data including the measured signals from the first plurality of reactions involving cell-free nucleic acid molecules from the biological sample, wherein the first data includes:

(1) a first set of quantitative data indicating a first number of reactions positive for the first allele; and (2) a second set of quantitative data indicating a second number of reactions positive for the second allele; and comparing, by the computer system, the first number to the second number to measure the fractional concentration of fetal DNA.

2. The method of claim 1, wherein the fractional concentration of fetal DNA is determined as a percentage using the first number and the second number.

3. The method of claim 1, further comprising:

receiving second data from a second plurality of reactions involving cell-free nucleic acid molecules from the biological sample, wherein the second data includes:

(1) a third set of quantitative data indicating a third amount of one or more clinically relevant nucleic acid sequences, the clinically relevant nucleic acid sequence not including the first locus; and (2) a fourth set of quantitative data indicating a fourth amount of one or more background nucleic acid sequences different from the one or more clinically relevant nucleic acid sequences, wherein the clinically relevant nucleic acid sequences and the background nucleic acid sequences come from cell-free nucleic acid molecules from the female subject, and wherein at least the clinically relevant nucleic acid sequences come from cell-free nucleic acid molecules from the fetus;

determining a parameter using the third amount and fourth amount, wherein the parameter provides a ratio between the third and fourth amounts;

deriving a first cutoff value from the fractional concentration F of fetal DNA by:

determining an expected ratio of the parameter when a nucleic acid sequence imbalance exists given F, where the expected ratio comprises:

a fetal contribution to the one or more clinically relevant nucleic acid sequences, the fetal contribution including F multiplied by a first expected number of copies of the clinically relevant nucleic acid sequences per fetal genome when the nucleic acid sequence imbalance exists; and maternal contributions to the one or more clinically relevant nucleic acid sequences and the one or more background nucleic acid sequences including: (1- F) multiplied by a second expected number of copies of the one or more clinically relevant nucleic acid sequences and the one or more background nucleic acid sequences per maternal genome, wherein the first expected number is different from the second expected number; and determining the cutoff value from the expected ratio of the parameter using a statistical method;

comparing the parameter to the cutoff value to determine whether the parameter exceeds the cutoff value; and based on the comparison, determining a classification of whether the nucleic acid sequence imbalance exists.

4. The method of claim 3, wherein the nucleic acid sequence imbalance is a chromosomal aneuploidy.

5. The method of claim 3, wherein one of the clinically relevant nucleic acid sequences is an allele of a genetic polymorphism, and one of the background nucleic acid sequences is another allele of the genetic polymorphism.

6. The method of claim 3, further comprising:

prior to performing the second plurality of reactions, enriching the biological sample for the one or more clinically relevant nucleic acid sequences and the one or more background nucleic acid sequences.

7. The method of claim 6, wherein enriching the biological sample for the one or more clinically relevant nucleic acid sequences and the one or more background nucleic acid sequences includes:

using an oligonucleotide array to select the one or more clinically relevant nucleic acid sequences and the one or more background nucleic acid sequences via hybridization.

8. The method of claim 6, wherein enriching the biological sample includes:

amplifying DNA from the one or more clinically relevant nucleic acid sequences and the one or more background nucleic acid sequences.

9. The method of claim 3, wherein the fractional concentration of fetal DNA is determined after the parameter is determined.

10. The method of claim 3, wherein the fractional concentration of fetal DNA is determined before the parameter is determined.

11. The method of claim 3, wherein the first plurality of reactions are the same as the second plurality of reactions.

12. The method of claim 3, wherein the cutoff value is determined using:

$$3 \times F + 2(1-F) : 2 \times F + 2 \times (1-F).$$

13. The method of claim 1, wherein a reaction is a sequencing reaction or an amplification reaction.

14. The method of claim 1, further comprising:
amplifying DNA from the locus in the first plurality of reactions;
providing a first probe corresponding to the first allele into the first plurality of reactions, the first probe providing a first positive signal when the first allele is present in a reaction; and
providing a second probe corresponding to the second allele into the first plurality of reactions, the second probe providing a second positive signal when the second allele is present in a reaction.

15. The method of claim 1, further comprising:
enriching the biological sample for DNA from the locus to obtain an enriched sample; and
after the enriching, performing the first plurality of reactions.

16. The method of claim 15, wherein enriching the biological sample includes using a hybridization-based technique.

17. The method of claim 16, wherein using the hybridization-based technique includes:
using an oligonucleotide array to select DNA from the locus.

18. The method of claim 16, wherein using the hybridization-based technique includes:
amplifying DNA from the locus.

19. A computer program product comprising a computer readable medium encoded with a plurality of instructions for controlling a measurement and computing system to perform a method of measuring a fractional concentration of fetal DNA in a biological sample of a female subject pregnant with a fetus, the biological sample including a mixture of cell-free nucleic acid molecules from the female subject and from the fetus, and wherein the female subject is homozygous at a first locus for a first allele and the fetus is heterozygous at the first locus for the first allele and a second allele different from the first allele, the method comprising:
separating the cell-free nucleic acid molecules of the biological sample into a first plurality of reactions using a controller of the system;
measuring, by a detector of the system, signals from the first plurality of reactions, each of the first plurality of reactions involving the first locus, wherein the signals are indicative of a presence or absence of the first allele and the second allele at the first locus in each of the first plurality of reactions;
receiving, at a processor of the system, first data including the measured signals from the first plurality of reactions involving cell-free nucleic acid molecules from the biological sample, wherein the first data includes:
(1) a first set of quantitative data indicating a first number of reactions positive for the first allele; and
(2) a second set of quantitative data indicating a second number of reactions positive for the second allele; and
comparing, by the processor of the system, the first number to the second number to measure the fractional concentration of fetal DNA.

20. The computer program product of claim 19, wherein the fractional concentration of fetal DNA is determined as a percentage using the first number and the second number.

21. The computer program product of claim 19, wherein the method further comprises:
receiving second data from a second plurality of reactions involving cell-free nucleic acid molecules from the biological sample, wherein the second data includes:
(1) a third set of quantitative data indicating a third amount of one or more clinically relevant nucleic acid sequences, the clinically relevant nucleic acid sequence not including the first locus; and
(2) a fourth set of quantitative data indicating a fourth amount of one or more background nucleic acid sequences different from the one or more clinically relevant nucleic acid sequences, wherein the clinically relevant nucleic acid sequences and the background nucleic acid sequences come from cell-free nucleic acid molecules from the female subject, and wherein at least the clinically relevant nucleic acid sequences come from cell-free nucleic acid molecules from the fetus;
determining a parameter using the third amount and fourth amount, wherein the parameter provides a ratio between the third and fourth amounts;
deriving a cutoff value from the fractional concentration F of fetal DNA by:
determining an expected ratio of the parameter when a nucleic acid sequence imbalance exists given F, where the expected ratio comprises:
a fetal contribution to the one or more clinically relevant nucleic acid sequences, the fetal contribution including F multiplied by a first expected number of copies of the clinically relevant nucleic acid sequences per fetal genome when the nucleic acid sequence imbalance exists; and
maternal contributions to the one or more clinically relevant nucleic acid sequences and the one or more background nucleic acid sequences including: (1-F) multiplied by a second expected number of copies of the one or more clinically relevant nucleic acid sequences and the one or more background nucleic acid sequences per maternal genome, wherein the first expected number is different from the second expected number; and
determining the cutoff value from the expected ratio of the parameter using a statistical method;
comparing the parameter to the cutoff value to determine whether the parameter exceeds the cutoff value; and
based on the comparison, determining a classification of whether the nucleic acid sequence imbalance exists.

22. The computer program product of claim 21, wherein the nucleic acid sequence imbalance is a chromosomal aneuploidy.

23. The computer program product of claim 21, wherein one of the clinically relevant nucleic acid sequences is an allele of a genetic polymorphism, and one of the background nucleic acid sequences is another allele of the genetic polymorphism.

24. The computer program product of claim 21, wherein prior to the second plurality of reactions, the biological sample is enriched for the one or more clinically relevant nucleic acid sequences and the one or more background nucleic acid sequences.

25. The computer program product of claim 21, wherein the fractional concentration of fetal DNA is determined after the parameter is determined.

26. The computer program product of claim 21, wherein the fractional concentration of fetal DNA is determined before the parameter is determined.

27. The computer program product of claim 21, wherein the first plurality of reactions are the same as the second plurality of reactions.

28. The computer program product of claim 21, wherein the cutoff value is determined using:

$3 \times F + 2(1-F) : 2 \times F + 2 \times (1-F)$.

29. The computer program product of claim 19, wherein a reaction is a sequencing reaction or an amplification reaction.

* * * * *

UNITED STATES PATENT AND TRADEMARK OFFICE
CERTIFICATE OF CORRECTION

PATENT NO. : 10,208,348 B2
APPLICATION NO. : 14/030904
DATED : February 19, 2019
INVENTOR(S) : Yuk-Ming Dennis Lo et al.

Page 1 of 1

It is certified that error appears in the above-identified patent and that said Letters Patent is hereby corrected as shown below:

In the Claims

In Column 76, Line 4 of Claim 3, please delete "deriving a first cutoff value" and insert --deriving a cutoff value--

Signed and Sealed this
Twenty-first Day of January, 2020

Andrei Iancu
*Director of the United States Patent and Trademark Office*